US008288110B2

(12) United States Patent
Lopez et al.

(10) Patent No.: US 8,288,110 B2
(45) Date of Patent: Oct. 16, 2012

(54) BIOMARKERS FOR DETECTING CANCER

(75) Inventors: Mary F. Lopez, Bedford, MA (US);
Scott Kuzdzal, Shelton, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 697 days.

(21) Appl. No.: 11/950,416

(22) Filed: Dec. 4, 2007

(65) Prior Publication Data

US 2008/0286814 A1 Nov. 20, 2008

Related U.S. Application Data

(60) Provisional application No. 60/868,400, filed on Dec. 4, 2006.

(51) Int. Cl.
*G01N 33/53* (2006.01)

(52) U.S. Cl. ....................................................... 435/7.1

(58) Field of Classification Search ........................ None
See application file for complete search history.

(56) References Cited

U.S. PATENT DOCUMENTS

| | | | |
|---|---|---|---|
| 4,499,052 A | 2/1985 | Fulwyler | |
| 4,879,231 A | 11/1989 | Stroman et al. | |
| 4,929,555 A | 5/1990 | Cregg et al. | |
| 5,028,545 A | 7/1991 | Soini | |
| 5,427,779 A | 6/1995 | Elsner et al. | |
| 5,530,101 A | 6/1996 | Queen et al. | |
| 5,585,089 A | 12/1996 | Queen et al. | |
| 5,674,872 A | 10/1997 | Johnson | |
| 5,693,761 A | 12/1997 | Queen et al. | |
| 5,693,762 A | 12/1997 | Queen et al. | |
| 5,798,230 A | 8/1998 | Bornkamm et al. | |
| 5,827,516 A | 10/1998 | Urban et al. | |
| 5,981,180 A | 11/1999 | Chandler et al. | |
| 6,407,213 B1 | 6/2002 | Carter et al. | |
| 6,537,749 B2 | 3/2003 | Kuimelis et al. | |
| 6,566,393 B1 | 5/2003 | Lee et al. | |
| 6,602,503 B1 | 8/2003 | Lobb et al. | |
| 6,653,341 B1 | 11/2003 | Littlefield et al. | |
| 6,916,661 B2 | 7/2005 | Chandler et al. | |
| 7,092,160 B2 | 8/2006 | Putnam | |
| 7,126,755 B2 | 10/2006 | Moon | |
| 7,176,236 B2 | 2/2007 | Lee et al. | |
| 7,190,522 B2 | 3/2007 | Moon | |
| 7,349,158 B2 | 3/2008 | Moon | |
| 7,399,643 B2 | 7/2008 | Moon | |
| 2002/0161181 A1* | 10/2002 | Jackowski et al. ............ | 530/326 |
| 2003/0232333 A1 | 12/2003 | Ladner | |
| 2004/0075907 A1 | 4/2004 | Moon | |
| 2004/0126875 A1 | 7/2004 | Putnam | |
| 2006/0040377 A1 | 2/2006 | Tsinberg | |

FOREIGN PATENT DOCUMENTS

| | | |
|---|---|---|
| EP | 239 400 | 8/1994 |
| WO | WO 90/07861 | 7/1990 |
| WO | WO 03/012451 | 2/2003 |
| WO | WO 03/046558 A2 * | 6/2003 |
| WO | WO 2005/098446 A2 * | 10/2005 |

OTHER PUBLICATIONS

Roodhooft et al (Pediatric Nephrology, 1990, 4:597-599).*
Tockman et al (Cancer Res., 1992, 52:2711s-2718s).*
Piver et al (Am J Ostet Gynecol, 1975, 122(3): Abstract).*
Sorace et al (BMC Bioinformatics, 2003, 4:24).*
NCBI Accession No. NP_000055 dated Mar. 15, 2009.
Adam et al., "Serum protein fingerprinting coupled with a pattern-matching algorithm distinguishes prostate cancer from benign prostate hyperplasia and healthy men," *Cancer Res.*, 2002, 62:3609-3614.
Adkins et al., "Toward a human blood serum proteome: analysis by multidimensional separation coupled with mass spectrometry," *Mol. Cell. Proteom.*, 2002, 1:947-955.
Anderson et al., "The human plasma proteome," *Mol. Cell. Proteom.*, 2004, 3(4):311-326.
Ardekani et al., "Clinical potential of proteomics in the diagnosis of ovarian cancer," *Expert Rev. Mol. Diagn.*, 2002, 2:312-320.
Baggerly et al., "Signal in noise: evaluating reported reproducibility of serum proteomic tests for ovarian cancer," *J. Natl. Cancer Inst.*, 2005, 97(4):307-309.
Bast et al., "New tumor markers: CA125 and beyond," *Int. J. Gynecol. Cancer*, 2005, 15(Suppl 3):274-281.
Bast, "Status of Tumor Markers in Ovarian Cancer Screening," *J. Clin. Oncol.*, 2003, 21:200-205.
Bhoola and Hoskins, "Diagnosis and management of epithelial ovarian cancer," *Obstet. Gynecol.*, 2006, 107:1399-1410.
Bird et al., "Single-Chain Antigen-Binding Proteins," *Science*, 1988, 242:423-426.
Bloor et al., "Expression of keratin K2e in cutaneous and oral lesions: association with keratinocyte activation, proliferation, and keratinization," *Am. J. Pathol.*, 2003, 162:963-975.
Boerner et al., "Production of antigen-specific human monoclonal antibodies from in vitro-primed human splenocytes," *J. Immunol.*, 1991, 147:86-95.
Boyce and Kohn, "Ovarian cancer in the proteomics era: diagnosis, prognosis, and therapeutics targets," *Int. J. Gynecol. Cancer*, 2005, 15(Suppl 3):266-273.
Burlingame et al., "Mass spectrometry," *Anal. Chem.*, 1998, 70:647R-716R.
Chen et al., "Identification of differential genes in ovarian cancer using representational difference analysis of cDNA," *Chin. Med. Sci. J.*, 2005, 3:185-189.
Cole et al., "The EBV-Hybridoma Technique and Its Application to Human Lung Cancer," *Monoclonal Antibodies and Cancer Therapy*, 1985, Alan R. Liss, Inc., pp. 77-96.
Crowe and Lee, "New role for nuclear hormone receptors and coactivators in regulation of BRCA1-mediated DNA repair in breast cancer cell lines," *Breast Cancer Res.*, 2006, 8:R1.

(Continued)

*Primary Examiner* — Sean Aeder
(74) *Attorney, Agent, or Firm* — Fish & Richardson P.C.

(57) ABSTRACT

The disclosure features, inter alia, a variety of biomarkers (e.g., biomarker peptides), compositions, and kits for use in methods for diagnosing a cancer. The biomarkers can be used, e.g., in methods for detecting a cancer in a subject. In addition, the disclosure also features methods of selecting a therapy for, and/or administering a therapy (e.g., a therapy comprising an anti-cancer agent) to, a subject having a cancer.

56 Claims, 8 Drawing Sheets

OTHER PUBLICATIONS

DeSouza et al., "Search for cancer markers from endometrial tissues using differentially labeled tags iTRAQ and cICAT with multidimensional liquid chromatography and tandem mass spectrometry," *J. Proteome Res.*, 2005, 4:377-386.

Di Tommaso et al., "Induction of Antigen-Specific Antibodies in Vaginal Secretions by Using a Nontoxic Mutant of Heat-Labile Enterotoxin as a Mucosal Adjuvant," *Infect. Immunity*, 1996, 64(3):974-979.

Diamandis, "Peptidomics for cancer diagnosis: present and future," *J. Proteome Res.*, 2006, 9:2079-2082.

Diamandis, "Point: proteomic patterns in biological fluids: do they represent the future of cancer diagnostics?" *Clin. Chem.*, 2003, 49:1272-1275.

Edwards et al., "The human cytotoxic T cell granule serine protease granzyme H has chymotrypsin-like (chymase) activity and is taken up into cytoplasmic vesicles reminiscent of granzyme B-containing endosomes," *J. Biol. Chem.*, 1999, 274(43):30468-30473.

Galfre et al., "Antibodies to major histocompatibility antigens produced by hybrid cell lines," *Nature*, 1977, 266:550-552.

Haddad et al., "Structure and evolutionary origin of the human granzyme H gene," *Int. Immunol.*, 1991, 1:57-66.

Hartmann et al., "Selective DNA Attachment of micro- and nanoscale particles to substrates," *J. Mater. Res.*, 2002, 17(2):473-478.

Hastie et al., "Flexible Discriminant Analysis by Optimal Scoring," *JASA*, 1994, 89:155-1270.

Hinnen et al., "Transformation of Yeast," *Proc. Natl. Acad. Sci. USA*, 1978, 75(4):1929-1933.

Hoogenboom and Chames, "Natural and designer binding sites made by phage display technology," *Immunol. Today*, 2000, 21(8):371-378.

Hoogenboom et al., "Antibody phage display technology and its applications," *Immunotechnology*, 1998, 4:1-20.

Hortin et al., "Proteomics: A new diagnostic frontier," *Clin. Chem.*, 2006, 52:1218-1222.

Hortin, "The MALDI-TOF mass spectrometric view of the plasma proteome and peptidome," *Clin. Chem.*, 2006, 52:1223-1237.

Huang and Stollar, "Construction of representative immunoglobulin variable region cDNA libraries from human peripheral blood lymphocytes without in vitro stimulation," *J. Immunol. Meth.*, 1991, 141:227-236.

Huston et al., "Protein engineering of antibody binding sites: recovery of specific activity in an anti-digoxin single-chain Fv analogue produced in *Escherichia coli*," *Proc. Natl. Acad. Sci. USA*, 1988, 85(16):5879-5883.

Ijichi et al., "Molecular cloning and characterization of a human homologue of TBPIP, a BRCA1 locus-related gene," *Gene*, 2000, 248:99-107.

Ito et al., "Transformation of Intact Yeast Cells Treated with Alkali Cations," *J. Bacteriol.*, 1983, 153:163-168.

Köhler and Milstein, "Continuous cultures of fused cells secreting antibody of predefined specificity," *Nature*, 1975, 256:495-497.

Kozak et al., "Characterization of serum biomarkers for detection of early stage ovarian cancer," *Proteomics*, 2005, 17:4589-4596.

Kozbor and Roder, "The production of monoclonal antibodies from human lymphocytes," *Immunol. Today*, 1983, 4:72-79.

Kumar and Hung, "Signaling Intricacies Take Center Stage in Cancer Cells," *Cancer Res.*, 2005, 65:2511-2515.

Lerner, "How to Make a Hybridoma," *Yale J. Biol. Med.*, 1981, 54:387-402.

Li et al., "Proteomics and bioinformatics approaches for identification of serum biomarkers to detect breast cancer," *Clin. Chem.*, 2002, 48:1296-1304.

Liotta and Petricoin, "Serum peptidome for cancer detection: spinning biologic trash into diagnostic gold," *J. Clin. Invest.*, 2006, 116:26-30.

Liotta et al., "Importance of communication between producers and consumers of publicly available experimental data," *J. Natl. Cancer Inst.*, 2005, 97(4):310-314.

Liu et al., "A model for random sampling and estimation of relative protein abundance in shotgun proteomics," *Anal. Chem.*, 2004, 76:4193-4201.

Lopez et al., "High-resolution serum proteomic profiling of Alzheimer's disease samples reveals disease-specific, carrier-protein-bound mass signatures," *Clin. Chem.*, 2005, 51(10):1946-1954.

Lowenthal et al., "Analysis of Albumin-Associated Peptides and Proteins from Ovarian Cancer Patients," *Clin. Chem.*, 2005, 51:1933-1945.

Makino et al., "Isolation and characterization of the human gene homologous to the Drosophila headcase (hdc) gene in chromosome bands 6q23-q24, a region of common deletion in human pancreatic cancer," *DNA Seq.*, 2001, 11:547-553.

Mehta et al., "Biomarker amplification by serum carrier protein binding," *Dis. Markers*, 2003, 19:1-10.

Miele et al., "NOTCH Signaling as a Novel Cancer Therapeutic Target," *Curr. Cancer Drug Targets*, 2006, 6:313-323.

Minakuchi et al., "Identification and characterization of SEB, a novel protein that binds to the acute undifferentiated leukemia-associated protein SET," *Eur. J. Biochem.*, 2001, 268:1340-1351.

Molinaro et al., "Prediction Error Estimation: A Comparison of Resampling Methods," *Bioinformatics*, 2005, 21(15):3301-3307.

Moss et al., "The role of CA125 in clinical practice," *J. Clin. Pathol.*, 2005, 58:308-312.

Nicholson et al., "Antibody Repertoires of Four- and Five-Feature Translocus Mice Carrying Human Immunoglobulin Heavy Chain and κ and λ Light Chain Yeast Artificial Chromosomes," *J. Immunol.*, 1999, 163:6898-6906.

Persson et al., "Generation of diverse high-affinity human monoclonal antibodies by repertoire cloning," *Proc. Natl. Acad. Sci. USA*, 1991, 88(6):2432-2436.

Petricoin et al., "Serum proteomic patterns for detection of prostate cancer," *J. Natl. Cancer Inst.*, 2002, 94:1576-1578.

Petricoin et al., "Use of proteomic patterns in serum to identify ovarian cancer," *Lancet*, 2002, 359:572-577.

Pieper et al., "The human serum proteome: display of nearly 3700 chromatographically separated protein spots on two-dimensional electrophoresis gels and identification of 325 distinct proteins," *Proteomics*, 2003, 3:1345-1364.

Pollice et al., "Functional and physical interaction of the human ARF tumor suppressor with Tat-binding protein-1," *J. Biol. Chem.*, 2004, 279(8):6345-6353.

Popov et al., "A Human Immunoglobulin λ Locus Is Similarly Well Expressed in Mice and Humans," *J. Exp. Med.*, 1999, 189(10):1611-1619.

Rickles, "Mechanisms of cancer-induced thrombosis in cancer," *Pathophysiol Haemost Thromb.*, 2006, 35:103-110.

Riechmann et al., "Reshaping human antibodies for therapy," *Nature*, 1988, 332:323-327.

Rogers et al., "Characterization of an alternative superantigen binding site expressed on a renal fibroblast cell line," *International Immunology*, 1995, 7(11):1721-1727.

Rosenblatt et al., "Serum proteomics in cancer diagnosis and management," *Ann. Rev. Med.*, 2004, 55:97-112.

Rothemund et al., "Depletion of the highly abundant protein albumin from human plasma using the Gradiflow," *Proteomics*, 2003, 3:279-287.

Scaglioni et al., "A CK2-Dependent Mechanism for Degradation of the PML Tumor Suppressor," *Cell*, 2006, 126:269-283.

Sedelies et al., "Discordant regulation of granzyme H and granzyme B expression in human lymphocytes," *J. Biol. Chem.*, 2004, 279(25):26581-26587.

Shiratsuchi et al., "Cloning and characterization of BAI2 and BAI3, novel genes homologous to brain-specific angiogenesis inhibitor 1 (BAI1)," *Cytogenet Cell Genet.*, 1997, 79:103-108.

Sieja et al., "Concentration of histamine in serum and tissues of the primary ductal breast cancers in women," *Breast*, 2005, 14:236-241.

Singet al., ROCR: An R Package for visualizing the performance of scoring classifiers. 2004 http://rocr.bioinf.mpi-sb.mpg.de.

Sorace and Zhan, "A data review and re-assessment of ovarian cancer serum proteomic profiling," *BMC Bioinformatics*, 2003, 4:24.

Sreekrishna et al., "Invertase gene (SUC2) of *Saccharomyces cerevisiae* as a dominant marker for transformation of *Pichia pastoris*," *Gene*, 1987, 59:115-125.

Srinivas et al., "Proteomics in early detection of cancer," *Clin. Chem.*, 2001, 47:1901-1911.

Tempest et al., "Reshaping a human monoclonal antibody to inhibit human respiratory syncytial virus infection in vivo," *Biotechnology*, 1991, 9(3):266-271.

Thompson et al., "Post-translationally modified S12, absent in transformed breast epithelial cells, is not associated with the 26S proteasome and is induced by proteasome inhibitor," *Int. J. Cancer*, 2004, 111:338-347.

Tirumalai et al., "Characterization of the low molecular weight human serum proteome," *Mol. Cell Proteomics*, 2003, 2:1096-2003.

Verhoeyen et al., "Reshaping Human Antibodies: Grafting an Antilysozyme Activity," *Science*, 1988, 239:1534-1536.

Veugelers et al., "A 4-Mb BAC/PAC contig and complete genomic structure of the GPC5/GPC6 gene cluster on chromosome 13q32," *Matrix Biol.*, 2001, 20:375-385.

Wang et al., "A simple affinity spin tube filter method for removing high-abundant common proteins or enriching low-abundant biomarkers for serum proteomic analysis," *Proteomics*, 2003, 3:243-248.

Wang et al., "Altered mRNA expressions of sialyltransferases in ovarian cancers," *Gynecol. Oncol.*, 2005, 99:631-639.

Ward et al., "Binding activities of a repertoire of single immunoglobulin variable domains secreted from *Escherichia coli*," *Nature*, 1989, 341:544-546.

Washburn et al., "Large-scale analysis of the yeast proteome by multidimensional protein identification technology," *Nat. Biotechnol.*, 2001, 19:242-247.

Whiteley, "Proteomic patterns for cancer diagnosis-promise and challenges," *Mol. BioSyst.*, 2006, 2:358-363.

Wulfkuhle et al., "Proteomic applications for the early detection of cancer," *Nat. Rev. Cancer*, 2003, 3:267-275.

Xu and Gamst, "Lessons from controversy: Ovarian cancer screening and serum proteomics," *J. Natl. Cancer Inst.*, 2005, 97:1226.

Yamamoto et al., "Mutants in the ADP-ribosyltransferase Cleft of Cholera Toxin Lack Diarrheagenicity but Retain Adjuvanticity," *J. Exp. Med.*, 1997, 185(7):1203-1210.

Yu et al., "GPC5 is a possible target for the 13q31-q32 amplification detected in lymphoma cell lines," *J. Hum. Genet.*, 2003, 48:331-335.

Zhang et al., "Three biomarkers identified from serum proteomic analysis for the detection of early stage ovarian cancer," *Cancer Res.*, 2004, 64:5882-5890.

Zhou et al., "An investigation into the human serum 'interactome'," *Electrophoresis*, 2004, 25:1289-1298.

Zou et al., "Dominant expression of a 1.3 Mb human Igκ locus replacing mouse light chain production," *FASEB J.*, 1996, 10:1227-1232.

Botto et al., "Molecular basis of polymorphisms of human complement component C3," J. Exp. Med., 172:1011-17 (1990).

Lopez et al., "A novel, high-throughput workflow for discovery and identification of serum carrier protein-bound peptide biomarker candidates in ovarian cancer samples," Clin. Chem., 53:1067-74 (2007).

NCBI Reference Sequence NP_000055.1, "Complement component 3 precursor [*Homo sapiens*]," Dec. 4, 2005.

* cited by examiner

BIOMARKERS FOR DETECTING CANCER

CROSS-REFERENCE TO RELATED APPLICATIONS

This application claims priority under 35 U.S.C. §119 to U.S. Application Ser. No. 60/868,400, filed Dec. 4, 2006, the entire contents of which are hereby incorporated by reference.

BACKGROUND

Ovarian cancer is the fourth leading cause of cancer related deaths among women in the United States. Unfortunately, 70-75% of new diagnoses will be Stage III or IV with a predicted 5-year survival of about 15%. This survival rate has remained essentially unchanged over the past 40 years despite the advent of intensive radical surgical approaches and new therapeutic interventions. In contrast, if cancer is detected when confined to the ovary (Stage I), the 5-year survival approaches 90%, requires less radical operations, and may not require adjuvant chemotherapy. More sensitive and specific tests for earlier detection would greatly improve patient survival rates by facilitating early treatments such as surgical intervention.

SUMMARY

The disclosure relates to, inter alia, a variety of biomarkers (e.g., biomarker peptides) and the use of these biomarkers for detecting the health state of a subject. For example, the biomarkers can be used in methods for detecting an ovarian cancer in a subject. As a proper and timely diagnosis of a cancer in a subject can aid a medical practitioner in selecting a therapy for, and/or administering a therapy (e.g., a therapy comprising an anti-cancer agent) to, a subject, the disclosure also features methods for selecting and administering a therapy.

In one aspect, the disclosure features a method for detecting an ovarian cancer in a subject. The method includes the steps of: detecting one or both of the presence and amount of one or more biomarkers in a biological sample from a subject, wherein at least one of the biomarkers is a peptide selected from any of the peptides depicted in Tables 6, 8, 9, and SEQ ID NO:1, and wherein one or both of the presence and amount of the biomarker peptide in the biological sample indicates that the subject has an ovarian cancer. The method can also include the step of obtaining the biological sample from the subject. The biological sample can contain, e.g., urine, blood, plasma, serum, saliva, semen, sputum, cerebral spinal fluid, tears, or mucus. The subject can be, e.g., a mammal such as a human. The detecting can comprise, e.g., mass spectrometry or any other detection method described herein.

In some embodiments, an amount of the biomarker peptide in the biological sample that is similar to an ovarian cancer-positive reference amount of the biomarker peptide indicates that the subject has an ovarian cancer.

In some embodiments, a difference in the amount of the biomarker peptide in the biological sample as compared to a non-ovarian cancer reference amount of the biomarker peptide indicates that the subject has an ovarian cancer. For example, an increase (e.g., a one-fold, a two-fold, a three-fold, a four-fold, a five-fold, a six-fold, a seven-fold, an eight-fold, a nine-fold, or a ten-fold or more increase) in the amount of a biomarker peptide in the biological sample as compared to the non-ovarian cancer reference amount of the biomarker peptide can indicate that the subject has an ovarian cancer. That is, the amount of the biomarker peptide in the biological sample can be at least one fold (e.g., a two-fold, a three-fold, a four-fold, a five-fold, a six-fold, a seven-fold, an eight-fold, a nine-fold, or a ten-fold or more) higher than the non-ovarian cancer reference amount of the biomarker peptide. In another example, a decrease (e.g., a one-fold, a two-fold, a three-fold, a four-fold, a five-fold, a six-fold, a seven-fold, an eight-fold, a nine-fold, or a ten-fold or more decrease) in the amount of a biomarker peptide in the biological sample as compared to the non-ovarian cancer reference amount of the biomarker peptide can indicate that the subject has an ovarian cancer. That is, the amount of the biomarker peptide in the biological sample can be at least one fold (e.g., a two-fold, a three-fold, a four-fold, a five-fold, a six-fold, a seven-fold, an eight-fold, a nine-fold, or a ten-fold or more) lower than the non-ovarian cancer reference amount of the biomarker peptide.

In some embodiments, one or both of the presence and amount of the biomarker peptide in the biological sample can indicate that the subject has an ovarian cancer of a type selected from the group consisting of a serous cystoma, a mucinous cystoma, an endometroid tumor, and a clear cell tumor.

In some embodiments, one or both of the presence and amount of the biomarker peptide in the biological sample can indicate that the subject has an ovarian cancer at a stage selected from the group consisting of Stage I, Stage IA, Stage IB, Stage IC, Stage II, Stage IIA, Stage IIB, Stage IIC, Stage III, Stage IIIA, Stage IIIB, Stage IIIC, and Stage IV.

In some embodiments, the non-ovarian cancer reference amount of the biomarker peptide is the amount of the biomarker peptide in a biological sample from a subject that does not have an ovarian cancer. In some embodiments, the non-ovarian cancer reference amount of the biomarker peptide can be the amount of the biomarker peptide in a biological sample comprising a non-ovarian cancer reference amount of CA125.

In some embodiments, the one or more biomarkers can comprise at least four of the biomarker peptides. The at least four biomarker peptides can be selected from the group consisting of SEQ ID NOS: 8 and 15.

In some embodiments, the one or more biomarkers can comprise at least five of the biomarker peptides. The at least five biomarker peptides can be selected from the group consisting of SEQ ID NOS: 2, 3, 4, 5, and 6.

In some embodiments, the one or more biomarkers can comprise at least seven of the biomarker peptides. The at least seven biomarker peptides can be selected from the group consisting of SEQ ID NOS: 8, 15, 2, 3, 4, 5, and 6.

In some embodiments, the one or more biomarkers can comprise at least nine of the biomarker peptides. The at least nine biomarker peptides can be selected from the group consisting of SEQ ID NOS: 9, 8, 12, 10, 11, 15, 22, 13, and 20.

In some embodiments, the methods can also include the step of detecting one or both of the presence and amount of CA125 in the biological sample.

In some embodiments, the methods can include the step of creating a record. For example, a record can be created that indicates one or both of the presence and amount of the one or more biomarkers in the biological sample. A record can be created that indicates that the subject should undergo one or more additional diagnostic tests (e.g., a biopsy or any other additional diagnostic tests described herein or known in the art) to detect an ovarian cancer if the amount of the biomarker peptide in the biological sample is similar to the ovarian cancer-positive reference amount of the biomarker peptide. A record can be created that indicates that the subject has an ovarian cancer if the amount of the biomarker peptide in the biological sample is similar to the ovarian cancer-positive reference amount of the biomarker peptide. A record can be created that indicates that the subject should undergo one or more additional diagnostic tests (e.g., a biopsy or any other additional diagnostic tests described herein or known in the art) to detect an ovarian cancer if the amount of the biomarker peptide is different than the non-ovarian cancer reference amount of the biomarker peptide. A record can be created that indicates that the subject has an ovarian cancer if the amount of the biomarker peptide is different than the non-ovarian cancer reference amount of the biomarker peptide. Any of the records can be on a tangible medium (such as a written or printed document) or a computer readable medium (e.g., a CD, a DVD, a flashdrive, or a floppy disk).

In some embodiments, the methods can also include the step of: (i) selecting for the subject a therapy comprising an anti-cancer agent if the amount of the biomarker peptide is similar to the ovarian cancer-positive reference amount of the biomarker peptide; or (ii) selecting for the subject a therapy comprising an anti-cancer agent if the amount of the biomarker peptide is different than the non-ovarian cancer reference amount of the biomarker peptide.

In some embodiments, the methods can include the step of: (i) administering to the subject a therapy comprising an anti-cancer agent if the amount of the biomarker peptide is similar to the ovarian cancer-positive reference amount of the biomarker peptide; or (ii) administering to the subject a therapy comprising an anti-cancer agent if the amount of the biomarker peptide is different than the non-ovarian cancer reference amount of the biomarker peptide.

In another aspect, the disclosure features a method for detecting an ovarian cancer in a subject, which method includes the step of measuring the amount of at least four biomarkers in a biological sample from a subject, wherein the biomarkers comprise SEQ ID NOS: 8 and 15, and wherein one or both of a decrease in the amount of SEQ ID NO: 8 and an increase in the amount of SEQ ID NOS: 15, in the biological sample as compared to a non-ovarian cancer reference amount of the biomarkers indicates that the subject has an ovarian cancer.

In another aspect, the disclosure features a method for detecting an ovarian cancer in a subject. The method includes the step of measuring the amount of at least live biomarkers in a biological sample from a subject, wherein the biomarkers comprise SEQ ID NOS: 2, 3, 4, 5, and 6, and wherein one or both of a decrease in the amount of SEQ ID NO: 2 and 4, and an increase in the amount of SEQ ID NOS: 3, 5, and 6, in the biological sample as compared to a non-ovarian cancer reference amount of the biomarkers indicates that the subject has an ovarian cancer.

In another aspect, the disclosure features a method for detecting an ovarian cancer in a subject. The method includes the step of measuring the amount of at least seven biomarkers in a biological sample from a subject, wherein the biomarkers comprise SEQ ID NOS: 8, 15, 2, 3, 4, 5, and 6, and wherein one or both of a decrease in the amount of SEQ ID NOS: 8, 2, and 4, and an increase in the amount of SEQ ID NOS: 15, 3, 5, and 6, in the biological sample as compared to a non-ovarian cancer reference amount of the biomarkers indicates that the subject has an ovarian cancer.

In yet another aspect, the disclosure features a method for detecting an ovarian cancer in a subject. The method includes the step of measuring the amount of at least nine biomarkers in a biological sample from a subject, wherein the biomarkers comprise SEQ ID NOS: 9, 8, 12, 10, 11, 15, 22, 13, and 20, and wherein one or both of a decrease in the amount of SEQ ID NOS: 9, 8, 12, and 10, and an increase in the amount of SEQ ID NOS: 15, 22, and 20, in the biological sample as compared to a non-ovarian cancer reference amount of the biomarkers indicates that the subject has an ovarian cancer.

In another aspect, the disclosure features a method for detecting an ovarian cancer in a subject. The method includes the step of measuring the amount of at least four biomarkers in a biological sample from a subject using mass spectrometry, wherein the biomarkers comprise peptides having a mass-to-charge ratio (m/z) signal at about m/z 1739.93, 2582.35, 2659.27, and 2989.49, and wherein one or both of a decrease in the amount of the signal at m/z 1739.93 and an increase in the amount of signal at m/z 2582.35, 2659.27, and 2989.49 in the biological sample as compared to a non-ovarian cancer reference amount of the signals indicates that the subject has an ovarian cancer.

In another aspect, the disclosure features a method for detecting an ovarian cancer in a subject. The method includes the step of measuring the amount of at least live biomarkers in a biological sample from a subject using mass spectroscopy, wherein the biomarkers comprise peptides having amass-to-charge ratio (m/z) signal at about m/z 1966.91; 1041.68; 2115.05; 1224.68; and 2345.19, and wherein one or both of a decrease in the amount of signal at about m/z 1966.91 and 2115.05 and an increase in the amount of signal at about of m/z 1041.68; 1224.68; and 2345.19 in the biological sample as compared to a non-ovarian cancer reference amount of the signals indicates that the subject has an ovarian cancer.

In another aspect, the disclosure features a method for detecting an ovarian cancer in a subject. The method includes the step of measuring the amount of at least seven biomarkers in a biological sample from a subject using mass spectroscopy, wherein the biomarkers comprise peptides having a mass-to-charge ratio (m/z) signal at about m/z 1739.93; 2582.35; 1966.91; 1041.68; 2115.05; 1224.68; and 2345.19, and wherein one or both of a decrease in the amount of signal at about m/z 1739.93; 1966.91; and 2115.05 and an increase in the amount of signal at about m/z 2582.35, 1041.68; 1224.68; and 2345.19 in the biological sample as compared to a non-ovarian cancer reference amount of the signals indicates that the subject has an ovarian cancer.

In yet another aspect, the disclosure features a method for detecting an ovarian cancer in a subject. The method includes the step of measuring the amount of at least nine biomarkers in a biological sample from a subject using mass spectroscopy, wherein the biomarkers comprise peptides having amass-to-charge ratio (m/z) signal at about m/z 1690.94; 1739.93; 1777.97; 1865.01; 2021.11; 2582.35; 2898.54; 3027.57; and 3239.55, and wherein one or both of a decrease in the amount of signal at about m/z 1690.94; 1739.93; 1777.97; and 1865.01 and an increase in the amount of signal at about m/z 2582.35; 2898.54; and 3239.55 in the biological sample as compared to a non-ovarian cancer reference amount of the signals indicates that the subject has an ovarian cancer.

In yet another aspect, the disclosure features a method for detecting an ovarian cancer in a subject. The method includes the step of detecting one or both of the presence and amount of one or more biomarkers in a biological sample from a subject, wherein at least one of the biomarkers is a biomarker selected from the group consisting of P21-activated kinase 7, Brain specific angiogenesis inhibitor 3 (BAI3), a glypican, Granzyme H, CREB-binding protein, NOTCH, hHeadcase, a component of the 26S proteosome, SET binding protein (SEB), and a fragment of any of the foregoing, and wherein one or both of the presence and amount of the biomarker peptide in the biological sample indicates that the subject has an ovarian cancer.

In some embodiments, the presence of one or both of mRNA encoding the biomarker and biomarker protein is detected. In some embodiments, the amount of one or both of mRNA encoding the biomarker and protein is detected.

In another aspect, the disclosure features a method for detecting an ovarian cancer in a subject. The method includes the step of measuring the amount of one or more biomarkers in a biological sample from a subject, wherein at least one of the biomarkers is a biomarker peptide selected from any of the peptides depicted in Tables 6, 8, 9, and SEQ ID NO:1, and wherein an amount of the biomarker peptide that is similar to an ovarian cancer-positive reference amount of the biomarker peptide indicates that the subject has an ovarian cancer.

In another aspect, the disclosure features a method for detecting an ovarian cancer in a subject. The method includes the step of measuring the amount of one or more biomarkers in a biological sample from a subject, wherein at least one of the biomarkers is a biomarker peptide selected from any of the peptides depicted in Tables 6, 8, 9, and SEQ ID NO:1, and wherein a difference in the amount of the biomarker peptide as compared to a non-ovarian cancer reference amount of the biomarker peptide indicates that the subject has an ovarian cancer.

In yet another aspect, the disclosure features a method for treating an ovarian cancer. The method includes the step of administering to a subject a therapy comprising an effective amount of an anti-cancer agent if a biological sample from the subject has been determined to comprise an amount of a biomarker peptide that is similar to an ovarian cancer-positive reference amount of the biomarker peptide, wherein the biomarker peptide is selected from any of the peptides depicted in Tables 6, 8, 9, and SEQ ID NO:1.

In another aspect, the disclosure features a method for treating an ovarian cancer, the method comprising: administering to a subject a therapy comprising an effective amount of an anti-cancer agent if a biological sample from the subject has been determined to comprise an amount of a biomarker peptide that is different than a non-ovarian cancer reference amount of the biomarker peptide, wherein the biomarker peptide is selected from any of the peptides depicted in Tables 6, 8, 9, and SEQ ID NO:1.

In some embodiments, the above methods can include the steps of (i) measuring the amount of the biomarker peptide in the biological sample from the subject and/or obtaining the biological sample from the subject.

In another aspect, the disclosure provides a method for selecting a therapy for a subject, which method includes the step of selecting for a subject a therapy comprising an anti-cancer agent if a biological sample from the subject has been determined to comprise an amount of a biomarker peptide that is similar to an ovarian cancer-positive reference amount of the biomarker peptide, wherein the biomarker peptide is selected from any of the peptides depicted in Tables 6, 8, 9, and SEQ ID NO:1.

In some embodiments, the methods can include the step of determining whether the biological sample contains an amount of a biomarker peptide that is similar to an ovarian cancer-positive reference amount of the biomarker peptide, wherein the biomarker peptide is selected from any of the peptides depicted in Tables 6, 8, 9, and SEQ ID NO:1.

In yet another aspect, the disclosure provides a method for selecting a therapy for a subject. The method includes the step of selecting for a subject a therapy comprising an anti-cancer agent if a biological sample from the subject has been determined to comprise an amount of a biomarker peptide that is different than a non-ovarian cancer reference amount of the biomarker peptide, wherein the biomarker peptide is selected from any of the peptides depicted in Tables 6, 8, 9, and SEQ ID NO:1.

In some embodiments, the method can also include the step of determining whether a biological sample from the subject comprises an amount of a biomarker peptide that is different than a non-ovarian cancer reference amount of the biomarker peptide.

In some embodiments, any of the above methods can include the steps of (i) administering to the subject an effective amount of the anti-cancer agent and/or (ii) obtaining the biological sample from the subject.

In yet another aspect, the disclosure features a method for generating a biomarker profile for a subject, which method includes the steps of: detecting one or both of the presence and amount of one or more biomarkers in a biological sample from a subject, wherein at least one of the biomarkers is selected from any of the peptides depicted in Tables 6, 8, 9, and SEQ ID NO:1; and creating a record (e.g., a record on a tangible or computer readable medium) indicating one or both of the presence and amount of the one or more biomarkers in the biological sample to thereby generate a biomarker profile for the subject.

In another aspect the disclosure features a biomarker profile generated by the above method. The biomarker profile can be recorded on, e.g., a tangible or a computer readable medium.

In yet another aspect, the disclosure features a method for identifying an ovarian cancer biomarker peptide. The method includes the steps of: providing a biological sample from a subject having an ovarian cancer; concentrating peptides bound to carrier proteins in the biological sample; separating one or more of the peptides from the carrier proteins; and subjecting the separated peptides to mass spectrometry to thereby identify at least one of the separated peptides, wherein one or both of the presence and amount of the at least one identified peptide indicates that the peptide is an ovarian cancer biomarker peptide. The mass spectrometry can include one or both of high resolution matrix assisted laser desorption/ionization orthogonal time-of-flight (MALDI-O-TOF) mass spectrometry and tandem mass spectrometry sequencing.

In some embodiments, an amount of the at least one identified peptide that is similar to an amount of the peptide in an ovarian cancer-positive reference sample indicates that the identified peptide is an ovarian cancer biomarker peptide.

In some embodiments, a difference in the amount of the at least one identified peptide as compared to the amount of the peptide in a non-ovarian cancer reference sample that the identified peptide is an ovarian cancer biomarker peptide.

In some embodiments, the methods can further comprise obtaining a biological sample from a subject.

In some embodiments, the methods can include the step of, prior to subjecting the separated peptides to mass spectrometry, concentrating the separated peptides.

In another aspect, the disclosure provides a kit for detecting a biomarker. The kit can include: one or more biomarker peptides selected from any of the peptides depicted in Tables 6, 8, 9, and SEQ ID NO:1, wherein the one or more biomarker peptides comprise at least one heavy atom isotope; and, optionally, instructions for how to detect the one or more biomarker peptides using mass spectrometry. The kit can also include, e.g., one or more reagents for isolating a peptide from a biological sample; a CA125 polypeptide (e.g., as a control) or a CA125 polypeptide comprising at least one heavy isotope atom; and/or a Matrix-Assisted Laser Desorption Ionization (MALDI) target plate.

In yet another aspect, the disclosure features a composition comprising: a first component consisting of an amino acid sequence selected from any of the peptides depicted in Tables 6, 8, 9, and SEQ ID NO:1, or a fragment of the amino acid sequence having at least 7 contiguous amino acids; and a second component comprising a detectable label. The detectable label can be, e.g., a heterologous amino acid sequence, an enzymatic label, a fluorescent label, a luminescent label, or a radionuclide.

In another aspect, the disclosure features an isolated biomarker peptide consisting of an amino acid sequence selected from any of the biomarker peptides depicted in Tables 6, 8, 9, and SEQ ID NO:1, or a fragment of the amino acid sequence having at least 7 (e.g., (e.g., 8, 9, 10, 11, 12, 13, 14, 15, 20, 25, 30, or 35 or more) contiguous amino acids.

In another aspect, the disclosure features an isolated biomarker peptide consisting of, or consisting essentially of, an amino acid sequence that is at least 65% (e.g., at least 70%, at least 75%, at least 80%, at least 85%, at least 90%, at least 95%, at least 97%, or 100%) identical to a peptide sequence depicted in any of Tables 6, 8, 9, and SEQ ID NO:1.

In another aspect, the disclosure features an isolated biomarker peptide consisting of, or consisting essentially of, an amino acid sequence of peptide sequence depicted in any of Tables 6, 8, 9, and SEQ ID NO:1, but with not more than 20 (e.g., not more than 19, not more than 18, not more than 17, not more than 16, not more than 15, not more than 14, not more than 13, not more than 12, not more than 11, not more than 10, not more than nine, not more than eight, not more than seven, not more than six, not more than five, not more than four, not more than three, not more than two, or not more than 1) substitutions. The substitutions can be, e.g., conservative or non-conservative.

In another aspect, the disclosure features: (i) an isolated nucleic acid encoding any of the biomarker peptides or any of the peptide-based compositions described herein; (ii) a vector comprising the isolated nucleic acid (e.g., a vector wherein the nucleic acid is operably linked to an expression control sequence); (iii) a cell comprising the vector; and (iv) methods for producing the biomarker peptide from the cell or the medium in which the cell is cultured. In some embodiments, the isolated nucleic acid can be detectably labeled, e.g., radiolabeled with any of the radioisotopes described herein.

In yet another aspect, the disclosure features an isolated antibody or antigen-binding fragment thereof that selectively binds to an amino acid sequence selected from any of the biomarker peptides depicted in Tables 6, 8, 9, and SEQ ID NO:1. The antibody can be a monoclonal antibody, a polyclonal antibody, a humanized antibody, a fully human antibody, a single chain antibody, a chimeric antibody, an Fab fragment, an F(ab')2 fragment, an Fab' fragment, an Fv fragment, or an scFv fragment.

In another aspect, the disclosure features a kit for detecting a biomarker. The kit includes: at least one of the above antibodies; and, optionally, instructions for how to detect a biomarker peptide using the antibody.

In yet another aspect, the disclosure features an article of manufacture comprising: a container; and a composition contained within the container, wherein the composition comprises an active agent for treating an ovarian cancer in a subject and wherein the container has a label indicating that the composition is for use in treating an ovarian cancer in a subject if one or both of: (i) a biological sample obtained from the subject contains an amount of a biomarker peptide that is similar to an ovarian cancer-positive reference amount of the biomarker peptide, wherein the biomarker peptide is selected from any of the peptides depicted in Tables 6, 8, 9, and SEQ ID NO:1; and (ii) a biological sample obtained from the subject contains an amount of a biomarker peptide that is different than a non-ovarian cancer reference amount of the biomarker peptide, wherein the biomarker peptide is selected from any of the peptides depicted in Tables 6, 8, 9, and SEQ ID NO:1. The article of manufacture can also include instructions for administering the active agent to the subject.

In another aspect, the disclosure features an array comprising at least two (e.g., at least three, at least four, at least five, at least six, at least seven, at least eight, at least nine, at least 10, at least 11, at least 12, at least 15, at least 20, at least 25, at least 30, at least 35, at least 40, at least 45, or at least 50 or more) binding agents, each binding agent preferentially binding to a different biomarker peptide depicted in any of Tables 6, 8, 9, and SEQ ID NO:1 and/or P21-activated kinase 7, Brain specific angiogenesis inhibitor 3 (BAI3), a glypican, Granzyme H, CREB-binding protein, NOTCH, hHeadcase, a component of the 26S proteosome, SET binding protein (SEB), and a fragment of any of the foregoing (e.g., a fragment of any of the foregoing having at least 7 (e.g., 8, 9, 10, 11, 12, 13, 14, 15, 20, 25, 30, or 35 or more) contiguous amino acids). At least one of the binding agents can be, e.g., an antibody or antigen binding fragment thereof.

In some embodiments, the arrays can have less than 100,000 (e.g., less than 90,000; less than 80,000; less than 70,000; less than 60,000; less than 50,000; less than 40,000; less than 30,000; less than 20,000; less than 15,000; less than 10,000; less than 5,000; less than 4,000; less than 3,000; less than 2,000; less than 1,500; less than 1,000; less than 750; less than 500, less than 200, less than 100, or less than 50) different binding agents.

In some embodiments, the binding agents can be bound to a solid support. The solid support can be, e.g., a protein chip or any other support described herein or known in the art. In some embodiments, each of the binding agents is bound to a different solid support such a different particle (or a differently encoded particle), magnetic particles, or combinations thereof.

In yet another aspect, the disclosure provides a kit containing one or more of the above arrays; and one or more reagents (e.g., a cross-linking agent or a detectable label) for detectably labeling a biomarker peptide.

Many mass spectrometers have mass accuracies to high resolution. For example, in the case of a singly charged ion, this range corresponds to 0.6 m/z. Accordingly, such ranges can be used herein. For example, the selection of ions having a mass-to-charge ratio (m/z) of about 3027.57 can be implemented by using a channel that ranges from 3027.51 to 3027.63. Minor variations (e.g., variations in the calibration) in a mass spectrometer may result in ion m/z signals that do not coincide with the ones stated herein, but the m/z signal corresponding to those disclosed can be easily identified and used, e.g., by compensating for offset in calibration.

Other features and advantages of the disclosure will be apparent from the following description, from the drawings, and from the claims.

DETAILED DESCRIPTION

Figure 1:
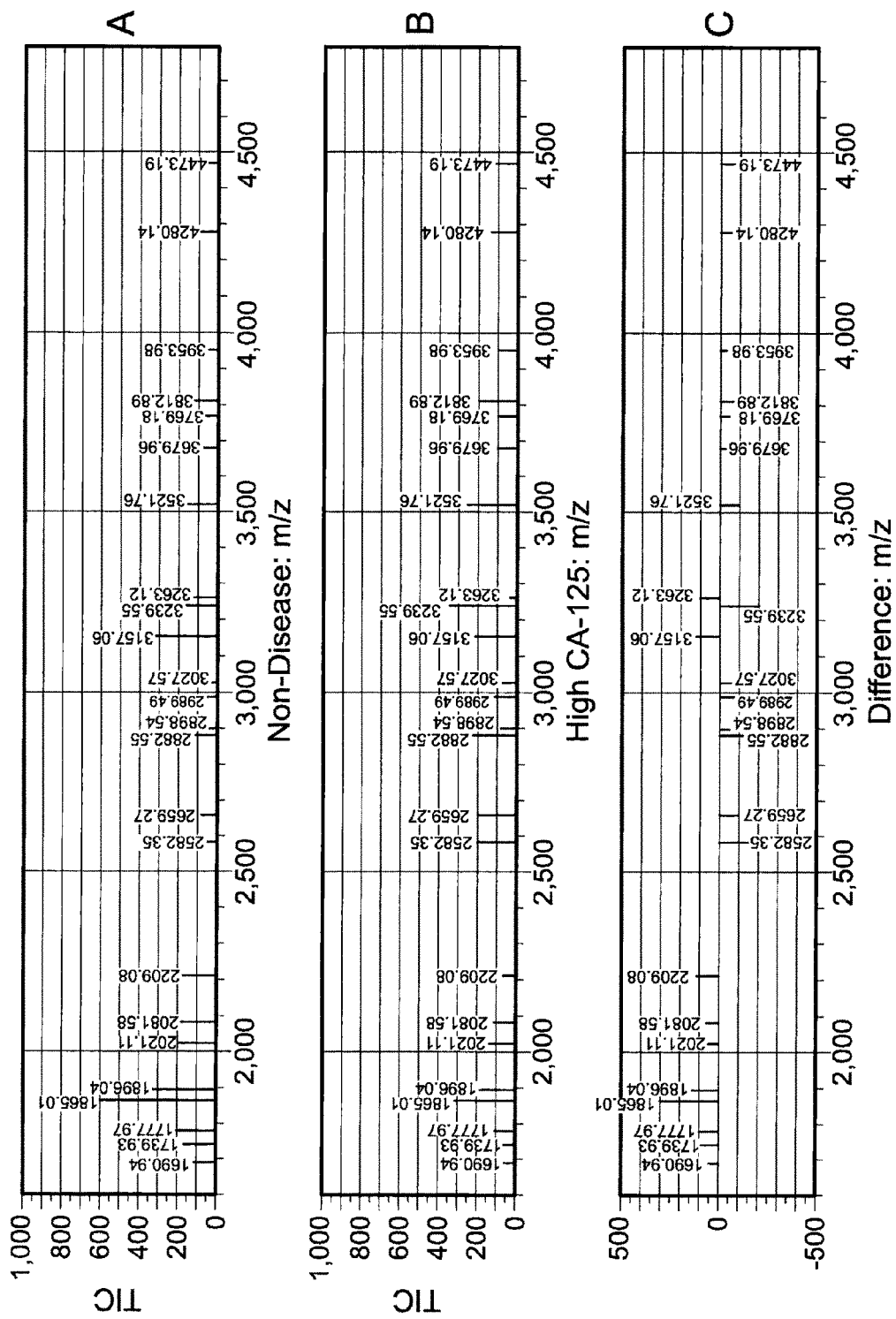
FIG. 1 shows mass spectrographs for peptides isolated from (A) normal serum samples and (B) serum samples corresponding to high CA-125 levels. Also shown is a (C) difference spectrum based on (A) and (B).

The disclosure features, inter alia, a variety of biomarkers (e.g., biomarker peptides), compositions, and kits for use in methods for diagnosing a cancer. For example, the biomarkers can be used in methods for detecting an ovarian cancer in a subject. The biomarkers can also be used to, e.g., generate a biomarker profile for a subject (or cohort of subjects), and aid in selecting a therapy for, and/or administering a therapy (e.g., a therapy comprising an anti-cancer agent) to, a subject.

In general terms, biomarkers are biological characteristics that serve as indicators of normal and disease processes occurring in the body. Certain peptides serve as biomarkers in that their presence, or changes in their amounts, correlate with the onset or decline of a bodily process. Such peptides can be found in fluids and tissues throughout the body. Examples of peptides sometimes present in blood include hormones, growth factors, cytokines, and degradation products of proteins. When using peptides as biomarkers, the presence or amount of a biomarker peptide in a biological sample from a subject (e.g., a human patient) can be used to identify the presence, severity, or type of disease; to predict an individual response to therapy such as for maximizing drug efficacy and minimizing risk or severity of adverse events; to predict drug efficacy and risk of on- or off-target adverse events, as well as to predict a likely course of disease progression.

As described in the Example below, several new biomarkers have been identified as useful for distinguishing ovarian cancer patient samples from non-cancer patient samples. The process for identifying these ovarian cancer biomarkers involved isolating peptides from carrier protein-cargo peptide complexes contained in serum samples using: (i) high resolution matrix assisted laser desorption/ionization orthogonal time-of-flight (MALDI OTOF) mass spectrometry for characterizing peptides in ovarian cancer and non-cancer serum based on mass to charge ratios and (ii) MS/MS sequencing for determining the amino acid sequence of selected peptides. More specifically, to develop a "top down" workflow for biomarker identification, high-throughput carrier protein-bound affinity enrichment of serum samples was coupled with high resolution MALDI orthogonal time of flight (OTOF) mass spectrometry, discriminate analysis of the resulting mass spectral patterns, and sequence identification of the discriminating ions to search for putative early protein/peptide biomarkers in ovarian cancer serum samples. The carrier protein-based approach yielded a number of sets of discriminating peptides, and flexible discriminant models with multiple marker sets were build. Using these models, cancer and normal samples with were classified with high specificity and sensitivity. Results from these studies indicated that high classification power was provided by peptide fragments associated with the coagulation cascade.

Using methods described herein, it was possible to detect additional previously unidentified cancer biomarkers corresponding to 5 peptides that are not related to either coagulation or inflammation pathways. Among these lower intensity peptides, Casein kinase 2 is oncogenic and upregulated in tumors (38) and trangelin has been reported previously as a putative marker for ovarian and endometrial cancer in other studies using widely different discovery methods including LC-MS and cDNA-RDA (39, 40). The other three, keratin 2, glycosyl transferase (LARGE) and diamino oxidase are also associated with processes related to cancer (41-43). In addition, several fragments, many from low abundance proteins or proteins not previously seen in serum, were recovered from the ovarian cancer sera. In particular, a number of proteins associated with cellular proliferation, cancer, and cancer signaling pathways in the ovarian cancer samples. Many of the peptides were not found in the pooled healthy serum samples.

The Example below describes a study that involved analyzing 110 normal serum samples and 453 ovarian cancer serum samples, which had been characterized as having low CA-125 (below 22 ng/ml, 239 samples) and high CA-125 (above 22 ng/ml, 214 samples), and revealed that several peptides were present at higher or lower levels in normal serum in comparison to ovarian cancer serum.

Several biomarkers for ovarian cancer were identified by peptide sequences as presented in Tables 6, 8 and 9. Briefly the ovarian cancer biomarkers included:

a) P21-activated kinase 7 is a member of the PAK family of Ser/Thr protein kinases. PAK family members are known to be effectors of Rac/Cdc42 GTPases, which have been implicated in the regulation of cytoskeletal dynamics, proliferation, and cell survival signaling (47). Pak1 overexpression and hyperactivation have been linked with the invasiveness of human breast cancer cells and breast tumors. Expression of Pak1 in breast tumor tissue correlates with tumor grade showing higher expression in less differentiated ductal carcinomas of the breast (grade 3 tumors) than in grade 2 and grade 1 tumors (47).

b) Brain-specific angiogenesis inhibitor 3 (BAI3) is an angiogenesis inhibitor that is a candidate for involvement in the development of glioblastoma (48).

c) The glypicans compose a family of glycosylphosphatidylinositol-anchored heparan sulfate proteoglycans that may play a role in the control of cell division and growth regulation (49) Glypican 5 (GPC5) was over-expressed in lymphoma cell lines that had shown amplification, in comparison with those that had not. The findings suggested that GPC5 is a likely target for amplification, and that over-expression of this gene may contribute to development and/or progression of lymphomas and other tumors (49).

d) The 26S proteasome, consisting of the 20S core and 19S regulatory complexes, regulates intracellular protein concentration through proteolytic degradation of targeted substrates. Aberrant activity of the 26S proteasome affects the cell cycle, apoptosis and other cellular processes related to cancer (51, 52). TBP-1 is a component of the 19 S regulatory subunit of the proteasome 26 S. DNA homology suggests that an apparent part of TBP-1 has been obtained as a BRCA1 locus-related gene (OV-4) and mapped onto chromosome 17q12-21. Interestingly, the nucleotide structure of human TBP-1 is very similar to that of the GT198 gene, which has been cloned from a human breast cancer cell line and also mapped onto the BRCA1 locus (53). TBP-1 specifically interacts with ARF, a tumor suppressor and a key regulator of cellular proliferation that is frequently inactivated in human cancer. Overexpression of TBP-1 in various cell lines results in a sharp increase of ARF protein levels and this overexpression results in an increase in p53 protein levels and activity underlining a clear involvement of TBP-1 in the control of cell proliferation (52).

e) Granzyme H is a member of the granzyme family of serine proteases stored in the cytoplasmic granules of CTLs, NK and LAK cells. These molecules are involved in cytotoxic T lymphocyte (CTL), natural killer (NK) and lymphokine activated killer (LAK) cell-mediated lysis (54). Granzyme H plays a role in complementing the pro-apoptotic function of granzyme B in human NK cells (55).

f) CREB-binding protein interacts with coactivator p300 and the breast cancer susceptibility gene BRCA1 to activate target gene transcription (56).

g) Specific cell fate decision during development is regulated by NOTCH-ligand interaction. Studies indicate that NOTCH activation plays a role in the onset and progression of many human malignancies, in addition to its functions in developmental and cell maturation processes (57).

h) The Headcase (hHDC) gene may play an important role in some human cancers as a tumor suppressor. The hHDC gene was isolated from 6q24, a commonly deleted region on chromosome 6. Deletions from the long arm of chromosome 6 are one of the most common chromosomal abnormalities in multiple human malignancies, including pancreatic cancer (58).

i) The SET binding protein (SEB) gene is located on chromosome 18q21.1 that contains candidate tumor suppressor genes associated with deletions in cancer and leukemia. Although the function of SEB is not known, it has been speculated that SEB plays a key role in the mechanism of SET-related leukemogenesis and tumorigenesis (59).

j) Several proteins identified in this study, such as Transthyretin, have also been reported by others as putative biomarkers for ovarian cancer (10, 60). Interestingly, the transthyretin fragment reported herein is a different unique mass than that reported in a previous serum based ovarian cancer study (10).

Taken together, these represent a remarkable collection of proteins involved in cellular inflammation, differentiation, signaling, apoptosis, transcriptional regulation and other regulatory mechanisms. It is remarkable that this rich variety of low abundance species are so well represented in the fraction bound to serum albumin.

In these studies, more than 160 ovarian cancer biomarker peptides were identified from among the peptides and protein fragments bound to carrier proteins from ovarian cancer patient serum samples (see, e.g., Tables 6, 8, 9, and SEQ ID NO:1). Three sets of the discriminating carrier-protein bound fragments differentiated the ovarian cancer and the non-cancer reference samples with sensitivities and specificities of up to 93% and 97% respectively. These figures compare very favorably with published average sensitivities and specificities of about 50% for CA125, the current standard biomarker for ovarian cancer.

Biomarker Peptides

The disclosure features biomarker peptides comprising an amino acid sequence that is at least 65% (e.g., at least 70%, at least 75%, at least 80%, at least 85%, at least 90%, at least 95%, at least 97%, or 100%) identical to a peptide sequence depicted in any of Tables 6, 8, 9, and SEQ ID NO:1. In some embodiments, a biomarker peptide can consist of, or consist essentially of, an amino acid sequence that is at least 65% (e.g., at least 70%, at least 75%, at least 80%, at least 85%, at least 90%, at least 95%, at least 97%, or 100%) identical to a peptide sequence depicted in any of Tables 6, 8, 9, and SEQ ID NO:1.

Percent identity between two peptide sequences (e.g., a peptide of any of Tables 6, 8, 9, and SEQ ID NO:1, and another amino acid sequence that may be at least 65% identical to the peptide) can be determined using a variety of algorithms and computer programs including, but not limited to, Clustal W (The European Bioinformatics Institute (EMBL-EBI), BLAST-Protein (National Center for Biotechnology Information (NCBI), United States National Institutes of Health), and PSAlign (University of Texas A&M; Sze et al. (2006) Journal of Computational Biology 13:309-319).

The disclosure also features biomarker peptides comprising an amino acid sequence of a peptide sequence depicted in any of Tables 6, 8, 9, and SEQ ID NO:1, but with not more than 20 (e.g., not more than 19, not more than 18, not more than 17, not more than 16, not more than 15, not more than 14, not more than 13, not more than 12, not more than 11, not more than 10, not more than nine, not more than eight, not more than seven, not more than six, not more than five, not more than four, not more than three, not more than two, or not more than 1) substitutions. The substitutions can be, e.g., conservative or non-conservative (as described below). In some embodiments, a biomarker peptide can consist of, or consist essentially of, an amino acid sequence of a peptide sequence depicted in any of Tables 6, 8, 9, and SEQ ID NO:1, but with not more than 20 substitutions.

Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. Any substitution of one member of the above-mentioned polar, basic or acidic groups by another member of the same group can be deemed a conservative substitution. By contrast, a non-conservative substitution is a substitution of one amino acid for another with dissimilar characteristics.

Also featured are peptide-based compositions comprising: a first component consisting of an amino acid sequence selected from any of the peptides depicted in Tables 6, 8, 9, and SEQ ID NO:1, or a fragment of the amino acid sequence having at least 7 (e.g., 8, 9, 10, 11, 12, 13, 14, 15, 20, 25, 30, or 35 or more) contiguous amino acids; and second component comprising a detectable label. The first component can be an amino acid with not more than 20 substitutions (conservative or non-conservative substitutions) or can be at least about 65% identical to an amino acid sequence of peptide sequence depicted in any of Tables 6, 8, 9, and SEQ ID NO:1. The detectable label can be selected one from the group consisting of an amino acid sequence that is heterologous to the biomarker peptide sequence; an enzymatic label, a fluorescent label, a luminescent label, and a radionuclide (see below).

An amino acid sequence that is "heterologous" to a peptide sequence depicted in any of Tables 6, 8, 9, and SEQ ID NO:1, or the term "heterologous amino acid" sequence, is an amino acid sequence other than amino acid sequences immediately flanking a peptide sequence depicted in any of Tables 6, 8, 9, and SEQ ID NO:1, in nature. For example, two or more (e.g., two, three, four, five, six, seven, eight, nine, 10, 11, 12, 13, 14, 15, 16, 17, 18, 19, or 20 or more) or less than 20 (e.g., 19, 18, 17, 16, 15, 14, 13, 12, 11, 10, nine, eight, seven, six, five, four, three, two, or one) carboxy- and/or amino-terminal amino acid(s) immediately flanking SSKITHRIHWESASLLR (SEQ ID NO:1) in Complement Component II Precursor (NCBI Accession No. NP_000055) are not considered to be heterologous to SEQ ID NO:1. It is understood that a peptide containing a first component consisting of an amino acid sequence that is less than 100% identical to, or contains from one to four conservative substitutes in, an amino acid sequence of a peptide sequence depicted in any of Tables 6, 8, 9, and SEQ ID NO:1, may not occur in nature at all.

A heterologous sequence can be, for example a sequence used for purification of the recombinant protein (e.g., FLAG, polyhistidine (e.g., hexahistidine), hemagluttanin (HA), glutathione-S-transferase (GST), or maltose-binding protein (MBP)). Heterologous sequences can also be proteins useful as diagnostic or detectable markers, for example, luciferase, green fluorescent protein (GFP), or chloramphenicol acetyl transferase (CAT). In some embodiments, the polypeptide can contain a signal sequence from another protein. In some embodiments, the polypeptide can contain a therapeutic or immune-stimulating polypeptide (e.g., a T helper epitope (e.g., a Tetanus Toxoid universal T helper cell epitope) or all or part of a cytokine or chemokine) and/or a carrier (e.g., KLH) useful, e.g., in eliciting an immune response (e.g., for antibody generation). In some embodiments, the heterologous sequence can contain one or more linker peptides or a targeting polypeptide. Heterologous sequences can be of varying length and in some cases can be a longer sequence than a peptide sequence depicted in any of Tables 6, 8, 9, and SEQ ID NO:1, to which the heterologous sequences are attached.

Targeting polypeptides, as used herein, are polypeptides that target the moiety to which they are attached (e.g., a peptide sequence depicted in any of Tables 6, 8, 9, and SEQ ID NO:1) to specific tissues (e.g., to a lymph node) or cells (e.g., to an antigen presenting cell or other immune cell), or where in vitro, specific isolated molecules or molecular complexes (e.g., a purification resin). Targeting polypeptides can be, e.g., an antibody or antigen binding fragment thereof or a ligand for a cell surface receptor. A ligand for a cell surface receptor can be, e.g., a chemokine, a cytokine (e.g., Interleukins 1, 2, 3, 4, 5, 6, 7, 8, 9, 10, 11, 12, 13, 14, 15, or 16), or a death receptor ligand (e.g., FasL or TNFα).

A linker peptide can connect a biomarker peptide sequence depicted in any of Tables 6, 8, 9, and SEQ ID NO:1, to one or more heterologous amino acid sequences. The linker peptide can contain, or be, at least one (e.g., one, two, three, four, five, six, seven, or eight or more) protease cleavage site(s). The protease sites can be, e.g., a trypsin, a chymotrypin, or a factor Xa cleavage site. Such protease sites can be useful, e.g., to separate a biomarker peptide sequence from a heterologous sequence. For example, after expression and purification of a polypeptide containing a biomarker peptide sequence joined to a polyhistidine sequence (e.g., used for purification) by a trypsin protease cleavage site, the polyhistidine sequence can be removed from the biomarker peptide sequence by contacting the polypeptide with trypsin.

Nucleic Acids and Methods for Producing the Biomarker Peptides

The disclosure also features vectors and nucleic acids encoding, and methods for producing, one or more (e.g., one, two, three, four, five, six, seven, eight, nine, 10, 11, 12, 13, or 14) of any of the biomarker peptides described herein (e.g., one or more of any of the peptides depicted in Tables 6, 8, 9, and SEQ ID NO:1). Methods for producing one or more of any of the polypeptides described herein can include the steps of: optionally, providing a cell (or group of cells) comprising a nucleic acid vector containing a nucleic acid sequence encoding one of more of any of the biomarker peptides described herein, the nucleic acid sequence operably linked to an expression control sequence, and culturing the cell under conditions that permit the expression of the polypeptides. The methods can also include the step of isolating the one or more biomarker peptides from the cell, or from the medium in which the cell was cultured.

Suitable methods for constructing nucleic acids and vectors (e.g., expression vectors) for recombinant expression of one or more of the biomarker peptides described herein are well known to those skilled in the art and described in, e.g., Sambrook et al., Molecular Cloning: A Laboratory Manual Second Edition vol. 1, 2 and 3. Cold Spring Harbor Laboratory Press: Cold Spring Harbor, N.Y., USA, November 1989, the disclosure of which is incorporated by reference in its entirety. The nucleic acids and vectors can be used, e.g., to express the biomarker peptides in a wide variety of host cells including, e.g., a bacterial, a yeast, or a mammalian cell.

The nucleic acids can be operably-linked to promoter and/or enhancer elements that direct the expression of the polypeptides encoded by the nucleic acids. Enhancers provide expression specificity in terms of time, location, and level. Unlike a promoter, an enhancer can function when located at variable distances from the transcription initiation site, provided a promoter is present. An enhancer can also be located downstream of the transcription initiation site. To bring a coding sequence under the control of a promoter, it is necessary to position the translation initiation site of the translational reading frame of the polypeptide between one and about fifty nucleotides downstream (3') of the promoter. Promoters of interest include, but are not limited to, the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3 phosphoglycerate kinase, the promoters of acid phosphatase, and the promoters of the yeast a mating factors, the adenoviral E1b minimal promoter, or the thymidine kinase minimal promoter.

The nucleic acids, or vectors containing the nucleic acids, can contain a leader sequence that encodes a signal peptide. The leader sequence can be at the 5' end of the sequence encoding one or more of the biomarker peptides described herein. The signal peptide can be immediately N-terminal of a given biomarker peptide or can be separated from it by one or more (e.g., 2, 3, 4, 6, 8, 10, 15 or 20) amino acids, provided that the leader sequence is in frame with the nucleic acid sequence encoding the biomarker peptides. The signal peptide, which is generally cleaved from the biomarker peptide prior to secretion, directs the biomarker peptides to which it is attached into the lumen of the host cell endoplasmic reticulum (ER) during translation and the biomarker peptides are then secreted, via secretory vesicles, into the environment of the host cell. Useful signal peptides include, e.g., native leader sequences of cytokines or growth factors, KDEL (SEQ ID NO:45), or any signal sequences described in, e.g., U.S. Pat. No. 5,827,516, the disclosure of which is incorporated herein by reference in its entirety.

In some embodiments, the 5' end of a nucleic acid encoding a biomarker peptide can include a non-native ATG "start sequence." That is, e.g., an ATG sequence can be added to a nucleic acid encoding a polypeptide to ensure that the polypeptide is properly transcribed and translated. Although a leader sequence generally includes an ATG start sequence, in embodiments where it does not, the ATG sequence can be added at the 5' end of a nucleic acid encoding the leader sequence.

A recombinant nucleic acid can be introduced into a cell using a variety of methods, which methods can depend, at least in part, on the type of cell into which the nucleic acid is introduced. For example, bacterial cells can be transformed using methods such as electroporation or heat shock. Methods for transfecting yeast cells include, e.g., the spheroplast technique or the whole-cell lithium chloride yeast transformation method (see, e.g., U.S. Pat. No. 4,929,555; Hinnen et al. (1978) Proc. Nat. Acad. Sci. USA 75:1929; Ito et al. (1983) J. Bacteriol. 153:163; U.S. Pat. No. 4,879,231; and Sreekrishna et al. (1987) Gene 59:115, the disclosures of each of which are incorporated herein by reference in their entirety). Transfection of animal cells can feature, for example, the introduction of a vector to the cells using calcium phosphate, electroporation, heat shock, liposomes, or transfection reagents such as FUGENE® or LIPOFECTAMINE®, or by contacting naked nucleic acid vectors with the cells in solution (see, e.g., Sambrook et al., supra).

Expression systems that can be used for small or large scale production of the biomarker peptides described herein include, but are not limited to, microorganisms such as bacteria (for example, *E. coli* and *B. subtilis*) transformed with recombinant bacteriophage DNA, plasmid DNA, or cosmid DNA expression vectors; yeast (for example, *Saccharomyces* and *Pichia*) transformed with recombinant yeast expression vectors; insect cell systems infected with recombinant virus expression vectors (for example, baculovirus); plant cell systems infected with recombinant virus expression vectors (for example, cauliflower mosaic virus (CaMV) and tobacco mosaic virus (TMV)) or transformed with recombinant plasmid expression vectors (for example, Ti plasmid); or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter, a CMV promoter, an SV40 promoter, or the vaccinia virus 7.5K promoter). Also useful as host cells are primary or secondary cells obtained directly from a mammal, transfected with a plasmid vector or infected with a viral vector (e.g., viral vectors such as herpes viruses, retroviruses, vaccinia viruses, attenuated vaccinia viruses, canary pox viruses, adenoviruses and adeno-associated viruses, among others).

As described above, following the expression of any of the biomarker peptides described herein, the biomarker peptides can be isolated from the cultured cells, or from the media in which the cells were cultured, using standard techniques (see Sambrook et al., supra). Methods of isolating proteins are known in the art and include, e.g., liquid chromatography (e.g., HPLC), affinity chromatography (e.g., metal chelation or immunoaffinity chromatography), ion-exchange chromatography, hydrophobic-interaction chromatography, precipitation, or differential solubilization.

Smaller biomarker peptides (e.g., biomarker peptides having less than 200 (e.g., less than 175, less than 150, less than 125, less than 100, less than 90, less than 80, less than 70, or less than 60) amino acids) can be chemically synthesized by standard chemical means.

In some embodiments, the isolated biomarker peptides can be frozen, lyophilized, or immobilized and stored under appropriate conditions, which allow the biomarker peptides to retain activity (e.g., the ability to be detected by a method described herein and/or to induce an immune response in a subject).

Additional Processing of the Biomarker Peptides

Following the expression or synthesis of any of the biomarker peptides described herein, the biomarker peptides can be further processed. The further processing can include chemical or enzymatic modifications to biomarker peptides or, in cases where the biomarker peptides are modified, the processing can include enzymatic or chemical alterations of existing modifications, or both. Enzymatic treatment can involve contacting a biomarker peptide with, e.g., one or more proteases, phosphatases, or kinases under conditions that allow the polypeptide to be modified.

The processing can include the addition of a detectable label to a biomarker peptide. For example, a biomarker peptide can be detectably labeled with an enzyme (e.g., horseradish peroxidase, alkaline phosphatase, β-galactosidase, or acetylcholinesterase), a fluorescent material (e.g., umbelliferone, fluorescein, fluorescein isothiocyanate, rhodamine, dichlorotriazinylamine, fluorescein, dansyl chloride, allophycocyanin (APC), or phycoerythrin), a luminescent material (e.g., a lanthanide or chelate thereof), a bioluminescent material (e.g., luciferase, luciferin, or aequorin), or a radionuclide (e.g., $^{3}$H, $^{32}$P, $^{33}$P, $^{125}$I, or $^{35}$S).

The additional processing of the biomarker peptides can include the addition (covalent or non-covalent joining) of a heterologous amino acid sequence such as, but not limited to, any of the heterologous amino acid sequences described above. It is understood that as a heterologous sequence can be detected using, e.g., an antibody, heterologous sequences are also "detectable labels."

Arrays and Kits

The disclosure also features arrays and kits for use in any of the methods described herein including, e.g., detecting (and/or measuring) the presence or amount of a biomarker in a biological sample. The arrays and kits are also useful for, e.g., selecting a therapy (e.g., a therapy comprising an anti-cancer agent) for a subject and/or generating a biomarker profile for a subject.

Arrays

The arrays can include at least two (e.g., at least three, at least four, at least five, at least six, at least seven, at least eight, at least nine, at least 10, at least 11, at least 12, at least 15, at least 20, at least 25, at least 30, at least 35, at least 40, at least 45, or at least 50 or more) binding agents, each binding agent preferentially binding to a different biomarker peptide, e.g., any of the biomarker peptides depicted in any of Tables 6, 8, 9, and SEQ ID NO:1 and/or P21-activated kinase 7, Brain specific angiogenesis inhibitor 3 (BAI3), a glypican, Granzyme H, CREB-binding protein, NOTCH, hHeadcase, a component of the 26S proteosome, SET binding protein (SEB), and a fragment of any of the foregoing (e.g., a fragment of any of the foregoing having at least 7 (e.g., 8, 9, 10, 11, 12, 13, 14, 15, 20, 25, 30, or 35 or more) contiguous amino acids).

In some embodiments, the arrays can have less than 100,000 (e.g., less than 90,000; less than 80,000; less than 70,000; less than 60,000; less than 50,000; less than 40,000; less than 30,000; less than 20,000; less than 15,000; less than 10,000; less than 5,000; less than 4,000; less than 3,000; less than 2,000; less than 1,500; less than 1,000; less than 750; less than 500, less than 200, less than 100, or less than 50) different binding agents.

Binding agents include any agent that preferentially binds to the biomarker peptide of interest. For example, the binding agent can be an antibody or biomarker peptide-binding fragment thereof. The binding agent can be a polypeptide or biomarker peptide-binding fragment of the polypeptide that is capable of preferentially binding to the biomarker peptide. For example, the alternative superantigen binding molecule (p85), which was shown to bind to SEB, can be used as a binding agent of the array to detect SEB in a biological sample (Rogers et al. (1995) 7(11):1721-1727). In another example, all or part of coactivator p300 or the breast cancer susceptibility protein BRCA1, both of which bind to CREB-binding protein, can be used as binding agents to detect the presence and/or measure the amount of CREB-binding protein in a biological sample (Crowe et al. (2006) Breast Cancer Res. 8:R1). The binding agent can also be a nucleic acid, such as an aptamer, which preferentially binds to the biomarker peptide or a substrate (e.g., a non-hydrolyzable substrate) of a biomarker peptide. For example, Granzyme H can be captured using the general serine protease inhibitor DCI or the phosphonate inhibitor FTC-Aca-Phe-Leu-Phe(P)(OPh)$_2$ (Edwards et al. (1999) J Biol. Chem. 274(43):30468-30473).

Methods for determining whether a molecule can be used as a binding agent for a particular biomarker peptide are known in the art. A variety of commercial kits can be obtained and employed to detect interactions between a biomarker peptide and a candidate binding agent. For example, fluorescence resonance energy transfer (FRET) or time resolved-FRET (TR-FRET) immunoassay kits (e.g., LANCE® and DELFIA® kits) are available from PerkinElmer (Boston, Mass.).

The arrays can be attached to a solid support. A solid support can have a variety of physical formats, which can include for example, a membrane; a chip (e.g., a protein chip); a slide (e.g., a glass slide or coverslip); a column; a hollow, solid, semi-solid, pore or cavity containing particle such as a bead; a gel; a fiber including a fiber optic material; a matrix; and a sample receptacle. Non-limiting examples of sample receptacles include sample wells, tubes, capillaries, vials and any other vessel, groove or indentation capable of holding a sample. A sample receptacle can be contained on a multi-sample platform, such as a microplate, slide, microfluidics device, and the like.

A support can be composed of a natural or synthetic material, an organic or inorganic material. The composition of the solid support on which the binding agents are attached generally depend on the method of attachment (e.g., covalent attachment). Suitable solid supports include, but are not limited to, plastics, resins, polysaccharides, silica or silica-based materials, functionalized glass, modified silicon, carbon, metals, inorganic glasses, membranes, nylon, natural fibers such as silk, wool and cotton, or polymers. The material comprising the solid support can have reactive groups such as carboxy, amino, or hydroxyl groups, which are used for attachment of the polynucleotides. Polymeric solid supports can include, e.g., polystyrene, polyethylene glycol tetraphthalate, polyvinyl acetate, polyvinyl chloride, polyvinyl pyrrolidone, polyacrylonitrile, polymethyl methacrylate, polytetrafluoroethylene, butyl rubber, styrenebutadiene rubber, natural rubber, polyethylene, polypropylene, (poly)tetrafluoroethylene, (poly)vinylidenefluoride, polycarbonate, or polymethylpentene (see, e.g., U.S. Pat. No. 5,427,779, the disclosure of which is hereby incorporated by reference in its entirety).

Each binding agent (of a plurality of binding agents) on an array can be immobilized at predetermined positions such that each binding agent can be identified by its position. Methods for producing arrays for use in the methods, and to be included in the kits, described herein are described in, e.g., U.S. Pat. No. 6,537,749; U.S. Publication No. 20060040377; and PCT Publication No. WO 03/012451, the disclosures of each of which are incorporated herein by reference in their entirety.

The arrays of binding agents can also be conjugated to solid support particles. Many suitable solid support particles are known in the art and illustratively include, e.g., particles, such as Luminex®-type encoded particles, magnetic particles, and glass particles.

Exemplary particles that can be used can have a variety of sizes and physical properties. Particles can be selected to have a variety of properties useful for particular experimental formats. For example, particles can be selected that remain suspended in a solution of desired viscosity or to readily precipitate in a solution of desired viscosity. Particles can be selected for ease of separation from sample constituents, for example, by including purification tags for separation with a suitable tag-binding material, paramagnetic properties for magnetic separation, and the like.

In some embodiments, encoded particles are used. Each particle includes a unique code (such as a bar code, luminescence code, fluorescence code, a nucleic acid code, and the like). Encoding can be used to provide particles for evaluating different biomarker peptides in a single biological sample. The code is embedded (for example, within the interior of the particle) or otherwise attached to the particle in a manner that is stable through hybridization and analysis. The code can be provided by any detectable means, such as by holographic encoding, by a fluorescence property, color, shape, size, weight, light emission, quantum dot emission and the like to identify particle and thus the binding agents immobilized thereto. Encoding can also be the ratio of two or more dyes in one particle that is different than the ratio present in another particle. For example, the particles may be encoded using optical, chemical, physical, or electronic tags. Examples of such coding technologies are optical bar codes fluorescent dyes, or other means. In some embodiments, the particle code is a nucleic acid, e.g., a single stranded nucleic acid.

Different encoded particles can be used to detect or measure multiple biomarker peptides in parallel, so long as the encoding can be used to identify the biomarker peptide on a particular particle, and hence determine the presence or amount of the biomarker peptide in a biological sample being evaluated. A biological sample can be contacted with a plurality of such encoded particles. When the particles are evaluated, e.g., using a fluorescent scanner, the particle code is read as is the fluorescence associated with the particle from any probe used to evaluate the biomarker peptide associated with the particles.

One exemplary platform utilizes mixtures of fluorescent dyes impregnated into polymer particles as the means to identify each member of a particle set to which a specific biomarker peptide has been immobilized. Another exemplary platform uses holographic barcodes to identify cylindrical glass particles. For example, Chandler et al. (U.S. Pat. No. 5,981,180) describes a particle-based system in which different particle types are encoded by mixtures of various proportions of two or more fluorescent dyes impregnated into polymer particles. Soini (U.S. Pat. No. 5,028,545) describes a particle-based multiplexed assay system that employs time-resolved fluorescence for particle identification. Fulwyler (U.S. Pat. No. 4,499,052) describes an exemplary method for using particle distinguished by color and/or size. U.S. Publication Nos. 2004-0179267, 2004-0132205, 2004-0130786, 2004-0130761, 2004-0126875, 2004-0125424, and 2004-0075907 describe exemplary particles encoded by holographic barcodes.

U.S. Pat. No. 6,916,661 describes polymeric microparticles that are associated with nanoparticles that have dyes that provide a code for the particles. The polymeric microparticles can have a diameter of less than one millimeter, e.g., a size ranging from about 0.1 to about 1,000 micrometers in diameter, e.g., 3-25 μm or about 6-12 μm. The nanoparticles can have, e.g., a diameter from about 1 nanometer (nm) to about 100,000 nm in diameter, e.g., about 10-1,000 nm or 200-500 nm.

In some embodiments, the diameter (or longest straight dimension) of the particle can be between about 1 nm to about 1000 nm or larger. For example, a particle can be at least about 1 nm to about 1000 nm (e.g., at least about two, three, four, five, six, seven, eight, nine, 10, 15, 20, 25, 30, 35, 40, 45, 50, 75, 100, 150, 200, 250, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 nm). In some embodiments, a particle can be not more than 1000 nm (e.g., not more than 975, 950, 925, 900, 875, 850, 825, 800, 775, 750, 725, 700, 675, 650, 625, 600, 575, 550, 525, 500, 475, 450, 425, 400, 375, 350, 325, 300, 275, 250, 225, 200, 175, 150, 125, 100, 75, 50, 45, 40, 35, 30, 25, 20, 15, 10, or five nm) in diameter (or at its longest straight dimension).

A binding agent can be associated with a solid support in a number of ways. For example, the binding agent can be covalently or non-covalently bound to a solid support.

A variety of chemical reactions useful for covalently attaching a substrate to a support are well known to those skilled in the art (see, for example, Hartmann et al. (2002) J. Mater. Res. 17(2):473-478). Illustrative examples of functional groups useful for covalent attachment of substrates to a support include alkyl, Si—OH, carboxy, carbonyl, hydroxyl, amide, amine, amino, ether, ester, epoxides, cyanate, isocyanate, thiocyanate, sulfhydryl, disulfide, oxide, diazo, iodine, sulfonic or similar groups having chemical or potential chemical reactivity. Illustrative examples of binding partners useful for non-covalent attachment of substrates to a support include antibodies, antibody-like materials, and agents, e.g., that are capable of binding to antibodies such as, but not limited to, staphylococcal protein A or protein G.

In some embodiments, the surface of the solid support can be modified to facilitate the stable attachment of linkers or binding agents. Generally a skilled artisan can use routine methods to modify a solid support in accordance with the desired application. The following are non-limiting examples of solid support modifications.

The surface of the solid support can, e.g., have a coating that facilitates the attachment to the binding agent. In general, the coating will be one that is complementary to a linker moiety on the binding agent. For example, the coating on the solid support can be biotin and the binding agent can be bound to streptavidin.

The surface of a solid support can be amidated, e.g., by silylating the surface, e.g., with trialkoxyaminosilane. Silane-treated supports can also be derivatized with homobifunctional and heterobifunctional linkers. The support can be derivatized, e.g., so it has a hydroxy, an amino (e.g., alkylamine), carboxyl group, N-hydroxy-succinimidyl ester, photoactivatable group, sulfhydryl, ketone, or other functional group available for reaction. The supports can be derivatized with a mask in order to only derivatize limited areas (e.g., certain wells of a multiwell assay plate) or a chemical etch or UV light can be used to remove derivatization from selected regions.

The functional groups, instead of being coated on the surface, can be incorporated into the solid support either during or after the preparation of the solid support. The functional groups are usually chosen to dissolve in one or more components of the solid support but may be covalently attached to the solid support.

Kits

One or more of the arrays described herein can be included in kits (e.g., for detecting a biomarker) along with, optionally, a reagent for detectably labeling a biomarker peptide and/or a detectably labeled biomarker peptide (e.g., as a control). A reagent for detectably labeling a biomarker peptide can be, e.g., a detectable label (see above) or a cross-linker to attach a detectable label to a biomarker peptide. The kit can also include instructions for detectably labeling a biomarker peptide. These methods are known in the art and are described above.

Also featured are kits for detecting a biomarker, which include: one or more biomarker peptides selected from any of the peptides, e.g., a biomarker peptide depicted in Tables 6, 8, 9, and SEQ ID NO:1, wherein the one or more biomarker peptides comprise at least one heavy atom isotope; and optionally instructions for how to detect the one or more biomarker peptides using mass spectrometry. The kits can also contain one or more reagents (e.g., solubilization buffers, detergents, or buffers) for isolating a peptide from a biological sample. The kits can also contain a CA125 polypeptide, e.g., a CA125 polypeptide comprising at least one heavy isotope atom. The kit can also include a Matrix-Assisted Laser Desorption Ionization (MALDI) target plate.

The disclosure also provides a kit for detecting a biomarker, wherein the kit contains at least one antibody that binds to a biomarker peptide, e.g., a biomarker peptide depicted in any of Tables 6, 8, 9, and SEQ ID NO:1 and/or P21-activated kinase 7, Brain specific angiogenesis inhibitor 3 (BAI3), a glypican, Granzyme H, CREB-binding protein, NOTCH, hHeadcase, a component of the 26S proteosome, SET binding protein (SEB), and a fragment of any of the foregoing; and, optionally, instructions for how to detect a biomarker peptide using the antibody.

Any of the kits described herein can also include, e.g., buffers, blocking agents, mass spectrometry matrix materials, antibody capture agents, positive control samples, negative control samples, software and information such as protocols, guidance and reference data.

Applications

The Biomarkers, Arrays, Compositions, and Kits described herein can be used in a wide variety of applications (e.g., diagnostic and medical applications). Exemplary applications include, but are in no way limited to, the following.

Methods for Detecting Ovarian Cancer

Methods for detecting an ovarian cancer in a subject (e.g., a mammal such as a human) can include the step of detecting one or both of the presence and amount (or measuring the amount) of one or more biomarkers in a biological sample from a subject. In some embodiments, at least one of the biomarkers is a peptide selected from any of the peptides depicted in Tables 6, 8, 9, and SEQ ID NO:1, and the presence or amount of the biomarker peptide in the biological sample is an indication that the subject has an ovarian cancer.

In some embodiments, the presence of a biomarker peptide in the biological sample is an indication that the subject has an ovarian cancer. In some embodiments, the absence of a biomarker peptide in the biological sample is an indication that the subject has an ovarian cancer.

In some embodiments, an amount of the biomarker peptide in the biological sample that is similar to an ovarian cancer-positive reference amount of the biomarker peptide can indicate that the subject has an ovarian cancer.

In some embodiments, a difference in the amount of the biomarker peptide in the biological sample as compared to a non-ovarian cancer reference amount of the biomarker peptide indicates that the subject has an ovarian cancer. An increase (e.g., a one-fold, a two-fold, a three-fold, a four-fold, a five-fold, a six-fold, a seven-fold, an eight-fold, a nine-fold, or a ten-fold or more increase) in the amount of a biomarker peptide in the biological sample as compared to the non-ovarian cancer reference amount of the biomarker peptide can be an indication that the subject has an ovarian cancer. Alternatively, a decrease (e.g., a one-fold, a two-fold, a three-fold, a four-fold, a five-fold, a six-fold, a seven-fold, an eight-fold, a nine-fold, or a ten-fold or more decrease) in the amount of a biomarker peptide in the biological sample as compared to the non-ovarian cancer reference amount of the biomarker peptide indicates that the subject has an ovarian cancer.

A reference amount (e.g., a non-ovarian cancer reference amount or an ovarian cancer positive reference amount) can be determined using any of a variety of well known methods, provided that the resulting reference amount accurately provides an amount of a biomarker peptide (e.g., any of the biomarker peptides described herein) that exists in a first group of individuals having a different probability of ovarian cancer than that of a second group of individuals having an amount of the biomarker peptide below (or in some cases, above) the reference level. For example, biological samples from a group of individuals known to have ovarian cancer can contain, on average, an amount X of a biomarker peptide, whereas biological samples from a group of individuals known to be cancer-free can contain an amount of the biomarker peptide that is on average two-fold lower than X. Thus, in this instance, an ovarian cancer-positive reference amount of the biomarker peptide can be X and a non-ovarian cancer reference amount of the biomarker peptide is an amount that is two-fold lower than X.

A reference amount can be determined by comparison of biomarker peptide amount in populations of non-cancer patients and those having ovarian cancer. This can be accomplished, for example, by histogram analysis, in which an entire cohort of patients are graphically presented, wherein a first axis represents the amount of biomarker peptide and a second axis represents the number of individuals in the cohort whose sample contain the biomarker peptide at a given amount. Two or more separate groups of individuals can be determined by identification of subsets populations of the cohort which have the same or similar amounts of biomarker peptide. Determination of the reference amount can then be made based on an amount which best distinguishes these separate groups. The reference amount can be a single number, equally applicable to every individual, or the reference amount can vary, according to specific subpopulations of individuals.

In some embodiments, the non-ovarian cancer reference amount of the biomarker peptide can be the amount of the biomarker peptide in a biological sample from a subject that does (or the average amount in biological samples from a cohort of subjects that do) not have an ovarian cancer. In some embodiments, the non-ovarian cancer reference amount of the biomarker peptide can be the amount of the biomarker peptide in a biological sample comprising a non-ovarian cancer reference amount of CA125.

It will be recognized that a level of biomarker peptide that is less than one-fold different than a non-cancer reference can have statistical significance as well, and thus can be used in a method described herein. The statistically relevant difference between ovarian cancer and non-cancer reference levels of biomarker peptide can be determined empirically for various test conditions, such as for particular peptide isolation method, peptide detection method, cohort or population of individuals, selected statistical algorithm, type of ovarian cancer, stage of ovarian cancer, and biopsy method. The particular reference levels of a peptide biomarker such can be determined for ovarian cancers in general, as well as for particular types of ovarian cancer.

The one or more biomarkers detected in the methods can comprise at least four of the biomarker peptides. The at least four biomarker peptides can be selected from (or can be) the group consisting of SEQ ID NOS: 8 and 15.

The one or more biomarkers can comprise at least five of the biomarker peptides. For example, the at least five biomarker peptides can be selected from (or can be) the group consisting of SEQ ID NOS: 2, 3, 4, 5, and 6.

The one or more biomarkers can comprise at least seven of the biomarker peptides and the seven biomarker peptides can be selected from (or can be) the group consisting of SEQ ID NOS: 8, 15, 2, 3, 4, 5, and 6.

The one or more biomarkers can comprise at least nine of the biomarker peptides. For example, the at least nine biomarker peptides can be selected from (or can be) the group consisting of SEQ ID NOS: 9, 8, 12, 10, 11, 15, 22, 13, and 20.

As detailed in the accompanying examples, the presence or amount of individual biomarker peptides, or groups of biomarker peptides, in a biological sample from a subject can be used in the detection of an ovarian cancer in a subject. For example, where the detected biomarkers comprise SEQ ID NOS: 8 and 15, one or both of a decrease in the amount of SEQ ID NO: 8 and an increase in the amount of SEQ ID NOS: 15, in the biological sample as compared to a non-ovarian cancer reference amount of the biomarkers can be an indication that the subject has an ovarian cancer. In another example, where the detected biomarkers comprise SEQ ID NOS: 2, 3, 4, 5, and 6, one or both of a decrease in the amount of SEQ ID NO: 2 and 4 and an increase in the amount of SEQ ID NOS: 3, 5, and 6, in the biological sample as compared to a non-ovarian cancer reference amount of the biomarkers can be an indication that the subject has an ovarian cancer.

In yet another example, wherein the detected biomarkers comprise SEQ ID NOS: 8, 15, 2, 3, 4, 5, and 6, one or both of a decrease in the amount of SEQ ID NOS: 8, 2, and 4, and an increase in the amount of SEQ ID NOS: 15, 3, 5, and 6, in the biological sample as compared to a non-ovarian cancer reference amount of the biomarkers can indicate that the subject has an ovarian cancer. Where the detected biomarkers comprise SEQ ID NOS: 9, 8, 12, 10, 11, 15, 22, 13, and 20, one or both of a decrease in the amount of SEQ ID NOS: 9, 8, 12, and 10, and an increase in the amount of SEQ ID NOS: 15, 22, and 20, in the biological sample as compared to a non-ovarian cancer reference amount of the biomarkers can be an indication that the subject has an ovarian cancer.

In some embodiments, an increased amount of SEQ ID NO: 11 or SEQ ID NO: 13 in a biological sample from a subject as compared to a non-ovarian cancer reference amount can indicate that a subject has an ovarian cancer. In some embodiments, a decreased amount of SEQ ID NO: 11 or SEQ ID NO: 13 in a biological sample from a subject as compared to a non-ovarian cancer reference amount can indicate that a subject has an ovarian cancer (e.g., a Stage I ovarian cancer).

As described above, an ovarian cancer in a subject can be detected by detecting the presence or amount of at least one of the biomarkers selected from the group consisting of P21-activated kinase 7, Granzyme H, CREB-binding protein, NOTCH, hHeadcase, SET binding protein (SEB), and a fragment of any of the foregoing. That is, the presence or amount of at least one of these biomarker peptides in a biological sample from a subject can indicate that the subject has an ovarian cancer. The presence or amount of any of P21-activated kinase 7, Brain specific angiogenesis inhibitor 3 (BAI3), a glypican, Granzyme H, CREB-binding protein, NOTCH, hHeadcase, a component of the 26S proteosome, SET binding protein (SEB), and a fragment of any of the foregoing, can be detected in a variety of ways known in the art (see Sambrook et al. (supra). For example, the presence or amount of mRNA encoding the biomarker in a biological sample can be detected using, e.g., reverse transcriptase-polymerase chain reaction or northern blot analysis. Biomarker protein can be detected using, e.g., mass spectrometry, western/dot blotting or other immunoassays, or protein chips (see above).

The methods described herein can be useful for detecting various forms and stages of ovarian cancer. Examples of types of ovarian cancers include serous cystomas, such as serous cystadenomas and serous cystadenocarcinomas; mucinous cystomas, such as mucinous benign cystadenomas, mucinous cystadenomas and mucinous cystadenocarcinomas; endometrioid tumors (similar to adenocarcinomas in the endometrium), such as endometrioid benign cysts and endometrioid adenocarcinomas; clear cell (mesonephroid) tumors such as clear cell cystadenocarcinomas; and unclassified tumors that are not characterized as any group listed above. For example, in some embodiments of the methods, one or both of the presence and amount of the biomarker peptide in the biological sample from a subject can indicate that the subject has an ovarian cancer of a type selected from the group consisting of a serous cystoma, a mucinous cystoma, an endometroid tumor, and a clear cell tumor.

For determining a reference level of a biomarker in particular types of ovarian cancer, ovarian cancer samples from individuals are typically classified by histological features and/or biochemical markers, and bodily fluid or tissue samples from the individuals are assessed for levels of the particular biomarker in comparison to non-cancer controls.

The methods described herein can be used to differentiate between stages of ovarian cancer because different levels of biomarker peptides are present in and released from tumors at different stages. Staging of ovarian cancer is well known to the skilled clinician. As an example of ovarian cancer staging, the Federation Internationale de Gynecologie et d'Obstetrique (FIGO) and the American Joint Committee on Cancer (AJCC) have designated the following staging. Stage I refers to cancer that is limited to the ovaries. Stage IA refers to tumors limited to 1 ovary, with capsule intact, no tumor on ovarian surface, with no malignant cells in ascites or peritoneal washings. Stage IB refers to tumors limited to both ovaries, with capsules intact, no tumor on ovarian surface and no malignant cells in ascites or peritoneal washings. Stage IC refers to tumors limited to 1 or both ovaries with any of the following: capsule ruptured, tumor on ovarian surface, malignant cells in ascites or peritoneal washings. Stage II ovarian cancer refers to tumors involving 1 or both ovaries with pelvic extension and/or implants. Stage IIA refers to extension and/or implants on the uterus and/or fallopian tubes and no malignant cells in ascites or peritoneal washings. Stage IIB refers to extension to and/or implants on other pelvic tissues and no malignant cells in ascites or peritoneal washings. Stage IIC refers to pelvic extension and/or implants (stage IIA or stage IIB) with malignant cells in ascites or peritoneal washings. Stage III ovarian cancer refers to tumors involving 1 or both ovaries with microscopically confirmed peritoneal implants outside the pelvis, wherein the tumor is limited to the true pelvis but with histologically verified malignant extension to small bowel or omentum. Stage IIIA refers to microscopic peritoneal metastasis beyond pelvis (no macroscopic tumor). Stage IIIB refers to macroscopic peritoneal metastasis beyond pelvis $\leq 2$ cm in greatest dimension. Stage IIIC refers to peritoneal metastasis beyond pelvis >2 cm in greatest dimension and/or regional lymph node metastasis. Stage IV ovarian cancer refers to tumors involving 1 or both ovaries with distant metastasis, and parenchymal liver metastasis equals stage IV. For example, one or both of the presence and amount of the biomarker peptide in a biological sample from a subject can indicate that the subject has an ovarian cancer at a stage selected from the group consisting of Stage I, Stage IA, Stage IB, Stage IC, Stage II, Stage IIA, Stage IIB, Stage IIC, Stage III, Stage IIIA, Stage IIIB, Stage IIIC, and Stage IV.

For determining a reference level of a biomarker in particular stages of ovarian cancer, ovarian cancer samples from individuals are typically classified by histological features and/or biochemical markers, and bodily fluid or tissue samples from the individuals are assessed for levels of the particular biomarker in comparison to non-cancer controls.

In some embodiments, the methods can also include the step of detecting one or both of the presence and amount of CA125 in the biological sample from the subject.

The presence or amount of a biomarker peptide present in a sample can be determined by any analytical method capable of distinguishing peptide amounts. The example provided herein describes methods for distinguishing peptide amounts using MALDI-OTOF mass spectrometry. A variety of configurations of mass spectrometers can be used in a method for distinguishing peptide amounts. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al. Anal. Chem. 70:647R-716R (1998); Kinter and Sherman, New York (2000)).

Various well-known assays can be used for detecting a peptide within a sample. Such assays can be designed, if appropriate for a particular biomarker, to allow detecting of a particular peptide within a sample that contains other peptides from a common parent protein, and/or the parent protein. Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

For example, a lysate can be prepared from a biological sample, or the biological sample itself, can be contacted with Laemmli buffer and subjected to sodium-dodecyl sulfate polyacrylamide gel electrophoresis (SDS-PAGE). SDS-PAGE-resolved proteins, separated by size, can then be transferred to a filter membrane (e.g., nitrocellulose) and subjected to immunoblotting techniques using a detectably-labeled antibody specific to the protein of interest. The presence or amount of bound detectably-labeled antibody indicates the presence or amount of biomarker peptide in the biological sample.

In another example, an immunoassay can be used for detecting and/or measuring the a biomarker peptide. As above, for the purposes of detection, an immunoassay can be performed with an antibody that bears a detection moiety (e.g., a fluorescent agent or enzyme). Biomarker peptides from a biological sample can be conjugated directly to a solid support (e.g., a multi-well assay plate, nitrocellulose, agarose, sepharose, encoded particles, or magnetic beads) or they can be conjugated to a first member of a specific binding pair (e.g., biotin or streptavidin) that attaches to a solid support upon binding to a second member of the specific binding pair (e.g., streptavidin or biotin) bound to the support. Such attachment to a solid support allows the proteins to be purified away from other interfering or irrelevant components of the biological sample prior to contact with the detection antibody and also allows for subsequent washing of unbound antibody. Here as above, the presence or amount of bound detectably-labeled antibody indicates the presence or amount of protein in the biological sample.

Methods for generating antibodies or antibody fragments specific for a biomarker peptide can are described in detail below. The antibody can be a monoclonal antibody or a preparation of polyclonal antibodies.

Methods of detecting and/or for quantifying a detectable label depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for rapid preparation, processing, and analysis of multiple reactions. This can be, for example, in multi-well assay plates (e.g., 96 wells or 386 wells) or using the arrays described herein. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Biological Samples and Sample Collection

In some embodiments, any of the methods described herein can also include the step of providing a biological sample from a subject and/or obtaining a biological sample from a subject. Suitable biological samples for the methods described herein include any biological fluid, cell, tissue, or fraction thereof, which includes analyte biomarkers of interest such as any of the biomarkers described herein (e.g., any of the peptides depicted in Tables 6, 8, 9, and SEQ ID NO:1). A biological sample can be, for example, a specimen obtained from a subject (e.g., a mammal such as a human) or can be derived from such a subject. For example, a sample can be a tissue section obtained by biopsy, or cells that are placed in or adapted to tissue culture. A biological sample can also be a biological fluid such as urine, blood, plasma, serum, saliva, semen, sputum, cerebral spinal fluid, tears, or mucus, or such a sample absorbed onto a paper or polymer substrate. A biological sample can be further fractionated, if desired, to a fraction containing particular cell types. For example, a blood sample can be fractionated into serum or into fractions containing particular types of blood cells such as red blood cells or white blood cells (leukocytes). If desired, a sample can be a combination of samples from a subject such as a combination of a tissue and fluid sample. The Example below describes ovarian cancer biomarkers identified in serum.

The biological samples can be obtained from a subject, e.g., a subject having, suspected of having, or at risk of developing, a cancer (e.g., an ovarian cancer). Any suitable methods for obtaining the biological samples can be employed, although exemplary methods include, e.g., phlebotomy, swab (e.g., buccal swab), or fine needle aspirate biopsy procedure. Non-limiting examples of tissues susceptible to fine needle aspiration include lymph node, lung, thyroid, breast, and liver. Samples can also be collected, e.g., by microdissection (e.g., laser capture microdissection (LCM) or laser microdissection (LMD)), bladder wash, smear (PAP smear), or ductal lavage.

Methods for obtaining and/or storing samples that preserve the activity or integrity of molecules (e.g., nucleic acids or proteins) in the sample are well known to those skilled in the art. For example, a biological sample can be further contacted with one or more additional agents such as appropriate buffers and/or inhibitors, including nuclease, protease and phosphatase inhibitors, which preserve or minimize changes in the molecules (e.g., nucleic acids or proteins) in the sample. Such inhibitors include, for example, chelators such as ethylenediamine tetraacetic acid (EDTA), ethylene glycol bis(P-aminoethyl ether) N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for isolating molecules are well known to those skilled in the art and can be varied depending, for example, on the type of molecule in the sample to be characterized (see, for example, Ausubel et al. Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999)). A sample also can be processed to eliminate or minimize the presence of interfering substances. For example, a biological sample can be fractionated or purified to remove one or more materials that are not of interest. Methods of fractionating or purifying a biological sample include, but are not limited to, chromatographic methods such as liquid chromatography, ion-exchange chromatography, size-exclusion chromatography, or affinity chromatography.

For use in the methods described herein, a sample can be in a variety of physical states. For example, a sample can be a liquid or solid, can be dissolved or suspended in a liquid, can be in an emulsion or gel, and can be absorbed onto a material.

Exemplary biological samples, methods for obtaining the samples, and their use and analysis are detailed in the accompanying Example.

Biomarker Profiles and Methods for Selecting and Administering a Therapy

The methods and materials described herein can be used to, e.g., (a) diagnose a cancer (e.g., an ovarian cancer) in a subject (see above) and/or (b) generate a biomarker profile for a subject. The profile can include information that indicates whether one or more of the biomarker peptides, such as one or more of any of the peptides depicted in Tables 6, 8, 9, and SEQ ID NO:1, are present (e.g., yes or no) in a biological sample from a subject and/or information that indicates the amount of one or more biomarker peptides (e.g., one or more of any of the peptides depicted in Tables 6, 8, 9, and SEQ ID NO:1) in a biological sample from the subject. The profile can also one or more non-ovarian cancer reference amounts of the biomarkers and/or one or more ovarian cancer-positive reference amounts of the biomarkers. A biomarker profile can include information regarding the presence or amount of one or more biomarkers other than any of the peptides depicted in Tables 6, 8, 9, and SEQ ID NO:1, in a biological sample. For example, the biomarker profile can include the amount of CA125, if present, in the biological sample.

The biomarker profiles described herein can contain information on the presence or amount of at least two or more (e.g., at least three or more, at least four or more, at least five or more, at least six or more, at least seven or more, at least eight or more, at least nine or more, at least 10 or more, at least 11 or more, at least 12 or more, at least 13 or more, at least 14 or more, at least 15 or more, at least 16 or more, at least 17 or more, at least 18 or more, at least 19 or more, at least 20 or more, at least 25 or more, 30 or more, or at least 35 or more) of any of the peptides depicted in Tables 6, 8, 9, and SEQ ID NO:1.

Grouping of multiple biomarker peptides (e.g., 2, 3, 4, 5, 6, 7, 8, or more biomarker peptides depicted in Tables 6, 8, 9, and SEQ ID NO:1) into sets or marker models can improve the sensitivity for or specificity in detecting an ovarian cancer. For example, the accompanying Example describes the grouping of the biomarker peptides depicted in Tables 6, 8, 9, and SEQ ID NO:1 into groups of four, five, seven, and nine. In this instance, a grouping of four biomarker peptides, e.g., delivered an equivalent 93% sensitivity and enhanced (97%) specificity of detection.

The resultant information (the biomarker profile of a subject) can be used for determining whether a subject has, or is likely to have, an ovarian cancer (as described above) and/or whether the subject should undergo additional diagnostic tests to confirm the presence, the stage, or the type of ovarian cancer. For example, the biomarker profile can be used to determine if a subject should undergo one or more additional diagnostic tests to detect an ovarian cancer if the amount of one or more biomarker peptides in a biological sample obtained from the subject is similar to the ovarian cancer-positive reference amount of the biomarker peptide. In another example, the biomarker profile can be used to determine if a subject should undergo one or more additional diagnostic tests to detect an ovarian cancer if the amount of the biomarker peptide is different than the non-ovarian cancer reference amount of the biomarker peptide. An example of additional diagnostic tests to determine the presence, stage, or type of ovarian cancer in a subject include, but are not limited to, a biopsy, imaging studies (e.g., ultrasound, computed tomography (CAT), or magnetic resonance imaging (MRI)), or a CA125 test.

The biomarker profiles can be used, e.g., in diagnosing an ovarian cancer whether or not physiologic symptoms of the ovarian cancer have become apparent.

After detecting a cancer (e.g., an ovarian cancer) in a subject, e.g., using a method described above, a medical practitioner (e.g., a doctor) can select an appropriate therapeutic modality for the subject (e.g., a therapy comprising one or more anti-cancer agents). For example, a medical practitioner can select (or prescribe) for a subject a therapy comprising an anti-cancer agent if the amount of a biomarker peptide in a biological sample from the subject is similar to the ovarian cancer-positive reference amount of the biomarker peptide. In another example, a medical practitioner can select (or prescribe) for a subject a therapy comprising an anti-cancer agent if the amount of the biomarker peptide in a biological sample from the subject is different than the non-ovarian cancer reference amount of the biomarker peptide Selecting a therapy for a subject can be, e.g.: (i) writing a prescription for a medicament; (ii) giving (but not necessarily administering) a medicament to a subject (e.g., handing a sample of a prescription medication to a patient while the patient is at the physician's office); (iii) communication (verbal, written (other than a prescription), or electronic (email, an electronic post to a secure site)) to the patient of the suggested or recommended therapeutic modality (e.g., a therapy comprising one or more anti-cancer agents); or (iv) identifying a suitable therapeutic modality for a subject and disseminating the information to other medical personnel, e.g., by way of patient record. The latter (iv) can be useful in a case where, e.g., more than one therapy or therapeutic agent are to be administered to a patient by different medical practitioners.

It is understood that the biomarker profile can be in electronic form (e.g., an electronic patient record stored on a computer or other electronic (computer-readable) media such as a DVD, CD, or floppy disk) or other tangible form such as a written or printed form. The biomarker profile can include information for several (e.g., two, three, four, five, 10, 20, 30, 50, or 100 or more) subjects (e.g., human patients). Such multi-subject biomarker profiles can be used, e.g., in analyses (e.g., statistical analyses) of particular characteristics of subject cohorts.

After detecting an ovarian cancer in a subject (using any of the methods above); studying a biomarker profile for a subject; and/or selecting a therapy for the subject, a medical practitioner (e.g., a doctor) can administer the appropriate therapeutic modality to the subject (e.g., a therapy comprising an anti-cancer agent). Methods for administering a therapy comprising an anti-cancer agent are known in the art and described in, e.g., U.S. Pat. Nos. 6,566,393; 7,176,236; 5,6748,72; and 6,653,341, the disclosures of each of which are incorporated herein by reference in their entirety. Suitable therapies include, e.g., surgery, chemotherapy, and/or radiotherapy. Examples of chemotherapeutic agents include, e.g., carboplatin, cisplatin, topotecan, gemcitabine, etoposide (VP-16 or VePesid®), melphalan (Alkeran®), and hexamethylamine (Hexylen®, altretamine).

In addition, a medical practitioner can also select, prescribe and/or administer one or more medicaments to treat side-effects of an anti-cancer agent such as anemia, gastrointestinal symptoms (e.g., nausea, vomiting, diarrhea), leukopenia (decreased number of white blood cells, which may cause infection), temporary hair loss, or thrombocytopenia (decreased number of platelets, which may cause bleeding). For example, a doctor can prescribe or administer to a subject a chemotherapeutic agent such as etoposide along with an anti-anemia medicament such as epoetin alpha (e.g., Procrit®, Epogen®).

Methods for Generating an Antibody

Methods of producing an antibody specific for a biomarker peptide (e.g., a biomarker peptide depicted in any of Tables 6, 8, 9, and SEQ ID NO:1) are known in the art and detailed below. For example, methods for generating antibodies or antibody fragments specific for a polypeptide described herein can be generated by immunization, e.g., using an animal, or by in vitro methods such as phage display. All or part of a polypeptide described herein can be used to generate an antibody or antibody fragment.

A biomarker peptide can be used to prepare antibodies by immunizing a suitable subject, (e.g., rabbit, goat, mouse, or other mammal such as a human) with the peptide. An appropriate immunogenic preparation can contain, for example, any of the biomarker peptides described herein. The preparation can further include an adjuvant, such as Freund's complete or incomplete adjuvant, alum, RIBI, or similar immunostimulatory agent. Adjuvants also include, e.g., cholera toxin (CT), E. coli heat labile toxin (LT), mutant CT (MCT) (Yamamoto et al. (1997) J. Exp. Med. 185:1203-1210) and mutant E. coli heat labile toxin (MLT) (Di Tommaso et al. (1996) Infect. Immunity 64:974-979). MCT and MLT contain point mutations that substantially diminish toxicity without substantially compromising adjuvant activity relative to that of the parent molecules. Immunization of a suitable subject with an immunogenic peptide preparation (e.g., any of the reagents described herein) induces a polyclonal anti-peptide antibody response.

The term antibody as used herein refers to immunoglobulin molecules and immunologically active portions of immunoglobulin molecules (i.e., molecules that contain an antigen binding site that specifically bind to the peptide (e.g., a biomarker peptide described herein). An antibody that specifically binds to a peptide described herein is an antibody that binds the peptide, but does not substantially bind other molecules in a sample. Examples of immunologically active portions of immunoglobulin molecules include F(ab) and F(ab')$_2$ fragments.

The anti-polypeptide antibody can be a monoclonal antibody or a preparation of polyclonal antibodies. The term monoclonal antibody, as used herein, refers to a population of antibody molecules that contain only one species of an antigen binding site capable of immunoreacting with the polypeptide. A monoclonal antibody composition thus typically displays a single binding affinity for a particular polypeptide with which it immunoreacts.

Polyclonal anti-peptide antibodies can be prepared as described above by immunizing a suitable subject with, e.g., a biomarker peptide immunogen. The anti-peptide antibody titer in the immunized subject can be monitored over time by standard techniques, such as with an enzyme linked immunosorbent assay (ELISA) using immobilized peptide. If desired, the antibody molecules directed against the peptide can be isolated from the mammal (e.g., from the blood) and further purified by techniques such as protein A chromatography to obtain the IgG fraction. At an appropriate time after immunization, e.g., when the anti-peptide antibody titers are highest, antibody-producing cells can be obtained from the subject and used to prepare monoclonal antibodies by standard techniques, such as the hybridoma technique originally described by Kohler and Milstein (1975) Nature 256:495-497, the human B cell hybridoma technique (Kozbor et al. (1983) Immunol. Today 4:72), or the EBV-hybridoma technique (Cole et al. (1985), Monoclonal Antibodies and Cancer Therapy, Alan R. Liss, Inc., pp. 77-96). Any of the many well known protocols used for fusing lymphocytes and immortalized cell lines can be applied for the purpose of generating an anti-peptide monoclonal antibody (see, e.g., Current Protocols in Immunology, supra; Galfre et al. (1977) Nature 266: 55052; R. H. Kenneth, in Monoclonal Antibodies: A New Dimension In Biological Analyses, Plenum Publishing Corp., New York, N.Y. (1980); and Lerner (1981) Yale J. Biol. Med., 54:387-402, the disclosures of each of which are incorporated by reference in their entirety).

As an alternative to preparing monoclonal antibody-secreting hybridomas, a monoclonal anti-peptide antibody can be identified and isolated by screening a recombinant combinatorial immunoglobulin library (e.g., an antibody phage display library) with a peptide described herein to isolate immunoglobulin library members that bind the peptide.

An anti-peptide antibody (e.g., a monoclonal antibody) can be used to isolate the peptide by techniques such as affinity chromatography or immunoprecipitation. Moreover, an anti-peptide antibody can be used to detect the peptide in diagnostic assays described herein. An antibody can optionally be coupled to a detectable label such as any of those described herein or a first or second member of a binding pair (e.g., streptavidin/biotin or avidin/biotin), the second member of which can be conjugated to a detectable label.

Non-human antibodies to a target biomarker peptide (e.g., a biomarker peptide depicted in any of Tables 6, 8, 9, and SEQ ID NO:1) can also be produced in non-human host (e.g., a rodent) and then humanized, e.g., as described in U.S. Pat. No. 6,602,503, EP 239 400, U.S. Pat. No. 5,693,761, and U.S. Pat. No. 6,407,213, the disclosures of each of which are incorporated by reference in their entirety.

EP 239 400 (Winter et al.) describes altering antibodies by substitution (within a given variable region) of their CDRs for one species with those from another. CDR-substituted antibodies can be less likely to elicit an immune response in humans compared to true chimeric antibodies because the CDR-substituted antibodies contain considerably less non-human components. See Riechmann et al., 1988, Nature 332, 323-327; Verhoeyen et al., 1988, Science 239, 1534-1536, the disclosures of each of which is incorporated by reference in their entirety. Typically, CDRs of a murine antibody are substituted into the corresponding regions in a human antibody by using recombinant nucleic acid technology to produce sequences encoding the desired substituted antibody. Human constant region gene segments of the desired isotype (e.g., gamma I for CH and kappa for CL) can be added and the humanized heavy and light chain genes can be co-expressed in mammalian cells to produce soluble humanized antibody.

WO 90/07861 describes a process that includes choosing human V framework regions by computer analysis for optimal protein sequence homology to the V region framework of the original murine antibody, and modeling the tertiary structure of the murine V region to visualize framework amino acid residues that are likely to interact with the murine CDRs. These murine amino acid residues are then superimposed on the homologous human framework. See also U.S. Pat. Nos. 5,693,762; 5,693,761; 5,585,089; and 5,530,101. Tempest et al., 1991, Biotechnology 9, 266-271 use, as standard, the V region frameworks derived from NEWM and REI heavy and light chains, respectively, for CDR-grafting without radical introduction of mouse residues. An advantage of using the Tempest et al. approach to construct NEWM and REI based humanized antibodies is that the three dimensional structures of NEWM and REI variable regions are known from x-ray crystallography and thus specific interactions between CDRs and V region framework residues can be modeled.

Non-human antibodies can be modified to include substitutions that insert human immunoglobulin sequences, e.g., consensus human amino acid residues at particular positions, e.g., at one or more (e.g., at least five, ten, twelve, or all) of the following positions: (in the framework of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the framework of the variable domain of the heavy chain) 2H, 4H, 24H, 36H, 37H, 39H, 43H, 45H, 49H, 58H, 60H, 67H, 68H, 69H, 70H, 73H, 74H, 75H, 78H, 91H, 92H, 93H, and/or 103H (according to the Kabat numbering). See, e.g., U.S. Pat. No. 6,407,213, the disclosure of which is incorporated herein by reference in its entirety.

Fully human monoclonal antibodies that bind to a target polypeptide can be produced, e.g., using in vitro-primed human splenocytes, as described by Boerner et al., 1991, J. Immunol., 147, 86-95. They may be prepared by repertoire cloning as described by Persson et al., 1991, Proc. Nat. Acad. Sci. USA, 88: 2432-2436 or by Huang and Stollar, 1991, J. Immunol. Methods 141, 227-236; also U.S. Pat. No. 5,798, 230, the disclosures of each of which are incorporated herein by reference in their entirety. Large nonimmunized human phage display libraries may also be used to isolate high affinity antibodies that can be developed as human therapeutics using standard phage technology (see, e.g., Vaughan et al, 1996; Hoogenboom et al. (1998) Immunotechnology 4:1-20; and Hoogenboom et al. (2000) Immunol Today 2:371-8; US 2003-0232333, the disclosures of each of which are incorporated by reference in their entirety).

As used herein, an "immunoglobulin variable domain sequence" refers to an amino acid sequence that can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), e.g., a structure that interacts with a target polypeptide.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2 and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

One or more regions of an antibody can be human, effectively human, or humanized. For example, one or more of the variable regions can be human or effectively human. For example, one or more of the CDRs, e.g., heavy chain (HC) CDR1, HC CDR2, HC CDR3, light chain (LC) CDR1, LC CDR2, and LC CDR3, can be human. Each of the light chain CDRs can be human. HC CDR3 can be human. One or more of the framework regions (FR) can be human, e.g., FR1, FR2, FR3, and FR4 of the HC or LC. In some embodiments, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human, effectively human, or humanized. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human, effectively human, or humanized. For example, FR1, FR2, and FR3 collectively can be at least 70, 75, 80, 85, 90, 92, 95, 98, or 99% identical to a human sequence encoded by a human germline segment. In some embodiments, to humanize a murine antibody, one or more regions of a mouse Ig loci can be replaced with corresponding human Ig loci (see, e.g., Zou et al. (1996) The FASEB Journal Vol 10, 1227-1232; Popov et al. (1999) J. Exp. Med. 189(10) 1611-1619; and Nicholson et al. (1999) J. Immunol. 6898-6906; the disclosures of each of which are incorporated by reference in their entirety.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. No. 6,407,213 and U.S. Pat. No. 5,693,762, the disclosures of each of which are incorporated herein by reference in their entirety. In some cases, humanized immunoglobulins can include a non-human amino acid at one or more framework amino acid positions.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 kDa or 214 amino acids) are encoded by a variable region gene at the NH2-terminus (about 110 amino acids) and a kappa or lambda constant region gene at the COOH-terminus. Full-length immunoglobulin "heavy chains" (about 50 kDa or 446 amino acids), are similarly encoded by a variable region gene (about 116 amino acids) and one of the other aforementioned constant region genes, e.g., gamma (encoding about 330 amino acids).

The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody include: (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) a Fd fragment consisting of the VH and CH i domains; (iv) a Fv fragment consisting of the VL and VH domains of a single arm of an antibody; (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) Science 242:423-426; and Huston et al. (1988) Proc. Natl. Acad. Sci. USA 85:5879-5883, the disclosures of each of which are incorporated herein by reference in their entirety.

It is understood that an antibody produced by a method described above (e.g., an antibody specific for one or more of the biomarker peptides described herein) can be used to, e.g., detect the presence or amount of a biomarker peptide in a biological sample and thus is useful in the above-described methods.

Articles of Manufacture

The methods and materials described herein can be used to, e.g., diagnose a subject as having an ovarian cancer and to aid a medical practitioner in selecting an appropriate therapy for the subject. To aid in this selection, it may be useful for medicaments used for treating ovarian cancer (such as any of the therapies comprising an anti-cancer agent described herein) to contain information or appropriate labels indicating that the medicaments should be prescribed (and/or administered) to a subject having an amount of one or more of the biomarker peptides indicative of ovarian cancer. Thus, the disclosure also features an article of manufacture comprising: a container; and a composition contained within the container, wherein the composition comprises an active agent for treating an ovarian cancer in a subject and wherein the container has a label indicating that the composition is for use in treating an ovarian cancer in a subject if, e.g., one or both of: (i) a biological sample obtained from the subject contains an amount of a biomarker peptide that is similar to an ovarian cancer-positive reference amount of the biomarker peptide, wherein the biomarker peptide is selected from any of the peptides depicted in Tables 6, 8, 9, and SEQ ID NO:1; and (ii) a biological sample obtained from the subject contains an amount of a biomarker peptide that is different than a non-ovarian cancer reference amount of the biomarker peptide, wherein the biomarker peptide is selected from any of the peptides depicted in Tables 6, 8, 9, and SEQ ID NO:1. The article of manufacture can also contain instructions for administering the active agent to the subject.

The following example is intended to illustrate, not limit, the invention.

Example

This example describes the identification of several peptide biomarkers useful for distinguishing between ovarian cancer patient serum and non-cancer reference serum.

Ovarian cancer serum samples for use in identifying cancer peptide biomarkers were obtained courtesy of G. Whiteley, NCI and D. Fishman, NYU. Serum samples were collected under full patient consent and Institutional Review Board approval. Serum was collected before physical evaluation, diagnosis, and treatment and stored at 80° C. Healthy control individual serum samples were collected from unaffected women (no serial samples). The serum specimens from women with ovarian cancer were procured in a gynecologic oncology clinic from symptomatic women who were later surgically staged and found to have epithelial ovarian carcinoma. Each sample was accompanied by a verified pathology diagnosis. All serum samples were processed from blood drawn under strict NCI/FDA Proteomics Program standard operating guidelines as follows: Specimens were collected in red-top vacutainer tubes and allowed to clot for one hour on ice, 8 followed by centrifugation at 4° C. for 10 minutes at 800 rcf. The serum supernatant was divided in aliquots and stored at –80° C. until needed. The serum samples were assayed for CA125 levels and were classified as "high CA125" if the levels were above 22 ng/ml, and "low CA125" if the levels were below 22 ng/ml. A level of CA125 above 35 ng/ml is considered to be the cutoff indicating likely disease recurrence. Healthy samples had CA125 that were below the levels of detection. The ovarian study set consisted of 560 total samples: 108 Normals and 452 serial samples collected from 44 unique patients. The number of serial samples collected from individual patients varied from 3 to 22 samples per patient.

Cancer and non-cancer reference samples were processed in a random order to account for any systematic errors and variations from experiment to experiment. Both cases and controls were randomly co-mingled during the run cycle such that each plated contained both phenotypes to minimize run bias. The triplicates for each sample, however, were processed at the same time to avoid multiple freeze-thaw cycles of serum. In addition, these triplicates were co-located side-by-side within a row on the MALDI target for convenience. Historical data suggests that there is no apparent advantage of dispersing the replicates within the same MALDI plate. Locations of cancer samples, reference serum, and no-serum control were random on each MALDI plate. Only the peptide standard mix was always spotted in the reserved A1, A2, and A3 positions of the plate.

Serum samples were processed using prototype ProXPRESSION™ biomarker enrichment kits (PerkinElmer, Boston, Mass.). This Cibachron blue (CB) dye affinity chromatography-based technology captures high-abundance carrier proteins in blood (such as albumin) and enriches for the peptide and protein fragments bound to the carrier proteins. ZipPlates and vacuum manifold were purchased from Millipore (Bedford, Mass.). Millipore also provided custom fitting adapters for direct spotting of samples on single use MALDIchip prOTOF Target plates (PerkinElmer). Pre mixed Alpha-Cyano-4-Hydroxycinnamic acid matrix was from PerkinElmer.

Serum samples were processed on 96 well plates using the following procedure: Plates were placed on the vacuum manifold and pre-washed with 180 ul Sample Binding Buffer (SBB) (PerkinElmer, Boston, Mass.). The wash step was repeated 3 times. Low vacuum of less than 25 mm Hg was applied to remove any remaining buffer from the wells. Serum samples were diluted 1:10 in SBB. 100 µl of each diluted serum sample was then applied to each well of the CB plate. The proteins were allowed to bind to the CB medium for 15 min. Low vacuum of less than 25 mm Hg was applied to pass the sample through the CB medium. The wells were then washed 11 times with 180 µl of SBB. A clean collection plate was then placed under the CB Plate and 150 µl of Sample Elution Buffer (SEB) (PerkinElmer, Boston, Mass.) was applied to each well and the biomarkers were eluted with low vacuum of 25 mm Hg.

Eluted biomarkers were concentrated and desalted on ZipPlate™ (Millipore) and applied directly to MALDIchip targets (PerkinElmer) by vacuum elution as follows: A C18 ZipPlate™ was placed on the vacuum manifold. The resin was pre-washed 3 times with 180 µl of 100% acetonitrile, followed by two 180 µl washes with 0.1% trifluoroacetic acid (TFA), which was followed by two 180 µl washes with 100% acetonitrile. Vacuum (375 mm Hg) was applied to clear the wells during the pre-wash steps. The C18 resin was pre-wetted by applying 3 µl of 100% ACN directly to each well of the ZipPlate™. Pipetting was timed to allow approximately 4 minutes for pre-wetting of the C18 matrix before sample application. The entire elution volume from each CB column or CB well was loaded into one well of ZipPlate™ and the sample was bound by applying vacuum at 125 mm of Hg. Vacuum was gradually increased after approximately 5 min to 375 mm of Hg. All samples were allowed to pass completely through the resin before proceeding to the wash steps. The ZipPlate™ was washed 3 times with 300 µl per well of 0.1% TFA. Six additional wash steps were performed using 180 µl of 0.1% TFA per well, per step. The vacuum (375 mm Hg) was applied for up to 10 minutes to remove any remaining liquid.

The peptides were eluted directly by vacuum onto disposable MALDIchip targets by using the following protocol: A pre-washed and dried MALDIchip target was placed beneath the ZipPlate™ (containing the bound biomarkers) in the vacuum manifold (Note: this requires use of a custom PerkinElmer MALDIchip Plate adapter and Millipore ZipPlate™ manifold, available from Millipore (Bedford, Mass.). Vacuum of 50 mm Hg was applied and 3 µl/well of matrix solution was pipetted directly onto each well of the ZipPlate™. After approximately 5 minutes, the vacuum was released and the top cover of the vacuum manifold was removed. The ZipPlate™ was carefully lifted from the MALDIchip target leaving small droplets on the plate, indicating successful sample transfer. Samples were allowed to air dry at room temperature resulting in the formation of matrix crystals.

Mass spectra were acquired on a prOTOF 2000 MALDI O-TOF Mass Spectrometer interfaced with TOFWorks software (PerkinElmer/SCIEX, Concord, ON, Canada). Due to the orthogonal design, a single external mass calibrant was used to achieve better than 5 ppm mass accuracy over an entire sample plate (up to 384 samples). In this study, a two-point external calibration of the prOTOF instrument was performed before acquiring the spectra in a batch mode from 96 samples. MALDI O-TOF MS is capable of collecting data over a wide range of mass values (300 kDa) in a single acquisition. Typical resolution for peptides and proteins up to 10 kDa was greater than 12,000 full width at half maximum (FWHM). For performing ultra High Resolution Tandem Mass Spectrometry, pools of either ovarian cancer samples or healthy samples were dissolved in 50 uL of 5% acetonitrile 0.1% formic acid/water, and transferred to MS plate and lyophilized. Samples in 5% acetonitrile 0.1% formic acid were injected with a Famos Autosampler onto a 75 um×18 cm fused silica capillary column packed with C18 or C8 media, in a 250 uL/min gradient of 5% acetonitrile 0.1% formic acid to 50% acetonitrile 0.1% formic acid over the course of 100 minutes with a total run length of 150 minutes. For the 240 minute runs, 25 cm columns were used to achieve higher chromatographic resolution and loading capacity. The LTQ-FT was run in a top 4 configuration at 200K resolution for a full scan. Ions that were +1 or undefined in charge states were rejected for MS 2 analysis. Dynamic exclusion was set to 1 with a limit of 180 seconds with early expiration set to 6 full scans. Peptide IDs were made using Sequest through the Bioworks Browser 3.2 EF2 Database searches were made using a no-enzyme indexed version of the NCBI RefSeqhuman/reversed Refseqhuman database using differential oxidized methionines at a tolerance of 10 ppm. Peptide score cutoff values were chosen at Xcorr of 1.8 for singly charged ions, 2.0 for doubly charged ions, and 2.5 for triply charged ions, along with deltaCN values of 0.1 or greater, and RSP values of <10 with a peptide P value of 1e-3 or better. The small mass tolerance of the search ensured that only relevant peptides were matched. The cross correlation values chosen for each peptide assured a high confidence match for the different charge states, while the deltaCN cutoff insured the uniqueness of the peptide hit. The p value is a probability score for a random hit peptide. Typically, multiple peptide hits were obtained for any identified protein, for example, over 28 separate hits were obtained for Plasma Kallikrein-sensitive glycoprotein (Table 8). However, there were also a number of proteins that were identified by single peptide hits.

Figure 5:
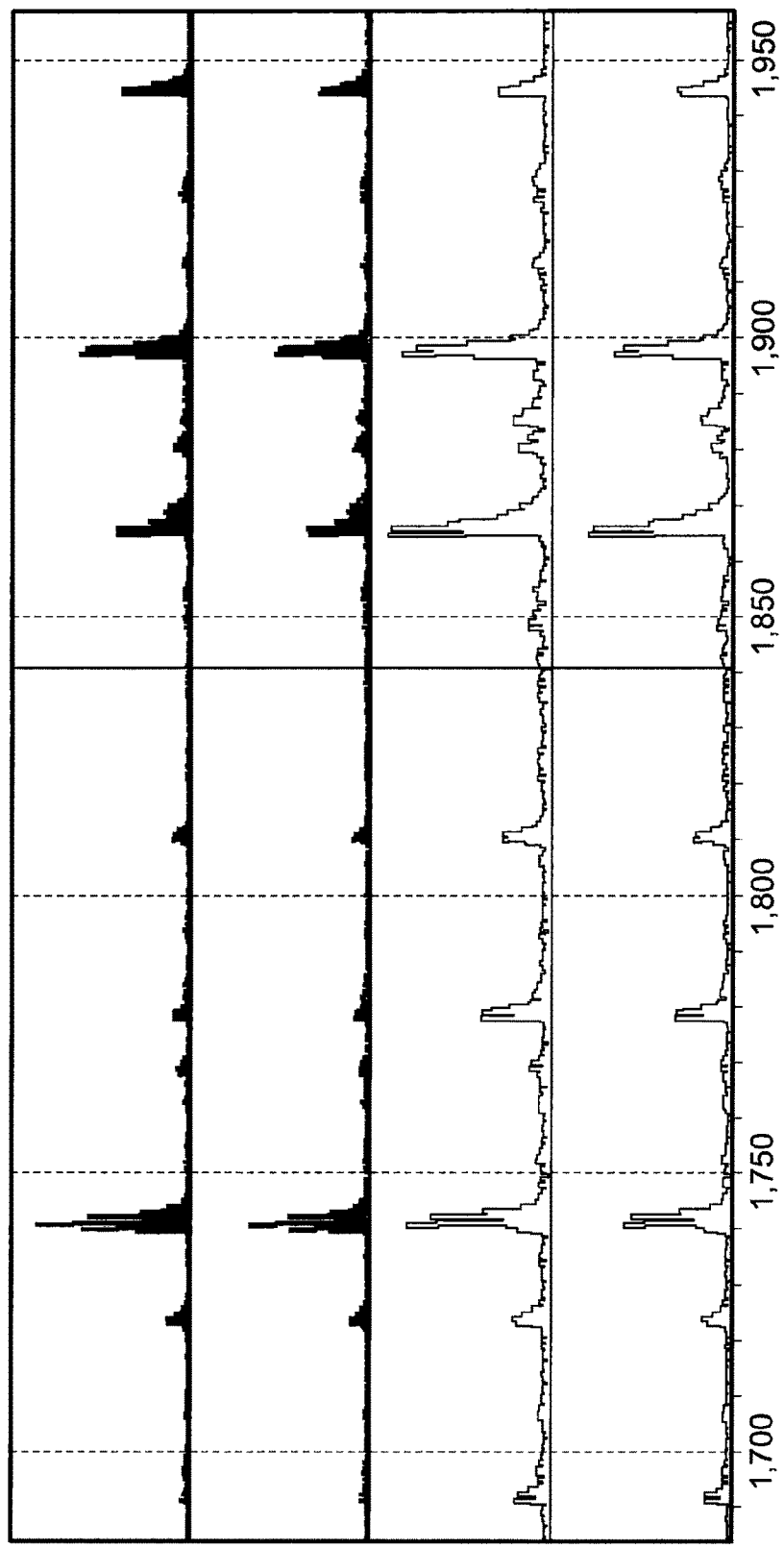
FIG. 5 shows reproducibility of individually processed serum samples. MALDI O-TOF MS spectra of two ovarian cancer serum replicates (top 2 spectra) and two healthy serum replicates (bottom 2 spectra) processed using ProXPRESSION™ Biomarker Enrichment Kits. Display shows zoom of reproducibility in the 1700-1950 Da range. Intensity cv's were below 10%.

Progenesis PG600 software (NonLinear Dynamics, Newcastle, UK) was used to process and analyze the OTOF mass spectral data. Raw spectra from the OTOF were directly loaded into the PG600 program using the prOTOF loader program. Binning was set at 4. Analyses were performed to find discriminant markers between the following groups: Healthy vs all cancer; healthy vs high CA125; healthy vs low CA125 and healthy vs stage I cancer. For the initial analysis, the stringency parameters for biomarker selection were set to include peaks with an average quantity threshold of 75 or greater (higher intensity peaks, to facilitate subsequent sequence identification by tandem MS) and Pvalues of 0.01 or less. Subsequent analyses were performed with peak intensity stringency of <50 or 0 and a Pvalue of 0.01 or less. These parameters ensured the detection of differently expressed peaks that were highly significant. Once the putative peaks were detected, classification models were developed using flexible discriminant analysis and the R statistical package (35). The flexible discriminant analysis algorithm determined non-linear decision boundaries that were better able to separate classes. This resulted in a classification technique that was more powerful for high dimensional data with complex inter-relationships. Using independent stratified balanced random sampling, the data were split into a training set and test set. The training set was used to build a classifier model and this model was evaluated on the test set. The classifier classified test cases as Healthy or Diseased and these data were then used to create ROC curves. Monte Carlo cross validation of training and test sets was used (36, 37). For this validation, the results of 100 runs of the sampling and classifier modeling procedure were averaged together to create the final ROC curve. Eluted samples were then concentrated and desalted on ZipPlates™ (Millipore) according to manufacturer's instructions. Final samples to be analyzed by mass spectrometry were eluted directly onto prOTOF MALDI Chip Targets. When processed with the carrier protein-based biomarker enrichment protocol, serum samples routinely generated highly reproducible peptide profiles with intensity CV's of 5-10%, on average (FIG. 5).

Identification of mass spectra peaks corresponding to biomarkers was performed by data analysis using TOFworks Peptide Mass Fingerprinting software (provided with prOTOF200 Mass spectrometer, PerkinElmer, Boston, Mass.) followed by Progenesis™ PG600 Biomarker Discovery software (Nonlinear Dynamics, Durham, N.C.).

FIG. 1 shows mass spectrographs for peptides isolated from (A) normal serum samples and (B) serum samples corresponding to high CA-125 levels. Also shown is a (C) difference spectrum based on (A) and (B).

Tables 1 and 2 below include data corresponding to peaks that differ between high CA-125 levels vs. normal and low CA-125 levels vs. normal, respectively. Included are the peak no., which identifies each relevant peak in the subject mass spectrum, the total ion current (TIC) difference, the TIC fold difference, as well as statistical information including standard deviations and p values.

TABLE 1

High CA-125 vs. Normal serum samples

| Peak No | m/z | TIC Diff | TIC Fold | Std Dev 1 | Std Dev 2 | p Value |
|---|---|---|---|---|---|---|
| 11 | 991.67 | −108.99 | −3.32 | 38.68 | 115.05 | 0.0000000 |
| 14 | 1015.67 | −37.02 | −1.85 | 38.52 | 57.78 | 0.0000000 |
| 28 | 1690.94 | 54.07 | 1.95 | 74.16 | 29.93 | 0.0000000 |
| 30 | 1739.93 | 93.71 | 2.63 | 113.22 | 41.74 | 0.0000000 |
| 31 | 1777.97 | 98.75 | 1.93 | 134.05 | 58.77 | 0.0000000 |
| 33 | 1865.01 | 293.78 | 1.95 | 383.22 | 162.22 | 0.0000000 |
| 37 | 1896.04 | 142.61 | 1.78 | 200.75 | 102.30 | 0.0000000 |
| 44 | 2021.11 | 62.74 | 1.47 | 115.57 | 61.73 | 0.0000000 |
| 48 | 2081.58 | 71.43 | 1.64 | 170.72 | 50.96 | 0.0000000 |
| 52 | 2209.08 | 112.54 | 2.77 | 167.52 | 40.93 | 0.0000000 |
| 58 | 2582.35 | −144.37 | −3.63 | 54.57 | 95.57 | 0.0000000 |
| 59 | 2659.27 | −103.40 | −2.21 | 115.66 | 127.62 | 0.0000000 |
| 63 | 2882.55 | −105.11 | −1.90 | 46.38 | 74.22 | 0.0000000 |
| 64 | 2898.54 | −43.31 | −2.09 | 26.43 | 46.55 | 0.0000000 |
| 65 | 2989.49 | −65.22 | −2.33 | 41.71 | 104.72 | 0.0000000 |
| 66 | 3027.57 | −47.63 | −2.70 | 15.87 | 34.09 | 0.0000000 |
| 71 | 3157.06 | 103.72 | 1.48 | 226.02 | 150.28 | 0.0000000 |
| 72 | 3239.55 | −190.68 | −2.19 | 121.58 | 204.62 | 0.0000000 |
| 73 | 3263.12 | 92.50 | 3.77 | 112.19 | 16.16 | 0.0000000 |
| 77 | 3521.76 | −97.78 | −1.61 | 115.60 | 124.33 | 0.0000000 |
| 80 | 3679.98 | −16.63 | −1.23 | 49.27 | 42.84 | 0.0000143 |
| 82 | 3769.18 | −33.92 | −1.52 | 41.54 | 44.05 | 0.0000000 |
| 83 | 3812.89 | −74.10 | −1.59 | 82.93 | 91.93 | 0.0000000 |
| 85 | 3953.98 | −34.41 | −1.63 | 40.90 | 43.27 | 0.0000000 |
| 88 | 4280.14 | −43.01 | −1.46 | 87.91 | 99.89 | 0.0000000 |
| 91 | 4473.19 | −57.48 | −2.09 | 51.94 | 72.54 | 0.0000000 |
| 96 | 5901.61 | 489.49 | 2.32 | 691.38 | 257.41 | 0.0000000 |

TABLE 2

Low CA-125 Levels vs. Normal serum samples

| Peak No | m/z | TIC Diff | TIC Fold | Std Dev 1 | Std Dev 2 | p Value |
|---|---|---|---|---|---|---|
| 11 | 991.67 | −89.92 | −2.91 | 38.68 | 101.10 | 0.0000000 |
| 28 | 1690.94 | 60.57 | 2.20 | 74.16 | 27.53 | 0.0000000 |
| 30 | 1739.93 | 93.19 | 2.61 | 113.22 | 45.64 | 0.0000000 |
| 31 | 1777.97 | 110.31 | 2.16 | 134.05 | 55.48 | 0.0000000 |
| 33 | 1865.01 | 319.61 | 2.12 | 383.22 | 171.43 | 0.0000000 |
| 37 | 1896.04 | 145.69 | 1.81 | 200.75 | 100.26 | 0.0000000 |
| 41 | 1943.92 | 65.36 | 1.24 | 342.54 | 224.99 | 0.0093354 |
| 44 | 2021.11 | 70.21 | 1.56 | 115.57 | 71.88 | 0.0000000 |
| 48 | 2081.58 | 83.44 | 1.83 | 170.72 | 60.08 | 0.0000000 |
| 52 | 2209.08 | 118.13 | 3.04 | 167.52 | 39.29 | 0.0000000 |
| 58 | 2582.35 | −116.39 | −3.12 | 54.57 | 87.19 | 0.0000000 |
| 59 | 2659.27 | −66.80 | −1.78 | 115.66 | 117.21 | 0.0000000 |
| 63 | 2882.55 | −102.19 | −1.87 | 46.38 | 94.81 | 0.0000000 |
| 64 | 2898.54 | −37.04 | −1.93 | 26.43 | 64.51 | 0.0000000 |
| 65 | 2989.49 | −54.84 | −2.12 | 41.71 | 103.38 | 0.0000000 |
| 71 | 3157.06 | 104.57 | 1.48 | 226.02 | 166.98 | 0.0000000 |
| 72 | 3239.55 | −163.16 | −2.02 | 121.58 | 221.36 | 0.0000000 |
| 73 | 3263.12 | 93.35 | 3.87 | 112.19 | 23.70 | 0.0000000 |
| 77 | 3521.76 | −84.51 | −1.52 | 115.60 | 134.61 | 0.0000000 |
| 80 | 3679.98 | −12.50 | −1.17 | 49.27 | 46.15 | 0.0011286 |
| 82 | 3769.18 | −27.82 | −1.42 | 41.54 | 47.61 | 0.0000000 |
| 83 | 3812.89 | −62.81 | −1.50 | 82.93 | 99.28 | 0.0000000 |
| 85 | 3953.98 | −34.04 | −1.62 | 40.90 | 47.31 | 0.0000000 |
| 88 | 4280.14 | −35.72 | −1.38 | 87.91 | 112.25 | 0.0000062 |
| 91 | 4473.19 | −50.36 | −1.95 | 51.94 | 72.92 | 0.0000000 |
| 96 | 5901.61 | 436.23 | 2.03 | 691.38 | 335.36 | 0.0000000 |

Figure 2:
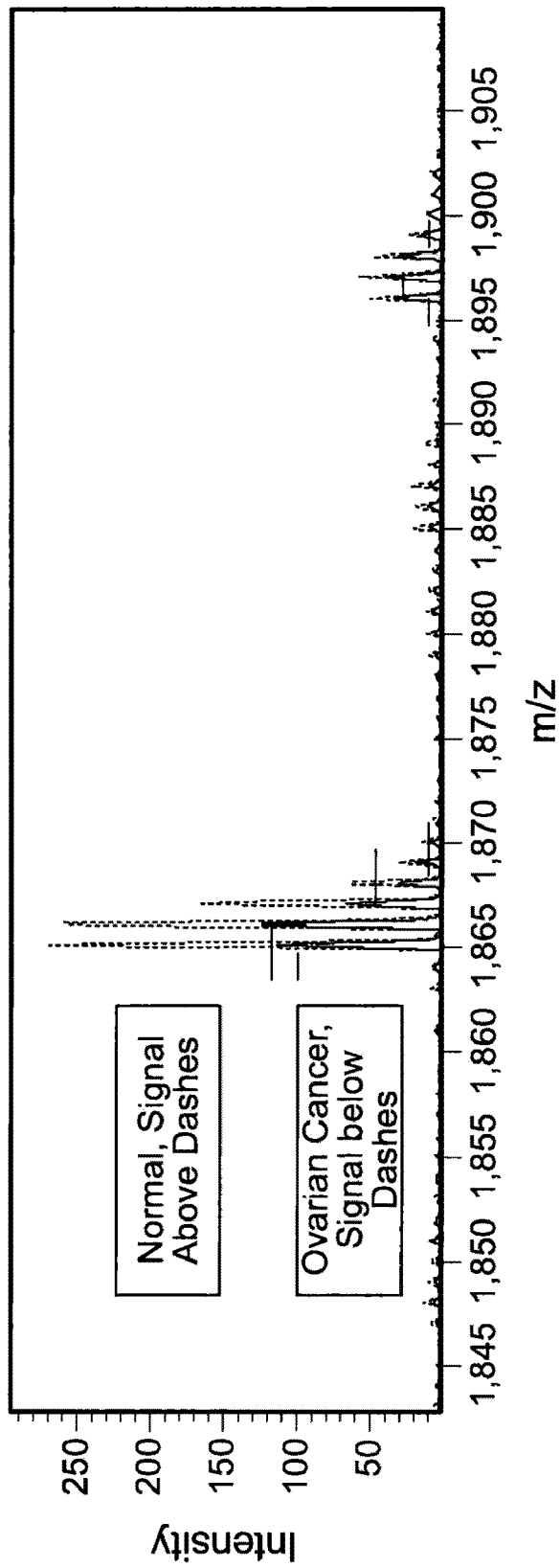
FIG. 2 shows differences in the peptide m/z range of 1850-1890.
Figure 3:
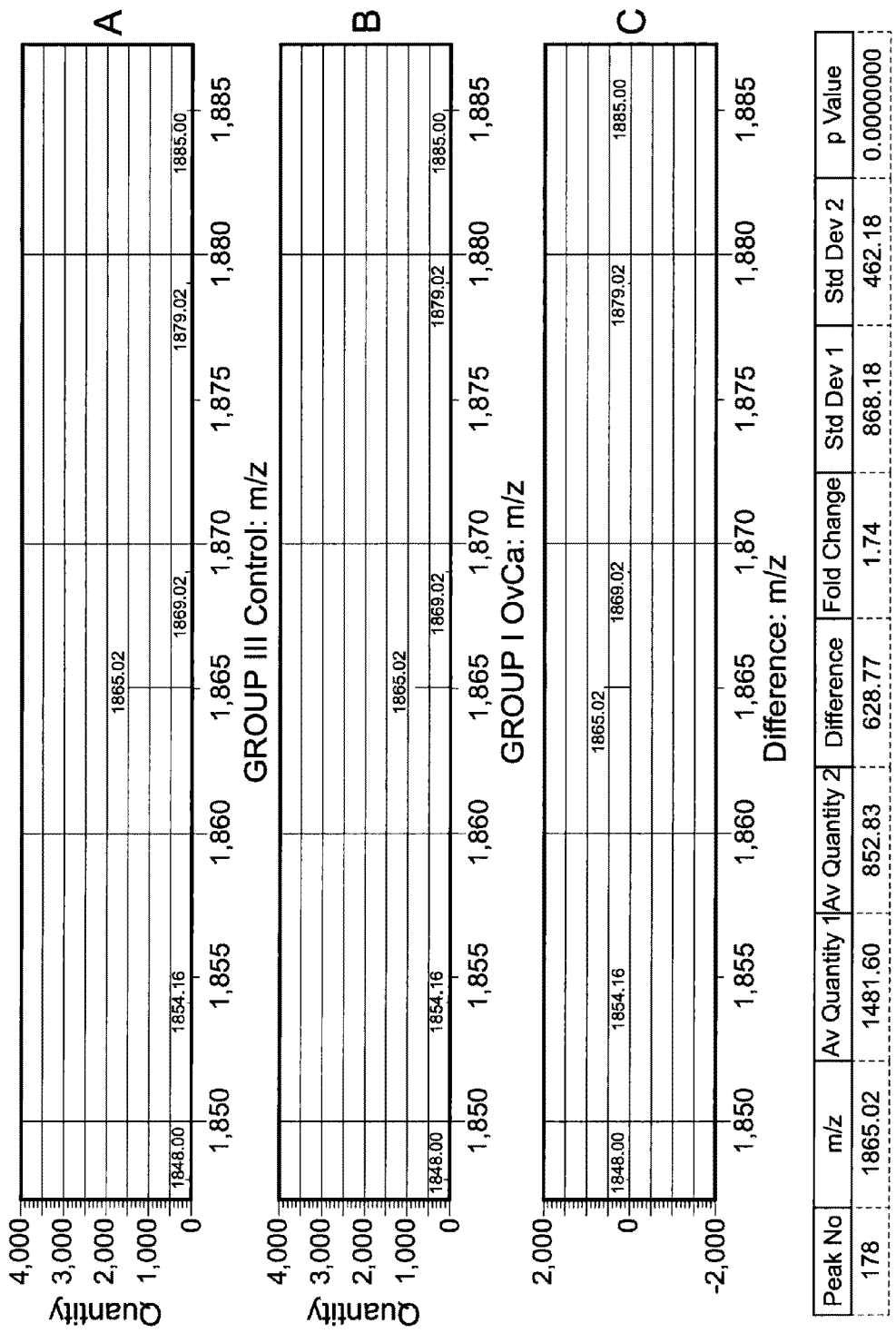
FIG. 3 shows several peaks having about two fold greater signal intensity in normal samples in comparison to ovarian cancer samples.
Figure 4:
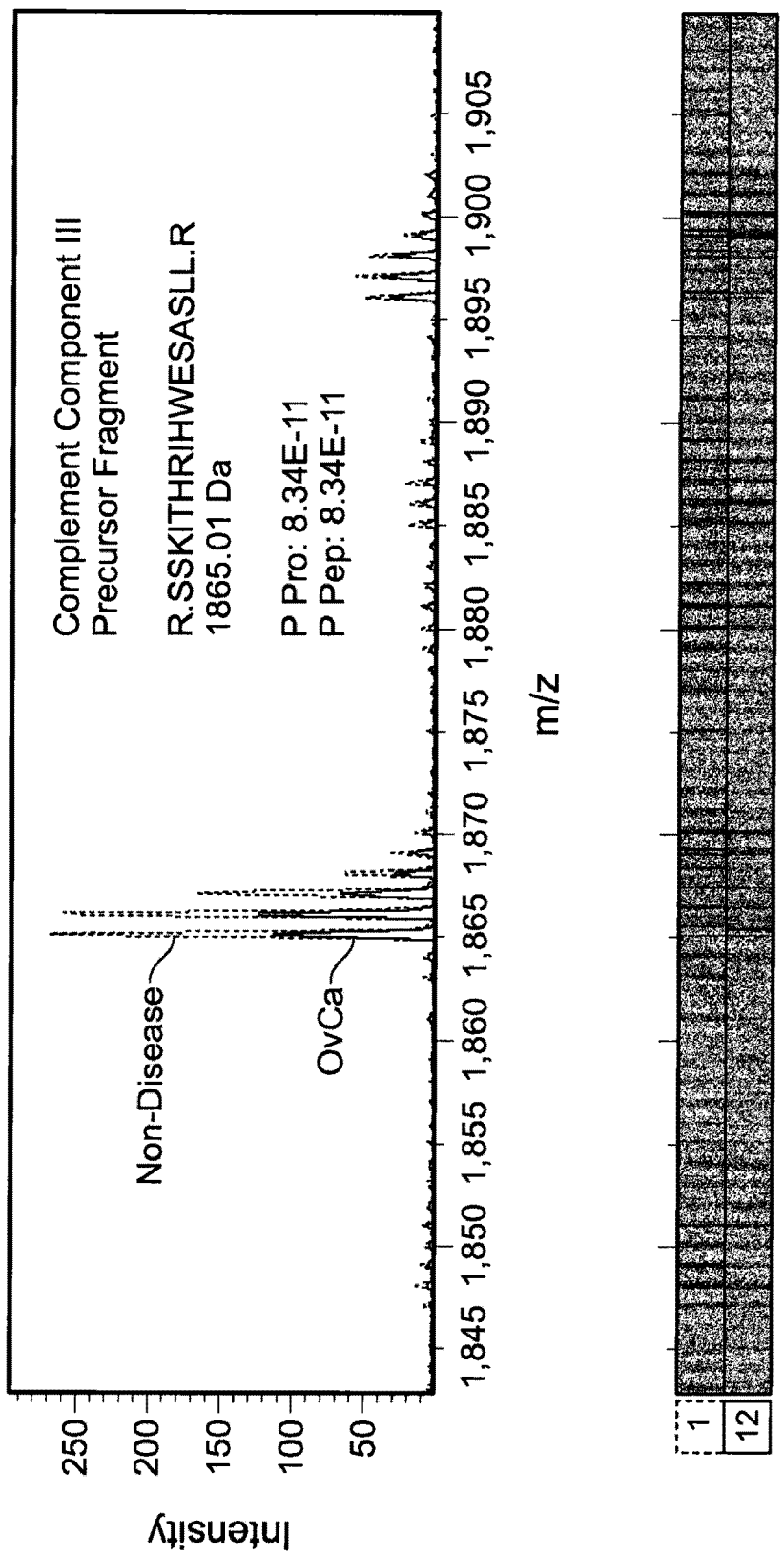
FIG. 4 shows peak no 178, having a m/z of 1865.02, an intensity of about 1481.6 in normal samples, and having amino acid sequence SSKITHRIHWESASLLR (SEQ ID NO:1), which corresponds to a portion of Complement Component II Precursor (NCBI Accession #NP_000055).

As a more focused view on differences between mass spectra, FIG. 2 shows differences in the peptide m/z range of 1850-1890. FIG. 3 shows several peaks having about two fold greater signal intensity in normal samples in comparison to ovarian cancer samples. For example, FIG. 3 shows 5 such peaks in the range of 1865 and 1879 m/z, and 3 peaks in the range of 1895 and 1900 m/z. Within this m/z range, a peptide having m/z 1865.02 was observed to differ significantly between normal and ovarian cancer samples, as is shown in FIG. 4. FIG. 4 identifies this peptide as peak no 178, having a m/z of 1865.02, an intensity of about 1481.6 in normal samples, an intensity of about 852.63 in ovarian cancer samples, with a difference of 628.77, which represents a 1.74-fold lower signal associated with this peptide in ovarian cancer samples relative to normal samples.

To determine amino acid sequences of peptides having differential presence in normal vs. ovarian cancer samples, samples were subjected to MS/MS sequencing using a Finnigan LTQ FT high performance ion trap—Fourier Transform mass spectrometer. As is shown in FIG. 5, the amino acid sequence for peptide m/z 1865.02 was determined to be SSKITHRIHWESASLLR (SEQ ID NO:1), which corresponds to a portion of Complement Component II Precursor (accession #NP_000055).

Figure 6:
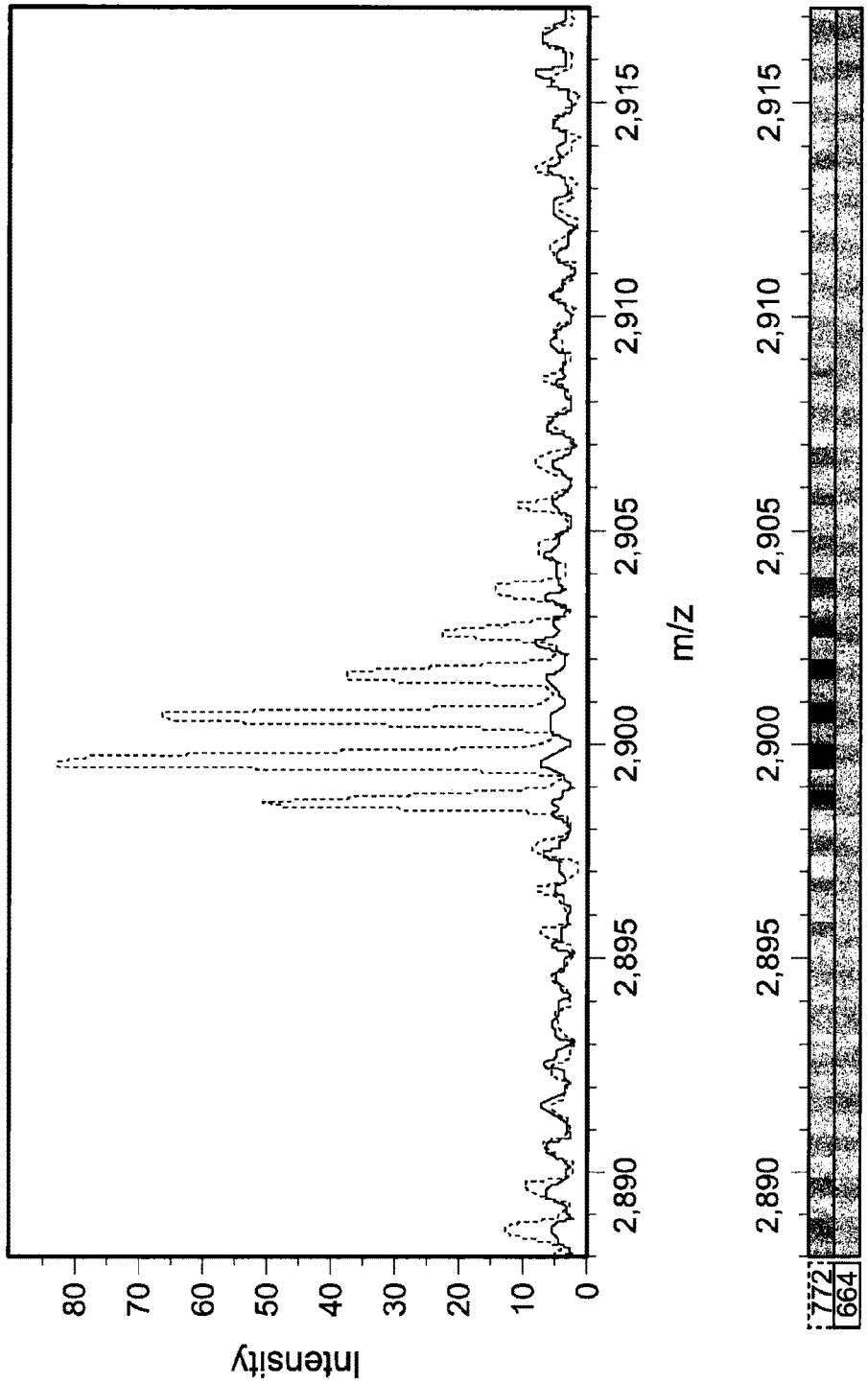
FIG. 6 shows differential expression of transthyretin fragment at m/z 2898.54. Overlaid mass spectral traces from representative ovarian cancer and healthy samples. Zoom of m/z 2890 to 2915 area. Top trace=ovarian cancer sample; bottom trace=non-cancer reference sample.
Figure 7:
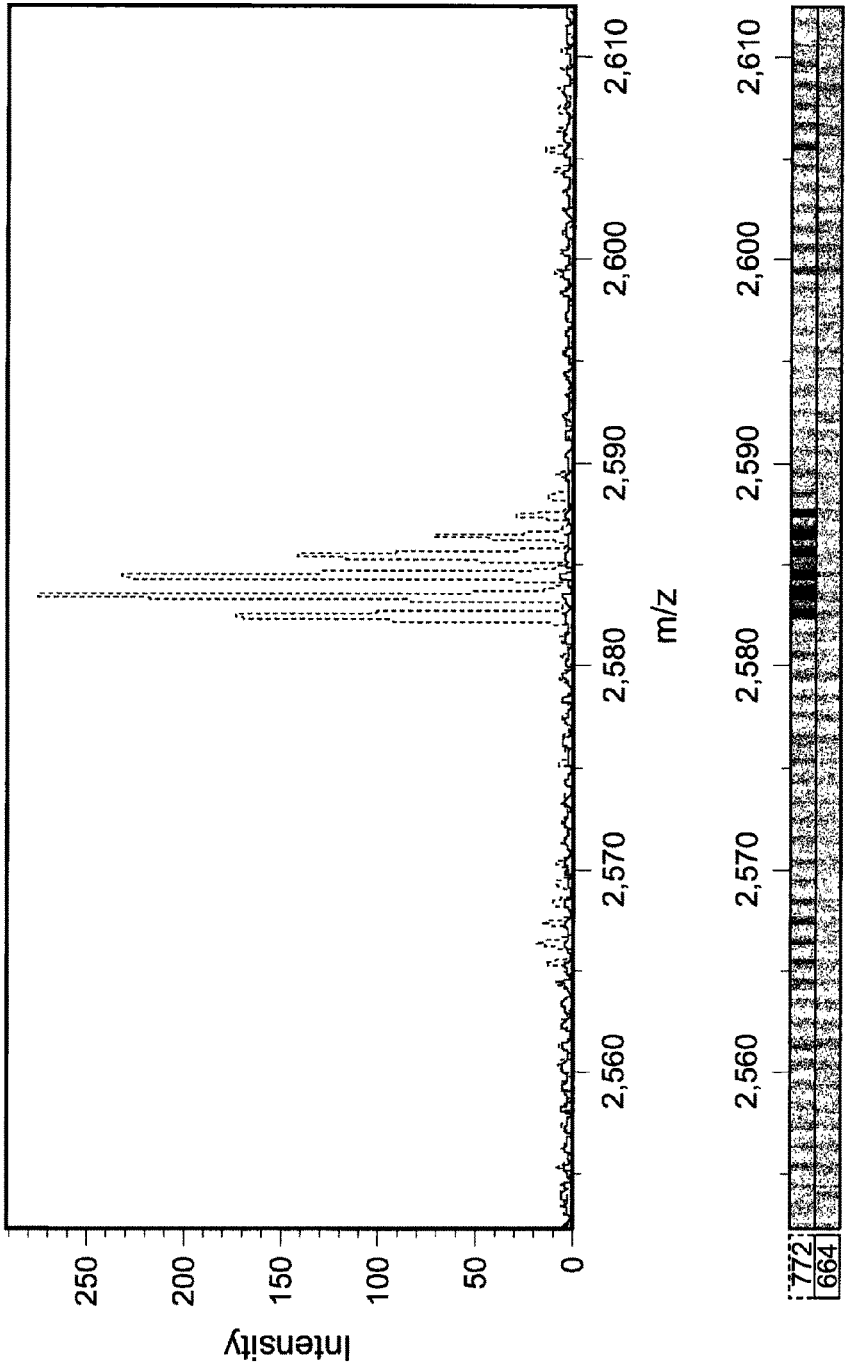
FIG. 7 shows differential expression of plasma kallikrein-sensitive glycoprotein fragment at m/z 2582.35. Overlaid spectral traces from representative ovarian cancer and healthy samples. Zoom of m/z 2550 to 2610 area. Top trace=ovarian cancer sample; bottom trace=non-cancer reference sample.
Figure 8:
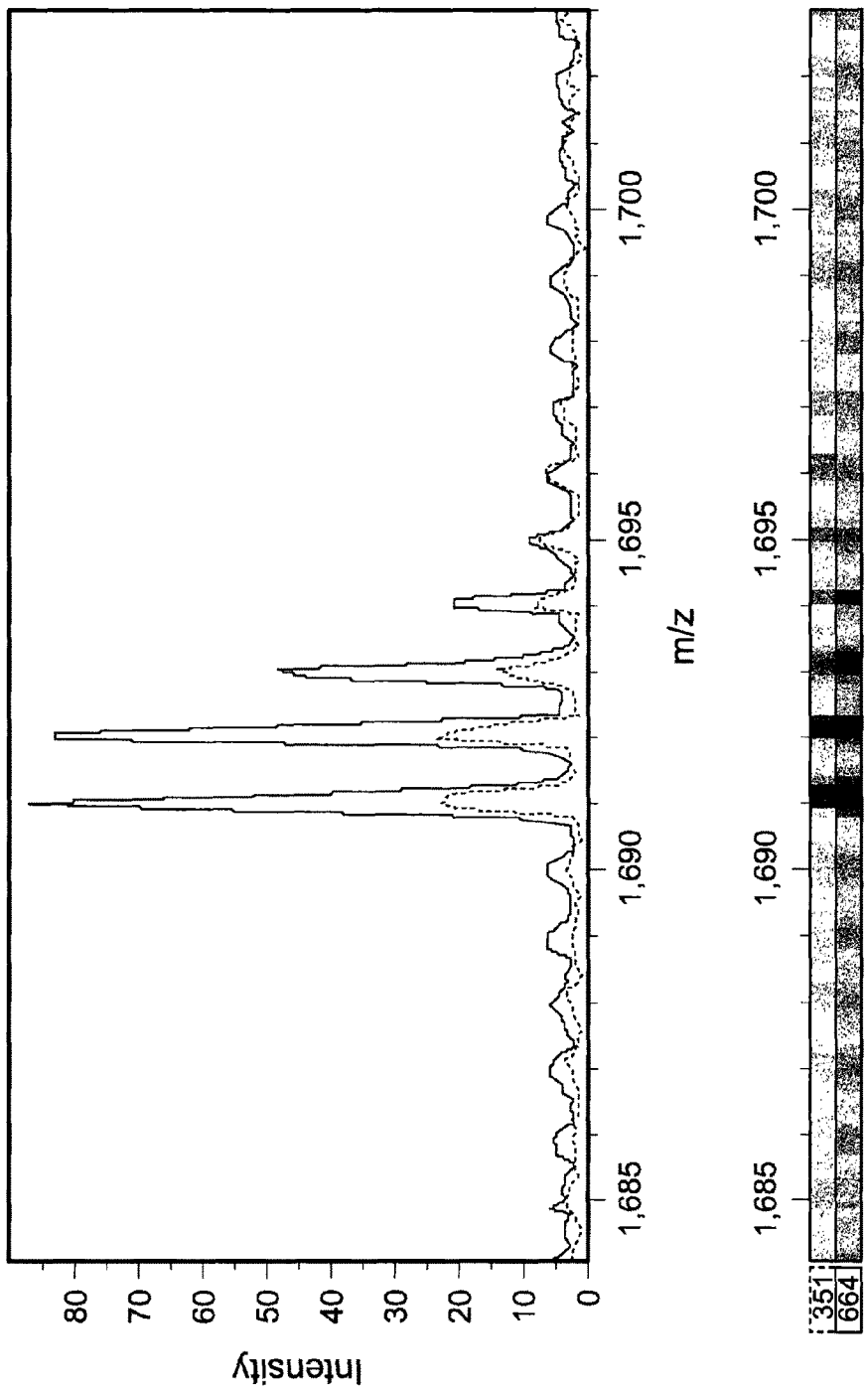
FIG. 8 shows differential expression of complement component precursor 3 fragment at m/z 1690.94. Overlaid spectral traces from representative ovarian cancer and healthy samples. Zoom of m/z 1685 to 1700 area. Top trace=non-cancer reference sample; bottom trace=ovarian cancer sample.

Other discriminating peptides identified by the initial analysis of spectral profiles from four different groups: 1) healthy vs all cancer (low CA125+high CA125), 2) healthy vs low CA125, 3) healthy vs high CA125, and 4) healthy vs stage I cancer, are shown in Table 3. The identities of these peptides included multiple peptide hits from complement component 3 and inter-alpha (globulin) inhibitor H4 and single peptides from complement component 4A, transthyretin and fibrinogen Table 6. Because the analysis parameters were set to screen out low intensity masses, it is not surprising that these fragments are derived from relatively abundant serum proteins. However, because these peptides are derived from highly abundant resident proteins, does not mean that they are either non-specific or are themselves highly abundant. Examples of overlaid disease and normal spectra are shown in FIGS. 6-8; putative marker expression ranged from ca 3.6-fold increase to a 2.6-fold decrease in cancer samples (Table 3). To test the discriminating power of these markers, flexible discriminant analysis classification models were built and tested. The discriminating power of the 9 marker model had specificity and sensitivity averaging 93% and 93%, respectively (Table 7).

Expanding the analysis, stringency parameters were reduced slightly to allow the inclusion of lower intensity discriminating masses. The results of this analysis yielded a set of 4 markers shown in Table 4. Two of the peptides at m/z 1739.9 and 2582.35 were also in the initial set of 9 and the remaining 2 masses at m/z 2659.27 and 2989.49 remain unidentified. The 4 marker model delivered equivalent (93%) sensitivity and enhanced (97%) specificity versus the 9 marker model (Table 7). In an effort to discover lower abundance discriminating peptides, or peptides not related to coagulation, intensity stringency of the analysis was reduced to 0, keeping the Pvalues at 0.01 or better. Five additional discriminating masses resulted from this analysis (Tables 5 and 7). None of the identified proteins in this set are related to coagulation and all are correlated with or involved in cellular oncogenenesis (casein Kinase 2, transgelin (38-40)), proliferation (keratin 2, LARGE (41-42)) or detoxification of ROS (diamino oxidase (43)) processes. A model created with these 5 markers plus 2 additional markers from the 4 marker set classified the healthy and lowCA125 samples with 77% sensitivity and 85% specificity.

TABLE 3

Ovarian cancer 9 marker model expression values

| Model 9 marker | m/z | Fold Expression | p Value |
|---|---|---|---|
| Healthy vs all cancer | 1690.94 | −2.06 | 0.0000000 |
| | 1739.93 | −2.62 | 0.0000000 |
| | 1777.97 | −2.03 | 0.0000000 |
| | 1865.01 | −2.03 | 0.0000000 |
| | 2021.11 | −1.51 | 0.0000000 |
| | 2582.35 | 3.38 | 0.0000000 |
| | 2898.54 | 2.01 | 0.0000000 |
| | 3027.57 | 2.59 | 0.0000000 |
| | 3239.55 | 2.10 | 0.0000000 |
| Healthy vs high CA125 | 1690.94 | −2.20 | 0.0000000 |
| | 1739.93 | −2.61 | 0.0000000 |
| | 1777.97 | −2.16 | 0.0000000 |
| | 1865.01 | −2.12 | 0.0000000 |
| | 2021.11 | −1.56 | 0.0000000 |
| | 2582.35 | 3.12 | 0.0000000 |
| | 2898.54 | 1.93 | 0.0000000 |
| | 3027.57 | — | 0.0000000 |
| | 3239.55 | 2.02 | 0.0000000 |
| Healthy vs low CA125 | 1690.94 | −1.95 | 0.0000000 |
| | 1739.93 | −2.63 | 0.0000000 |
| | 1777.97 | −1.93 | 0.0000000 |
| | 1865.01 | −1.95 | 0.0000000 |
| | 2021.11 | −1.47 | 0.0000000 |
| | 2582.35 | 3.63 | 0.0000000 |
| | 2898.54 | 2.09 | 0.0000000 |
| | 3027.57 | 2.70 | 0.0000000 |
| | 3239.55 | 2.19 | 0.0000000 |
| Healthy vs Stage I cancer | 1690.94 | −2.38 | 0.0000000 |
| | 1739.93 | −3.23 | 0.0000000 |
| | 1777.97 | −2.61 | 0.0000000 |
| | 1865.01 | −2.46 | 0.0000000 |
| | 2021.11 | 1.92 | 0.0000000 |
| | 2582.35 | 2.70 | 0.0000000 |
| | 2898.54 | 2.56 | 0.0000000 |
| | 3027.57 | 3.71 | 0.0000000 |
| | 3239.55 | 2.35 | 0.0000000 |

TABLE 4

Ovarian cancer 4 marker model expression values

| Model 4 marker | m/z | Fold Expression | p Value |
|---|---|---|---|
| Healthy vs all cancer | 1739.93 | −2.62 | 0.0000000 |
| | 2582.35 | 3.38 | 0.0000000 |
| | 2659.27 | 2.00 | 0.0000000 |
| | 2989.49 | 2.23 | 0.0000000 |
| Healthy vs High CA125 | 1739.93 | −2.61 | 0.0000000 |
| | 2582.35 | 3.12 | 0.0000000 |
| | 2659.27 | 1.78 | 0.0000000 |
| | 2989.49 | 2.12 | 0.0000000 |
| Healthy vs Low CA125 | 1739.93 | −2.63 | 0.0000000 |
| | 2582.35 | 3.63 | 0.0000000 |
| | 2659.27 | 1.90 | 0.0000000 |
| | 2989.49 | 2.33 | 0.0000000 |
| Healthy vs Stage I cancer | 1739.93 | −3.23 | 0.0000000 |
| | 2582.35 | 2.70 | 0.0000000 |
| | 2659.27 | 2.50 | 0.0000000 |
| | 2989.49 | 1.79 | 0.0000000 |

TABLE 5

Ovarian cancer 7 marker model expression values

| Model 7 marker | m/z | Fold Expression | p Value |
|---|---|---|---|
| Healthy vs all cancer | 1739.93 | −2.62 | 0.0000000 |
| | 2582.35 | 3.38 | 0.0000000 |
| | 1966.91 | −1.21 | 0.0000000 |
| | 1041.68 | 1.34 | 0.0000000 |
| | 2115.05 | −1.11 | 0.0137930 |
| | 1224.68 | 1.87 | 0.0000000 |
| | 2345.19 | 2.07 | 0.0000000 |
| Healthy vs High CA125 | 1739.93 | −2.61 | 0.0000000 |
| | 2582.35 | 3.12 | 0.0000000 |
| | 1966.91 | −1.29 | 0.0000000 |
| | 1041.68 | 1.24 | 0.0002921 |
| | 2115.05 | −1.21 | 0.0001184 |
| | 1224.68 | 1.80 | 0.0000000 |
| | 2345.19 | 2.02 | 0.0000000 |
| Healthy vs Low CA125 | 1739.93 | −2.63 | 0.0000000 |
| | 2582.35 | 3.63 | 0.0000000 |
| | 1966.91 | −1.15 | 0.0000009 |
| | 1041.68 | 1.43 | 0.0000000 |
| | 2115.05 | — | — |
| | 1224.68 | 1.94 | 0.0000000 |
| | 2345.19 | 2.11 | 0.0000000 |
| Healthy vs Stage I cancer | 1739.93 | −3.37 | 0.0000000 |
| | 2582.35 | 2.99 | 0.0000000 |
| | 1966.91 | −1.40 | 0.0000000 |
| | 1041.68 | 1.38 | 0.0024583 |
| | 2115.05 | — | — |
| | 1224.68 | 1.97 | 0.0000007 |
| | 2345.19 | 2.55 | 0.0000000 |

TABLE 6

| m/z | peptide sequence | SEQ ID NO: | P (pep) | identity |
|---|---|---|---|---|
| 1966.91 | T.DVNTHRPREYWDYE S.H | 2 | 3.01794E-05 | gi\|29570791\|ref\|NP_808227.1\| casein kinase II alpha 1 subunit isoform a [Homo sapiens] |
| 1041.68 | L.NVKVDPEIQ.N | 3 | 4.18765E-05 | gi\|47132620\|ref\|NP_000414.2\| keratin 2a [Homo sapiens] [MASS = 65432] |
| 2115.05 | A.REGADVIVNCTGVW AGALQR.D | 4 | 0.000610972 | gi\|21536470\|ref\|NP_001908.2\| D-amino-acid oxidase [Homo sapiens] [MASS = 39496] |

TABLE 6-continued

| m/z | peptide sequence | SEQ ID NO: | P (pep) | identity |
|---|---|---|---|---|
| 1224.68 | L.KPRVSWIPNK.H | 5 | 2.54E-04 | gi\|33285008\|ref\|NP_689525.2\| glycosyltransferase-like 1B [Homo sapiens][MASS = |
| 2345.19 | Q.M*GTNRGASQAGM*TGYGM*PRQIL.- | 6 | 1.97832E-05 | gi\|4507357\|ref\|NP_003555.1\| transgelin 2 [Homo sapiens] [MASS = 22391] |
| 1626.88 | R.NGFKSHALQLNNRQ.I | 7 | 4.37E-10 | gi\|67190748\|ref\|NP_009224.2\| complement component 4A preproprotein [Homo sapiens] |
| 1739.93 | R.NGFKSHALQLNNRQI.R | 8 | 9.96E-09 | gi\|67190748\|ref\|NP_009224.2\| complement component 4A preproprotein [Homo sapiens] |
| 1690.94 | S.KITHRIHWESASLL.R | 9 | 5.40E-10 | gi\|4557385\|ref\|NP_000055.1\| complement component 3 precursor [Homo sapiens][MA |
| 1865.01 | R.SSKITHRIHWESASLL.R | 10 | 1.35E-09 | gi\|4557385\|ref\|NP_000055.1\| complement component 3 precursor [Homo sapiens][MA |
| 2021.11 | R.SSKITHRIHWESASLLR.S | 11 | 1.13E-10 | gi\|4557385\|ref\|NP_000055.1\| complement component 3 precursor [Homo sapiens][MA |
| 1777.97 | S.SKITHRIHWESASLL.R | 12 | 3.07E-11 | gi\|4557385\|ref\|NP_000055.1\| complement component 3 precursor [Homo sapiens][MA |
| 3027.57 | N.FRPGVLSSRQLGLPGPPDVPDHAAYHPF.R | 13 | 2.97007E-06 | gi-31542984\|ref\|NP_002209.2\| inter-alpha (globulin) inhibitor H4 (plasma Kallikrein-sensitive glyco |
| 1218.66 | P.PDVPDHAAYHP.F | 14 | 0.001961118 | gi\|31542984\|ref\|NP_002209.2\| inter-alpha (globulin) inhibitor H4 (plasma Kallikrein-sensitive glyco |
| 2582.35 | R.NVHSGSTFFKYYLQGAKIPKPEA.S | 15 | 3.9553E|06 | gi\|31542984\|ref\|NP_002209.2\| inter-alpha (globulin) inhibitor H4 (plasma Kallikrein-sensitive glyco |
| 3272.64 | R.MNFRPGVLSSRQLGLPGPPDVPDHAAYHPF.R | 16 | 2.01125E-06 | gi\|31542984\|ref\|NP_002209.2\| inter-alpha (globulin) inhibitor H4 (plasma Kallikrein-sensitive glyco |
| 2669.41 | R.NVHSGSTFFKYYLQGAKIPKPEAS.F | 17 | 0.000168959 | gi\|31542984\|ref\|NP_002209.2\| inter-alpha (globulin) inhibitor H4 (plasma Kallikrein-sensitive glyco |
| 2882.55 | R.GHRPLDKKREEAPSLRPAPPPISGGGY.R | 18 | 3.47647E-05 | gi\|70906435\|ref\|NP_005132.2\| fibrinogen, beta chain preproprotein [Homo sapiens] |
| 3116.53 | R.GKSSSYSKQFTSSTSYNRGDSTFESKSY.K | 19 | 8.10375E-07 | gi\|11761629\|ref\|NP_068657.1\| fibrinogen, alpha chain isoform alpha preproprotein [Homo sapiens][MA |
| 3239.55 | K.SYKMADEAGSEADHEGTHSTKRGHAKSRP | 20 | 0.001406444 | gi\|11761629\|ref\|NP_068657.1\| fibrinogen, alpha chain |

TABLE 6-continued

| m/z | peptide sequence | SEQ ID NO: | P (pep) | identity |
|---|---|---|---|---|
| | V.R | | | isoform alpha preproprotein [Homo sapiens][MA |
| 1829.85 | K.SSSYSKQFTSSTSYNR.G | 21 | 5.83E_14 | gi|11761629|ref|NP_068657.1| fibrinogen, alpha chain isoform alpha preproprotein [Homo sapiens][MA |
| 2898.54 | G.PRRYTIAALLSPYSYSTTAVVTNPKE.- | 22 | 0.001732434 | gi|4507725|ref|NP_000362.1| transthyretin [Homo sapiens] [MASS = 15887] |

TABLE 7

Classification power* of the 9, 4 and 7 marker models

| Model | m/z | % Sensitivity | % Specificity | AUC | % Prediction error |
|---|---|---|---|---|---|
| 9 marker | 1690.94<br>1739.93<br>1777.97<br>1865.01<br>2021.11<br>2582.35<br>2898.54<br>3027.57<br>3239.55 | 93 +/- 2.5 | 93 +/- 1.7 | 98 +/- 0.7 | 7.0 +/- 1.3 |
| 4 marker | 1739.93<br>2582.35<br>2659.27<br>2989.49 | 93 +/- 2.0 | 97 +/- 0.8 | 98 +/- 0.6 | 4.3 +/- 0.7 |
| 7 marker | 1739.93<br>2582.35<br>1966.91<br>1041.68<br>2115.05<br>1224.68<br>2345.19 | 77 +/- 4.3 | 85 +/- 3.0 | 87 +/- 1.9 | 16.9 =/- 1.9 |

*Healthy vs Low CA125 samples

TABLE 8

Listing of observed protein fragments of Inter-Alpha (globulin) Inhibitor H4 (Plasma Kallikrein-Sensitive Glycoprotein) [P Protein = 2.71E-13]

| SEQ ID NO: | Observed Fragment | Fragment MW (Da) | P (Pep) |
|---|---|---|---|
| 23 | K.PEASFSPR.R | 890.44 | 7.29E-04 |
| 24 | I.PKPEASFSPR.R | 1115.58 | 5.26E-04 |
| 25 | P.PDVPDHAAYHPF.R | 1365.62 | 1.11E-03 |
| 26 | G.PPDVPDHAAYHPF.R | 1462.67 | 1.45E-03 |
| 27 | P.GPPDVPDHAAYHPF.R | 1519.7 | 1.20E-03 |
| 28 | L.PGPPDVPDHAAYHPF.R | 1616.75 | 2.59E-08 |
| 28 | L.PGPPDVPDHAAYHPF.R | 1616.75 | 8.53E-04 |
| 29 | F.KYYLQGAKIPKPEA.S | 1752.97 | 1.09E-04 |
| 30 | Y.YLQGAKIPKPEASFSPR.R | 1889.03 | 3.41E-07 |
| 31 | T.FFKYYLQGAKIPKPEA.S | 1900.04 | 9.07E-08 |
| 32 | T.FFKYYLQGAKIPKPEAS.F | 1987.07 | 6.05E-09 |
| 33 | K.YYLQGAKIPKPEASFSPR.R | 2052.09 | 9.15E-10 |
| 33 | K.YYLQGAKIPKPEASFSPR.R | 2052.09 | 3.09E-07 |
| 34 | H.SGSTFFKYYLQGAKIPKPEAS.F | 2319.2 | 5.56E-07 |
| 35 | V.HSGSTFFKYYLQGAKIPKPEA.S | 2369.23 | 8.10E-05 |
| 36 | P.GVLSSRQLGLPGPPDVPDHAAYHPF.R | 2627.34 | 8.04E-13 |
| 17 | R.NVHSGSTFFKYYLQGAKIPKPEAS.F | 2669.37 | 7.81E-05 |
| 37 | R.PGVLSSRQLGLPGPPDVPDHAAYHPF.R | 2724.39 | 1.62E-11 |
| 38 | H.SGSTFFKYYLQGAKIPKPEASFSPR.R | 2806.46 | 2.71E-13 |
| 39 | N.FRPGVLSSRQLGLPGPPDVPDHAAYHP.F | 2880.49 | 7.05E-04 |
| 13 | N.FRPGVLSSRQLGLPGPPDVPDHAAYHPF.R | 3027.56 | 2.97E-06 |
| 40 | R.NVHSGSTFFKYYLQGAKIPKPEASFSPR.R | 3156.63 | 1.91E-09 |
| 16 | R.MNFRPGVLSSRQLGLPGPPDVPDHAAYHPF.R | 3272.64 | 2.01E-06 |
| 41 | R.M*NFRPGVLSSRQLGLPGPPDVPDHAAYHPF.R | 3288.64 | 2.37E-05 |
| 42 | R.QAGAAGSRMNFRPGVLSSRQLGLPGPPDVPDHAAYHPF.R | 3970.99 | 1.58E-05 |
| 43 | R.QAGAAGSRM*NFRPGVLSSRQLGLPGPPDVPDHAAYHPF.R | 3986.98 | 2.66E-04 |
| 44 | W.NRQAGAAGSRM*NFRPGVLSSRQLGLPGPPDVPDHAAYHPF.R | 4257.13 | 1.08E-03 |

TABLE 9

List of proteins (fragments) identified in carrier protein-bound serum fraction from ovarian cancer samples

| NIH Protein Database Reference and Protein name | P (pro) | Protein MW |
|---|---|---|
| gi\|10518497\|ref\|NP_005609.2\|delta-like 1 [*Homo sapiens*] [MASS = 77985] | 5.52E−03 | 77933.5 |
| gi\|11761629\|ref\|NP_068657.1\|fibrinogen, alpha chain isoform alpha preproprotein [*Homo sapiens*] [MA | 4.13E−11 | 69713.8 |
| gi\|13540565\|ref\|NP_110415.1\|dendritic cell-specific transmembrane protein [*Homo sapiens*] | 2.10E−03 | 53357.8 |
| gi\|13562114\|ref\|NP_110400.1\|beta tubulin 1, class VI [*Homo sapiens*] [MASS = 5032 | 3.08E−05 | 50294.6 |
| gi\|13654274\|ref\|NP_112485.1\|fumarylacetoacetate hydrolase domain containing 1 isoform 2 [*Homo sapiens*] | 4.24E−03 | 24826.7 |
| gi\|13775222\|ref\|NP_112590.1\|MAX dimerization protein 3 [*Homo sapiens*] [MASS = 2 | 1.80E−03 | 23463.1 |
| gi\|14165461\|ref\|NP_114174.1\|nuclear prelamin A recognition factor isoform b [*Homo sapiens*] | 2.75E−03 | 56125.3 |
| gi\|14210536\|ref\|NP_115914.1\|tubulin, beta 6 [*Homo sapiens*] [MASS = 49857] | 2.50E−05 | 49825.0 |
| gi\|15149463\|ref\|NP_149130.1\|caldesmon 1 isoform 4 [*Homo sapiens*] [MASS = 64256] | 2.02E−04 | 64217.9 |
| gi\|15431310\|ref\|NP_000517.2\|keratin 14 [*Homo sapiens*] [MASS = 51621] | 4.13E−03 | 51589.5 |
| gi\|15529990\|ref\|NP_219491.1\|granzyme H [*Homo sapiens*] [MASS = 27315] | 2.47E−03 | 27297.4 |
| gi\|15618995\|ref\|NP_258259.1\|keratin 6 irs [*Homo sapiens*] [MASS = 57291] | 5.35E−05 | 57256.1 |
| gi\|16506285\|ref\|NP_443723.1\|ankyrin repeat domain 30A [*Homo sapiens*] [MASS = 15 | 6.08E−03 | 152680.7 |
| gi\|16507198\|ref\|NP_065894.1\|zinc finger protein 291 [*Homo sapiens*] [MASS = 1581 | 5.90E−03 | 158056.7 |
| gi\|16751921\|ref\|NP_444513.1\|dermcidin precursor [*Homo sapiens*] [MASS = 11284] | 5.58E−07 | 11276.8 |
| gi\|16753233\|ref\|NP_006280.2\|talin 1 [*Homo sapiens*] [MASS = 269666] | 1.39E−07 | 269497.3 |
| gi\|17318569\|ref\|NP_006112.2\|keratin 1 [*Homo sapiens*] [MASS = 66066] | 1.36E−04 | 66027.0 |
| gi\|17978481\|ref\|NP_536338.1\|vacuolar protein sorting 16 isoform 3 [*Homo sapiens*] | 6.55E−03 | 78250.6 |
| gi\|17986283\|ref\|NP_006000.2\|tubulin, alpha 3 [*Homo sapiens*] [MASS = 50135] | 2.66E−12 | 50103.7 |
| gi\|19923466\|ref\|NP_057417.2\|splicing coactivator subunit SRm300 [*Homo sapiens*] | 3.20E−03 | 299494.7 |
| gi\|19923723\|ref\|NP_036556.2\|ribosomal protein S6 kinase, 52 kDa, polypeptide 1 [*Homo sapiens*] | 1.40E−05 | 118608.7 |
| gi\|19923903\|ref\|NP_612382.1\|myeloid-associated differentiation marker [*Homo sapiens*] | 4.03E−03 | 35250.3 |
| gi\|20070331\|ref\|NP_078862.2\|oxysterol-binding protein-like protein 9 isoform e [*Homo sapiens*] [MAS | 1.55E−03 | 83132.4 |
| gi\|20149635\|ref\|NP_057227.2\|p47 protein isoform a [*Homo sapiens*] [MASS = 40573] | 1.46E−05 | 40548.4 |
| gi\|20336754\|ref\|NP_066402.2\|H2B histone family, member R [*Homo sapiens*] [MASS= | 5.31E−04 | 13895.6 |
| gi\|21361144\|ref\|NP_002795.2\|proteasome 26S ATPase subunit 3 [*Homo sapiens*] [MA | 2.22E−03 | 49172.5 |
| gi\|21361670\|ref\|NP_054782.2\|drebrin-like isoform a [*Homo sapiens*] [MASS = 48294] | 3.67E−05 | 48264.7 |
| gi\|21361796\|ref\|NP_060926.2\|ELL associated factor 2 [*Homo sapiens*] [MASS = 2879 | 7.86E−03 | 28773.7 |
| gi\|21450727\|ref\|NP_659445.1\|yippee-like 4 [*Homo sapiens*] [MASS = 14301] | 8.73E−04 | 14291.9 |
| gi\|21536470\|ref\|NP_001908.2\|D-amino-acid oxidase [*Homo sapiens*] [MASS = 39496] | 6.11E−04 | 39471.2 |
| gi\|21729888\|ref\|NP_660189.1\|ATP-binding cassette, sub-family C, member 12 isoform b [*Homo sapiens*] | 5.49E−03 | 104584.7 |
| gi\|21735616\|ref\|NP_663318.1\|apolipoprotein L1 isoform b precursor [*Homo sapiens*] | 3.22E−03 | 45889.9 |
| gi\|22547229\|ref\|NP_057323.2\|myosin XV [*Homo sapiens*] [MASS = 395217] | 8.70E−03 | 394969.9 |
| gi\|22749217\|ref\|NP_689804.1\|hypothetical protein LOC160762 [*Homo sapiens*] [MA | 8.94E−04 | 66209.1 |
| gi\|23111062\|ref\|NP_004583.2\|splicing factor, arginine/serine-rich 8 isoform 1 [*Homo sapiens*] | 4.42E−05 | 104757.8 |
| gi\|24308191\|ref\|NP_065074.1\|p21-activated kinase 7 [*Homo sapiens*] [MASS = 80744 | 2.04E−05 | 80694.1 |
| gi\|24432100\|ref\|NP_722545.1\|germ cell associated 1 isoform 2 [*Homo sapiens*] [M | 6.25E−03 | 36727.0 |

TABLE 9-continued

List of proteins (fragments) identified in carrier protein-bound serum fraction from ovarian cancer samples

| NIH Protein Database Reference and Protein name | P (pro) | Protein MW |
|---|---|---|
| gi\|25777746\|ref\|NP_689808.2\|piggyBac transposable element derived 4 [Homo sapiens] | 2.59E−03 | 66961.2 |
| gi\|27465517\|ref\|NP_775109.1\|keratin 6 isoform K6e [Homo sapiens] [MASS = 60223] | 1.96E−07 | 60186.5 |
| gi\|27735143\|ref\|NP_775945.1\|discoidin, CUB and LCCL domain containing 1 [Homo sapiens] | 1.22E−03 | 59158.9 |
| gi\|27881486\|ref\|NP_775078.1\|zonadhesin isoform 1 [Homo sapiens] [MASS = 295259] | 2.28E−03 | 295067.0 |
| gi\|27894344\|ref\|NP_775180.1\|nuclear receptor subfamily 4, group A, member 1 isoform a [Homo sapien | 1.15E−03 | 64422.4 |
| gi\|28559039\|ref\|NP_004765.2\|peroxisome proliferator-activated receptor binding protein [Homo sapie | 9.99E−04 | 168372.6 |
| gi\|28872751\|ref\|NP_787954.1\|dual oxidase 1 precursor [Homo sapiens] [MASS = 1772 | 8.60E−05 | 177121.8 |
| gi\|29570791\|ref\|NP_808227.1\|casein kinase II alpha 1 subunit isoform a [Homo sapiens] | 3.02E−05 | 45114.9 |
| gi\|29826279\|ref\|NP_813977.1\|tubby isoform b [Homo sapiens] [MASS = 55651] | 4.39E−07 | 55617.0 |
| gi\|30425482\|ref\|NP_848627.1\|ring finger protein 180 [Homo sapiens] [MASS = 4728 | 3.06E−03 | 47255.8 |
| gi\|31317272\|ref\|NP_055806.2\|WD repeat and FYVE domain containing 3 isoform 1 [Homo sapiens] | 6.23E−04 | 395005.0 |
| gi\|31542984\|ref\|NP_002209.2\|inter-alpha (globulin) inhibitor H4 (plasma Kallikrein-sensitive glyco | 2.71E−13 | 103293.2 |
| gi\|31742492\|ref\|NP_060647.2\|Nedd4 binding protein 2 [Homo sapiens] [MASS = 1988 | 1.81E−03 | 198675.3 |
| gi\|33285008\|ref\|NP_689525.2\|glycosyltransferase-like 1B [Homo sapiens] [MASS= | 2.54E−04 | 81763.6 |
| gi\|33457308\|ref\|NP_872353.2\|transmembrane emp24 protein transport domain containing 4 [Homo sapien | 7.32E−03 | 25926.4 |
| gi\|34013530\|ref\|NP_898870.1\|thymosin-like 3 [Homo sapiens] [MASS = 5063] | 3.95E−04 | 5059.5 |
| gi\|34452713\|ref\|NP_899631.1\|Ca2+-dependent secretion activator isoform 2 [Homo sapiens] | 2.43E−03 | 148681.3 |
| gi\|37547051\|ref\|XP_046581.6\|PREDICTED: zinc finger, SWIM domain containing 5 [Homo sapiens] | 4.98E−03 | 142093.6 |
| gi\|37551889\|ref\|XP_292740.2\|PREDICTED: similar to Zinc finger protein 208 [Homo sapiens] | 1.26E−03 | 125349.5 |
| gi\|38348340\|ref\|NP_940914.1\|diacylglycerol O-acyltransferase 2 like 6 [Homo sapiens] | 2.51E−03 | 38568.5 |
| gi\|38348392\|ref\|NP_940955.1\|hypothetical protein LOC375190 [Homo sapiens] [MA | 9.25E−03 | 25926.0 |
| gi\|38490688\|ref\|NP_849144.2\|immunoglobulin superfamily, member 10 [Homo sapiens] | 6.26E−04 | 290653.4 |
| gi\|40354192\|ref\|NP_000412.2\|keratin 10 [Homo sapiens] [MASS = 58827] | 8.85E−07 | 58791.5 |
| gi\|40385883\|ref\|NP_954699.1\|ribulose-5-phosphate-3-epimerase isoform 1 [Homo sapiens] | 8.87E−03 | 24911.3 |
| gi\|41054864\|ref\|NP_055804.2\|regulating synaptic membrane exocytosis 1 isoform 1 [Homo sapiens] [MA | 7.95E−03 | 188955.1 |
| gi\|41282221\|ref\|NP_116222.2\|protein phosphatase 1, regulatory subunit 15B [Homo sapiens] | 7.25E−04 | 79076.2 |
| gi\|41393057\|ref\|NP_055742.2\|connector enhancer of kinase suppressor of Ras 2 [Homo sapiens] | 4.67E−03 | 117460.7 |
| gi\|42476118\|ref\|NP_001456.3\|FYN binding protein (FYB-120/130) isoform 1 [Homo sapiens] | 2.39E−03 | 90550.7 |
| gi\|42656705\|ref\|XP_379183.1\|PREDICTED: hypothetical protein XP_379183 [Homo sapiens] | 5.87E−03 | 11119.7 |
| gi\|42822884\|ref\|NP_919257.2\|hypothetical protein LOC125476 [Homo sapiens] [MAS | 5.42E−04 | 20629.7 |
| gi\|4502005\|ref\|NP_001613.1\|alpha-2-HS-glycoprotein [Homo sapiens] [MASS = 39324] | 5.09E−07 | 39299.7 |
| gi\|4502141\|ref\|NP_001157.1\|baculoviral IAP repeat-containing protein 2 [Homo sapiens] | 3.59E−04 | 69854.4 |
| gi\|4502359\|ref\|NP_001695.1\|brain-specific angiogenesis inhibitor 3 [Homo sapiens] | 8.21E−03 | 171379.1 |
| gi\|4502563\|ref\|NP_001739.1\|calpain 2, large subunit [Homo sapiens] [MASS = 8000 | 2.37E−03 | 79955.9 |
| gi\|4503401\|ref\|NP_001933.1\|desmoglein 1 preproprotein [Homo sapiens] [MASS = 113 | 1.26E−09 | 113644.0 |
| gi\|4503525\|ref\|NP_003743.1\|eukaryotic translation initiation factor 3, subunit 8, 110 kDa [Homo sap | 3.28E−03 | 105277.8 |
| gi\|4503581\|ref\|NP_001969.1\|erythrocyte membrane protein band 4.9 (dematin) [Homo sapiens] | 2.18E−03 | 45612.4 |

TABLE 9-continued

List of proteins (fragments) identified in carrier protein-bound serum fraction from ovarian cancer samples

| NIH Protein Database Reference and Protein name | P (pro) | Protein MW |
|---|---|---|
| gi|4503629|ref|NP_000496.1|coagulation factor XII precursor [Homo sapiens] [MA | 1.25E−04 | 67774.1 |
| gi|4503635|ref|NP_000497.1|coagulation factor II precursor [Homo sapiens] [MAS | 1.42E−03 | 69992.2 |
| gi|4504529|ref|NP_002150.1|histatin 1 [Homo sapiens] [MASS = 6963] | 1.49E−03 | 6958.4 |
| gi|4504893|ref|NP_000884.1|kininogen 1 [Homo sapiens] [MASS = 47883] | 2.45E−03 | 47852.7 |
| gi|4505933|ref|NP_002682.1|polymerase (DNA directed), delta 1, catalytic subunit 125 kDa [Homo sapi | 6.28E−05 | 123556.8 |
| gi|4505981|ref|NP_002695.1|pro-platelet basic protein precursor [Homo sapiens] | 1.51E−06 | 13885.4 |
| gi|4506117|ref|NP_000304.1|protein S (alpha) [Homo sapiens] [MASS = 75072] | 1.54E−06 | 75024.0 |
| gi|4506131|ref|NP_002757.1|phosphoribosyl pyrophosphate synthetase-associated protein 1 [Homo sapi | 4.84E−05 | 39454.8 |
| gi|4507357|ref|NP_003555.1|transgelin 2 [Homo sapiens] [MASS = 22391] | 9.44E−08 | 22377.2 |
| gi|4507467|ref|NP_000349.1|transforming growth factor, beta-induced, 68 kDa [Homo sapiens] | 1.95E−03 | 74634.1 |
| gi|4507725|ref|NP_000362.1|transthyretin [Homo sapiens] [MASS = 15887] | 2.68E−04 | 15877.1 |
| gi|4507869|ref|NP_003361.1|vasodilator-stimulated phosphoprotein isoform 1 [Homo sapiens] | 7.74E−13 | 39805.1 |
| gi|4507917|ref|NP_003381.1|wee1 tyrosine kinase [Homo sapiens] [MASS = 71597] | 3.72E−03 | 71552.8 |
| gi|4508047|ref|NP_003452.1|zyxin [Homo sapiens] [MASS = 61277] | 9.67E−10 | 61238.2 |
| gi|45238849|ref|NP_112241.2|poly(A) binding protein, cytoplasmic 3 [Homo sapiens] | 4.54E−03 | 69986.9 |
| gi|45331217|ref|NP_597701.1|zinc finger protein 526 [Homo sapiens] [MASS = 7362 | 6.61E−03 | 73574.4 |
| gi|4557323|ref|NP_000031.1|apolipoprotein C-III precursor [Homo sapiens] [MASS | 2.15E−05 | 10845.5 |
| gi|4557385|ref|NP_000055.1|complement component 3 precursor [Homo sapiens] [MA | 5.79E−11 | 187045.3 |
| gi|4557537|ref|NP_001379.1|developmentally regulated GTP binding protein 2 [Homo sapiens] | 9.22E−03 | 40720.4 |
| gi|4557667|ref|NP_000408.1|interleukin 2 receptor, alpha chain precursor [Homo sapiens] | 2.53E−03 | 30798.7 |
| gi|45827701|ref|NP_005119.2|pad-1-like [Homo sapiens] [MASS = 258228] | 3.13E−03 | 258065.2 |
| gi|45935371|ref|NP_002718.2|proteoglycan 1, secretory granule precursor [Homo sapiens] | 3.71E−06 | 17640.7 |
| gi|46409436|ref|NP_997289.1|hypothetical protein LOC389206 [Homo sapiens] [MAS | 8.23E−03 | 45059.1 |
| gi|46430499|ref|NP_068810.2|v-rel reticuloendotheliosis viral oncogene homolog A, nuclear factor o | 3.67E−04 | 60191.6 |
| gi|46447820|ref|NP_997397.1|differentially expressed in FDCP 8 isoform 1 [Homo sapiens] | 3.72E−04 | 58672.2 |
| gi|47132620|ref|NP_000414.2|keratin 2a [Homo sapiens] [MASS = 65432] | 8.02E−06 | 65393.2 |
| gi|47578105|ref|NP_597677.2|delangin isoform A [Homo sapiens] [MASS = 316049] | 4.68E−03 | 315851.9 |
| gi|4758056|ref|NP_004371.1| CREB binding protein [Homo sapiens] [MASS = 265335] | 1.08E−03 | 265166.0 |
| gi|4758464|ref|NP_004457.1| glypican 5 [Homo sapiens] [MASS = 63707] | 4.07E−05 | 63665.8 |
| gi|4759082|ref|NP_004648.1| serum deprivation response protein [Homo sapiens] [ | 1.58E−08 | 47144.6 |
| gi|4885373|ref|NP_005316.1| H1 histone family, member 1 [Homo sapiens] [MASS = 21 | 4.40E−04 | 21828.9 |
| gi|49472835|ref|NP_057377.2| bridging integrator 2 [Homo sapiens] [MASS = 61874] | 6.66E−11 | 61836.9 |
| gi|50080213|ref|NP_473445.1| olfactory receptor, family 6, subfamily C, member 3 [Homo sapiens] [MA | 3.85E−04 | 35507.5 |
| gi|50363221|ref|NP_001002235.1| serine (or cysteine) proteinase inhibitor, clade A (alpha-1 antipro | 7.36E−06 | 46707.1 |
| gi|51011133|ref|NP_996802.1| ADP-ribosylation factor-like 9 [Homo sapiens] [MA | 4.48E−03 | 13775.1 |
| gi|51100959|ref|NP_055668.1| RUN and TBC1 domain containing 1 [Homo sapiens] [ | 8.32E−03 | 118128.1 |
| gi|51339293|ref|NP_079421.4| hypothetical protein LOC80217 [Homo sapiens] [MAS | 8.53E−03 | 188630.2 |

TABLE 9-continued

List of proteins (fragments) identified in carrier protein-bound serum fraction from ovarian cancer samples

| NIH Protein Database Reference and Protein name | P (pro) | Protein MW |
|---|---|---|
| gi|51458239|ref|XP_372812.2| PREDICTED: similar to Glyceraldehyde 3-phosphate dehydrogenase, liver | 1.40E−03 | 45189.4 |
| gi|51458553|ref|XP_371254.3| PREDICTED: ubiquitin specific protease 24 [Homo sapiens] | 3.46E−03 | 285650.9 |
| gi|51458586|ref|XP_086186.4| PREDICTED: hypothetical protein FLJ13815 [Homo sapiens] | 7.31E−03 | 146092.6 |
| gi|51460473|ref|XP_497873.1| PREDICTED: similar to 60S ribosomal protein L19 [Homo sapiens] | 4.80E−03 | 49718.9 |
| gi|51464562|ref|XP_047995.8| PREDICTED: odz, odd Oz/ten-m homolog 2 [Homo sapiens] | 8.17E−03 | 339333.3 |
| gi|51464757|ref|XP_498018.1| PREDICTED: similar to Keratin, type I cytoskeletal 18 (Cytokeratin 18) | 2.44E−04 | 47013.1 |
| gi|51466183|ref|XP_499296.1| PREDICTED: hypothetical protein XP_499296 [Homo sapiens] | 2.07E−03 | 110659.5 |
| gi|51467136|ref|XP_498282.1| PREDICTED: similar to RPL7L1 protein [Homo sapiens] | 3.72E−03 | 59710.8 |
| gi|51467595|ref|XP_376902.2| PREDICTED: similar to RIKEN cDNA 4732481H14 [Homo sapiens] | 4.66E−03 | 69802.4 |
| gi|51473101|ref|XP_497523.1| PREDICTED: similar to nodulin [Homo sapiens] [MAS | 5.14E−03 | 115142.6 |
| gi|51474363|ref|XP_496200.1| PREDICTED: hypothetical protein XP_496200 [Homo sapiens] | 1.22E−03 | 38991.8 |
| gi|51474667|ref|XP_059037.4| PREDICTED: similar to WT1-interacting protein [Homo sapiens] | 1.47E−03 | 62418.8 |
| gi|51474965|ref|XP_373793.2| PREDICTED: hypothetical protein XP_373793 [Homo sapiens] | 8.61E−04 | 38400.7 |
| gi|51476101|ref|XP_037493.5| PREDICTED: proline-rich synapse-associated protein 2 [Homo sapiens] [M | 3.52E−03 | 198311.0 |
| gi|51476111|ref|XP_496536.1| PREDICTED: similar to Apolipoprotein A-I precursor (Apo-AI) [Homo sapi | 3.68E−08 | 30758.9 |
| gi|51492966|ref|XP_374751.2| PREDICTED: hypothetical protein XP_374751 [Homo sapiens] | 5.27E−05 | 17581.1 |
| gi|5174389|ref|NP_005882.1| acetyl-Coenzyme A acetyltransferase 2 [Homo sapiens] | 2.27E−04 | 41269.4 |
| gi|5174743|ref|NP_005994.1| ubiquinol-cytochrome c reductase, Rieske iron-sulfur polypeptide 1 [Hom | 3.92E−03 | 29633.4 |
| gi|52353296|ref|NP_001005203.1| olfactory receptor, family 8, subfamily S, member 1 [Homo sapiens] | 5.99E−03 | 39667.9 |
| gi|53832005|ref|NP_000712.2| calcium channel, voltage-dependent, alpha 1E subunit [Homo sapiens] [M | 1.79E−03 | 256949.6 |
| gi|5453800|ref|NP_006167.1| neurogranin [Homo sapiens] [MASS = 7618] | 2.25E−12 | 7613.7 |
| gi|55770876|ref|NP_004548.3| notch4 preproprotein [Homo sapiens] [MASS = 209621] | 3.99E−03 | 209478.2 |
| gi|55953100|ref|NP_064630.2| tubby like protein 4 isoform 1 [Homo sapiens] [MAS | 7.49E−03 | 168893.0 |
| gi|55956899|ref|NP_000217.2| keratin 9 [Homo sapiens] [MASS = 62064] | 1.32E−13 | 62026.7 |
| gi|56090535|ref|NP_001007526.1| hypothetical protein LOC284434 [Homo sapiens] [ | 6.56E−03 | 158941.8 |
| gi|56790299|ref|NP_002770.3| pleckstrin and Sec7 domain containing [Homo sapiens] | 1.67E−03 | 109475.5 |
| gi|5730033|ref|NP_006505.1| sodium channel, voltage-gated, type X, alpha [Homo sapiens] | 9.20E−04 | 220421.8 |
| gi|5730043|ref|NP_006589.1| solute carrier family 12 (potassium/chloride transporters), member 7 [H | 6.15E−03 | 119072.7 |
| gi|57864582|ref|NP_001009931.1| hornerin [Homo sapiens] [MASS = 282388] | 3.28E−04 | 282225.7 |
| gi|5803036|ref|NP_006796.1| heterogeneous nuclear ribonucleoprotein A0 [Homo sapiens] | 7.84E−03 | 30821.8 |
| gi|5803056|ref|NP_006753.1| Lysosomal associated multispanning membrane protein 5 [Homo sapiens] [M | 6.40E−03 | 29916.6 |
| gi|58533153|ref|NP_006448.2| PDZ and LIM domain 5 isoform a [Homo sapiens] [MAS | 2.63E−05 | 63961.6 |
| gi|60301553|ref|NP_006239.1| proline-rich protein BstNI subfamily 2 [Homo sapiens] | 3.10E−09 | 32576.6 |
| gi|61742777|ref|NP_005566.2| leucyl/cystinyl aminopeptidase isoform 1 [Homo sapiens] | 7.73E−04 | 117274.2 |
| gi|6631085|ref|NP_008965.2| DnaJ (Hsp40) homolog, subfamily B, member 4 [Homo sapiens] | 2.16E−05 | 37783.2 |
| gi|66932947|ref|NP_000005.2| alpha-2-macroglobulin precursor [Homo sapiens] [M | 2.78E−06 | 163188.3 |
| gi|67190748|ref|NP_009224.2| complement component 4A preproprotein [Homo sapiens] | 9.86E−12 | 192663.6 |

TABLE 9-continued

List of proteins (fragments) identified in carrier protein-bound serum fraction from ovarian cancer samples

| NIH Protein Database Reference and Protein name | P (pro) | Protein MW |
|---|---|---|
| gi\|67782356\|ref\|NP_001255.3\| corneodesmosin precursor [Homo sapiens] [MASS = 515 | 4.29E−03 | 51548.3 |
| gi\|6806898\|ref\|NP_009292.1\| alpha-synuclein isoform NACP112 [Homo sapiens] [MA | 3.83E−05 | 11365.0 |
| gi\|7019499\|ref\|NP_037393.1\| peroxisome proliferative activated receptor gamma coactivator 1 [Homo s | 3.41E−03 | 90970.8 |
| gi\|70906435\|ref\|NP_005132.2\| fibrinogen, beta chain preproprotein [Homo sapiens] | 8.15E−09 | 55892.2 |
| gi\|71061449\|ref\|NP_077302.2\| F-box and leucine-rich repeat protein 15 [Homo sapiens] | 1.68E−03 | 32958.4 |
| gi\|7662078\|ref\|NP_055454.1\| hypothetical protein LOC9652 [Homo sapiens] [MASS= | 1.48E−03 | 175374.0 |
| gi\|7662122\|ref\|NP_056374.1\| SET binding protein 1 [Homo sapiens] [MASS = 169631] | 2.46E−03 | 169526.8 |
| gi\|7705373\|ref\|NP_057441.1\| epithelial protein lost in neoplasm beta [Homo sapiens] | 4.57E−03 | 85173.3 |
| gi\|7706435\|ref\|NP_057301.1\| headcase [Homo sapiens] [MASS = 58836] | 2.40E−03 | 58798.7 |
| gi\|9507215\|ref\|NP_061816.1\| tubulin, alpha 8 [Homo sapiens] [MASS = 50093] | 1.24E−05 | 50061.6 |
| gi\|9943842\|ref\|NP_005379.2\| phosducin-like [Homo sapiens] [MASS = 34282] | 2.10E−04 | 34260.7 |
| gi\|9945310\|ref\|NP_006241.1\| proline-rich protein HaeIII subfamily 1 [Homo sapiens] | 2.20E−11 | 17005.3 |

REFERENCES

1. Bast R C. Status of Tumor Markers in Ovarian Cancer Screening. J Clin Oncol 2003; 21:200-205.
2. Boyce E A, Kohn E C. Ovarian cancer in the proteomics era: diagnosis, prognosis, and therapeutics targets. Int J Gynecol Cancer. 2005; 15 Suppl 3:266-273.
3. Bhoola S, Hoskins W J. Diagnosis and management of epithelial ovarian cancer. Obstet Gynecol. 2006; 107:1399-1410.
4. Moss E L, Hollingworth J, Reynolds T M. The role of CA125 in clinical practice. J Clin Pathol 2005; 58:308-312.
5. Hortin G L, Jortani S A, Ritchee, J C Jr, Valdes R Jr, Chan D W. Proteomics: A new diagnostic frontier. Clin Chem 2006; 52:1218-1222.
6. Wulfkuhle J D, Liotta L A, Petricoin E F. Proteomic applications for the early detection of cancer. Nat Rev Cancer 2003; 3:267-275.
7. Ardekani A M, Liotta L A, Petricoin E F 3rd. Clinical potential of proteomics in the diagnosis of ovarian cancer. Expert Rev Mol Diagn 2002; 2:312-320.
8. Srinivas P R, S. Srivastava S, Hanash S, Wright G L, Proteomics in early detection of cancer. Clin Chem 2001; 47:1901-1911.
9. Rosenblatt K P, Bryant-Greenwood P, Killian J K, Mehta A, Geho D, Espina V, Petricoin E F, Liotta L A. Serum proteomics in cancer diagnosis and management. Annu Rev Med 2004; 55:97-112.
10. Zhang Z, Bast R C Jr, Yu Y, Li J, Sokoll L J, Rai A J, Rosenzweig J M, Cameron B, Wang Y Y, Meng X Y, Berchuck A, Van Haaften-Day C, Hacker N F, de Bruijn H W, van der Zee A G, Jacobs I J, Fung E T, Chan D W. Three biomarkers identified from serum proteomic analysis for the detection of early stage ovarian cancer. Cancer Res 2004; 64:5882-5890.
11. Li J, Zhang Z, Rosenzweig J, Wang Y Y, Chan D W. Proteomics and bioinformatics approaches for identification of serum biomarkers to detect breast cancer. Clin Chem 2002; 48:1296-1304.
12. Petricoin E F, Ardekani A M, Hitt B A, Levine P J, Fusaro V A, Steinberg S M, Mills G B, Simone C, Fishman D A, Kohn E C, Liotta L A. Use of proteomic patterns in serum to identify ovarian cancer. Lancet 2002; 359:572-577.
13. Adam B L, et al. Serum protein fingerprinting coupled with a pattern-matching algorithm distinguishes prostate cancer from benign prostate hyperplasia and healthy men. Cancer Res 2002; 62:3609-3614.
14. Petricoin E F 3rd, et al. Serum proteomic patterns for detection of prostate cancer. J Natl Cancer Inst 2002; 94:1576-1578.
15. Hortin G L. The MALDI-TOF mass spectrometric view of the plasma proteome and peptidome. Clin Chem 2006; 52:1223-1237.
16. Whiteley G R Proteomic patterns for cancer diagnosis-promise and challenges. Mol BioSyst 2006; 2:358-363.
17. Xu R, Gamst A. Re: Lessons from controversy: Ovarian cancer screening and serum proteomics. J Natl Cancer Inst. 2005; 97:1226.
18. Baggerly K A, Morris J S, Edmonson S R, Coombes K R. Signal in noise: evaluating reported reproducibility of serum proteomic tests for ovarian cancer. J Natl Cancer Inst. 2005 Feb. 16; 97(4):307-309.
19. Liotta L A, Lowenthal M, Mehta A, Conrads T P, Veenstra T D, Fishman D A, Petricoin E F 3rd. Importance of communication between producers and consumers of publicly available experimental data. J Natl Cancer Inst. 2005 Feb. 16; 97(4):310-314.
20. Diamandis E P. Point: proteomic patterns in biological fluids: do they represent the future of cancer diagnostics? Clin Chem 2003; 49:1272-1275.
21. Sorace J M, and Zhan M. A data review and re-assessment of ovarian cancer serum proteomic profiling. BMC Bioinformatics 2003; 4:24.
22. Liotta L A, Petricoin E F. Serum peptidome for cancer detection: spinning biologic trash into diagnostic gold. J Clin Invest 2006; 116:26-30.

23. Lowenthal M S, Mehta A I, Frogale K, Bandle R W, Araujo R P, Hood B L, Veenstra T D, Conrads T P, Goldsmith P, Fishman D, Petricoin E F III, Liotta L A. Analysis of Albumin-Associated Peptides and Proteins from Ovarian Cancer Patients. Clin Chem 2005; 51:1933-1945.
24. Diamandis E P. Peptidomics for cancer diagnosis: present and future. J Proteome Res. 2006; 9:2079-2082.
25. Tirumalai R S, Chan K C, Prieto D A, Issaq H J, Conrads T P, Veenstra T D. Characterization of the low molecular weight human serum proteome. Mol Cell Proteomics 2003; 2:1096-2003.
26. Liu H, Sadygov R G, Yates J R. A model for random sampling and estimation of relative protein abundance in shotgun proteomics. Anal Chem 2004; 76:4193-4201.
27. Pieper R, Gatlin C L, Makusky A J, Russo P S, Schatz C R, Miller S S, et al. The human serum proteome: display of nearly 3700 chromatographically separated protein spots on two-dimensional electrophoresis gels and identification of 325 distinct proteins. Proteomics 2003; 3:1345-1364.
28. Adkins J N, Varnum S M, Auberry K J, Moore R J, Angell N H, Smith R D, et al. Toward a human blood serum proteome: analysis by multidimensional separation coupled with mass spectrometry. Mol Cell Proteomics 2002; 1:947-955.
29. Washburn M P, Wolters D, Yates J R 3rd. Large-scale analysis of the yeast proteome by multidimensional protein identification technology. Nat Biotechnol 2001; 19:242-247.
30. Rothemund D L, Locke V L, Liew A, Thomas T M, Wasinger V, Rylatt, D B. Depletion of the highly abundant protein albumin from human plasma using the Gradiflow. Proteomics 2003; 3:279-287.
31. Wang Y Y, Cheng P, Chan D W. A simple affinity spin tube filter method for removing high-abundant common proteins or enriching low-abundant biomarkers for serum proteomic analysis. Proteomics 2003; 3:243-248.
32. Mehta A I, Ross S, Lowenthal M S, Fusaro V, Fishman D A, Petricoin E F 3rd, Liotta L A. Biomarker amplification by serum carrier protein binding. Dis Markers 2003; 19:1-10.
33. Lopez M F, et. al. High-resolution serum proteomic profiling of Alzheimer's disease samples reveals disease-specific, carrier-protein-bound mass signatures. Clin Chem 2005; 1946-1954.
34. Zhou M, Lucas D A, Chan K C, Issaq H J, Petricoin E F 3rd, Liotta L A, et al. An investigation into the human serum "interactome". Electrophoresis 2004; 25:1289-1298.
35. Sing, T. & Sander, O. & Beerenwinkel, N. & Lengauer, T. ROCR: An R Package for visualizing the performance of scoring classifiers. 2004 http://rocr.bioinf.mpi-sb.mpg.de.
36. Hastie, T. J., Tibshirani, R. and Buja, A. Flexible Discriminant Analysis by Optimal Scoring. JASA 1994; 89:155-1270.
37. Molinaro A M, Simon R, Pfeiffer R M. Prediction Error Estimation: A Comparison of Resampling Methods. Bioinformatics 2005; 21:3294-3300.
38. Scaglioni P P, Yung T M, Cai L F, Erdjument-Bromage H, Kaufman A J, Singh B, Teruya-Feldstein J, Tempst P, Pandolfi P P. A CK2-Dependent Mechanism for Degradation of the PML Tumor Suppressor. Cell. 2006; 126:269-83.
39. DeSouza L, Diehl G, Rodrigues M J, Guo J, Romaschin A D, Colgan T J, Siu K W. Search for cancer markers from endometrial tissues using differentially labeled tags iTRAQ and cICAT with multidimensional liquid chromatography and tandem mass spectrometry. J Proteome Res. 2005; 4:377-386.
40. Chen H, Wang M, Wang X Y, Gao S, Wang J, Guan X M. Identification of differential genes in ovarian cancer using representational difference analysis of cDNA. Chin Med Sci J. 2005; 3:185-189.
41. Sieja K, Stanosz S, von Mach-Szczypinski J, Olewniczak S, Stanosz M. Concentration of histamine in serum and tissues of the primary ductal breast cancers in women. Breast. 2005; 14:236-241.
42. Bloor B K, Tidman N, Leigh I M, Odell E, Dogan B, Wollina U, Ghali L, Waseem A. Expression of keratin K2e in cutaneous and oral lesions: association with keratinocyte activation, proliferation, and keratinization. Am J Pathol. 2003; 162:963-975.
43. Juang C M, Yang Y H, Lo W H, Lai C R, Hsieh S L, Yuan C C. Altered mRNA expressions of sialyltransferases in ovarian cancers. Wang P H, Lee W L, Gynecol Oncol. 2005 December; 99:631-639.
44. Anderson N L, Polanski M, Pieper R, Gatlin T, Tirumalai R S, Contrads T P, Veenstra T D, Adkins J N, pounds J G, Fagan R, Lobley A. The human plasma proteome. Molec Cell Proteom 2004; 3.4:311-326.
45. Rickles F R. Mechanisms of cancer-induced thrombosis in cancer. Pathophysiol Haemost Thromb. 2006; 35:103-110.
46. Bast R C Jr, Badgwell D, Lu Z, Marquez R, Rosen D, Liu J, Baggerly K A, Atkinson E N, Skates S, Zhang Z, Lokshin A, Menon U, Jacobs I, Lu K. New tumor markers: CA125 and beyond. Int J Gynecol Cancer. 2005; 15 Suppl 3:274-281.
47. Kumar R, Hung M-C. Signaling Intricacies Take Center Stage in Cancer Cells. Cancer Res 2005; 65:2511-2515.
48. Shiratsuchi T, Nishimori H, Ichise H, Nakamura Y, Tokino T. Cloning and characterization of BAI2 and BAI3, novel genes homologous to brain-specific angiogenesis inhibitor 1 (BAI1). Cytogenet Cell Genet 1997; 79:103-108.
49. Veugelers M, De Cat B, Delande N, Esselens C, Bonk I, Vermeesch J, Marynen P, Fryns J P, David G. A 4-Mb BAC/PAC contig and complete genomic structure of the GPC5/GPC6 gene cluster on chromosome 13q32. Matrix Biol 2001; 20:375-385.
50. Yu W, Inoue J, Imoto I, Matsuo Y, Karpas A, Inazawa J. GPC5 is a possible target for the 13q31-q32 amplification detected in lymphoma cell lines. J Hum Genet 2003; 48:331-335.
51. Thompson H G, Harris J W, Brody J P. Post-translationally modified S12, absent in transformed breast epithelial cells, is not associated with the 26S proteasome and is induced by proteasome inhibitor. Int J Cancer. 2004; 111: 338-347.
52. Pollice A, Nasti V, Ronca R, Vivo M, Lo Iacono M, Calogero R, Calabro V, La Mantia G. Functional and physical interaction of the human ARF tumor suppressor with Tat-binding protein-1. J Biol Chem. 2004; 279:6345-6353.
53. Ijichi H, Tanaka T, Nakamura T, Yagi H, Hakuba A, Sato M. Molecular cloning and characterization of a human homologue of TBPIP, a BRCA1 locus-related gene. Gene. 2000; 248:99-107.
54. Haddad P, Jenne D, Tschopp J, Clement M V, Mathieu-Mahul D, Sasportes M. Structure and evolutionary origin of the human granzyme H gene. Int Immunol 1991; 1:57-66.
55. Sedelies K A, Sayers T J, Edwards K M, Chen W, Pellicci D G, Godfrey D I, Trapani J A. Discordant regulation of granzyme H and granzyme B expression in human lymphocytes. J Biol Chem. 2004; 279:26581-26587.

56. Crowe D L, Lee M K. New role for nuclear hormone receptors and coactivators in regulation of BRCA1-mediated DNA repair in breast cancer cell lines. Breast Cancer Res. 2006; 8:R1.
57. Miele L, Miao H, Nickoloff B J. NOTCH Signaling as a Novel Cancer Therapeutic Target. Curr Cancer Drug Targets. 2006; 6:313-323.
58. Makino N, Yamato T, Inoue H, Furukawa T, Abe T, Yokoyama T, Yatsuoka T, Fukushige S, Orikasa S, Takahashi T, Horii A. Isolation and characterization of the human gene homologous to the *Drosophila* headcase (hdc) gene in chromosome bands 6q23-q24, a region of common deletion in human pancreatic cancer. DNA Seq 2001; 11:547-553.
59. Minakuchi M, Kakazu N, Gorrin-Rivas M J, Abe T, Copeland T D, Ueda K, Adachi Y. Identification and characterization of SEB, a novel protein that binds to the acute undifferentiated leukemia-associated protein SET. Eur J Biochem 2001; 268:1340-1351.
60. Kozak K R, Su F, Whitelegge J P, Faull K, Reddy S, Farias-Eisner R. Characterization of serum biomarkers for detection of early stage ovarian cancer. Proteomics. 2005; 17:4589-4596.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method for detecting likelihood of ovarian cancer in a female subject, the method comprising:
   detecting one or both of the presence and amount of one or more biomarkers in a biological sample from the subject,
   wherein at least one of the biomarkers is a peptide selected from SEQ ID NOs: 1-6, 8-13, 15, 20, and 22; and
   classifying the subject as likely to have ovarian cancer if
   (a) the amount of the peptide selected from SEQ ID NOs: 1, 2, 4, 8, 9, 10, 11, and 12 is decreased in the biological sample as compared to a non-ovarian cancer reference amount of the biomarker; or
   (b) the amount of the peptide selected from SEQ ID NOs: 3, 5, 6, 13, 15, 20, and 22 is increased in biological sample as compared to a non-ovarian cancer reference amount of the biomarker.

2. The method of claim 1, wherein an increase in the amount of a biomarker peptide selected from SEQ ID NOs: 3, 5, 6, 13, 15, 20, and 22 in the biological sample as compared to the non-ovarian cancer reference amount of the biomarker peptide indicates that the subject has an ovarian cancer.

3. The method of claim 2, wherein the amount of the biomarker peptide in the biological sample is at least two-fold higher than the non-ovarian cancer reference amount of the biomarker peptide.

4. The method of claim 1, wherein a decrease in the amount of a biomarker peptide selected from SEQ ID NOs: 1, 2, 4, 8, 9, 10, 11, and 12 in the biological sample as compared to the non-ovarian cancer reference amount of the biomarker peptide indicates that the subject has an ovarian cancer.

5. The method of claim 4, wherein the amount of the biomarker peptide in the biological sample is at least two-fold lower than the non-ovarian cancer reference amount of the biomarker peptide.

6. The method of claim 1, comprising classifying the subject as likely to have an ovarian cancer of a type selected from the group consisting of a serous cystoma, a mucinous cystoma, an endometroid tumor, and a clear cell tumor.

7. The method of claim 1, comprising classifying the subject as likely to have an ovarian cancer at a stage selected from the group consisting of Stage I, Stage IA, Stage IB, Stage IC, Stage II, Stage IIA, Stage IIB, Stage IIC, Stage III, Stage IIIA, Stage IIIB, Stage IIIC, and Stage IV.

8. The method of claim 1, further comprising obtaining the biological sample from the subject.

9. The method of claim 1, wherein the subject is a human.

10. The method claim 1, wherein the non-ovarian cancer reference amount of the biomarker peptide is an amount of the biomarker peptide in a biological sample from a subject that does not have an ovarian cancer.

11. The method of claim 1, wherein the biological sample comprises serum.

12. The method of claim 1, wherein the detecting comprises mass spectrometry.

13. The method of claim 1, wherein the one or more biomarkers comprise at least four of the biomarker peptides.

14. The method of claim 1, wherein the one or more biomarkers comprise at least five of the biomarker peptides.

15. The method of claim 14, wherein the at least five biomarker peptides are selected from the group consisting of SEQ ID NOS: 2, 3, 4, 5, and 6.

16. The method of claim 1, wherein the one or more biomarkers comprise at least seven of the biomarker peptides.

17. The method of claim 16, wherein the at least seven biomarker peptides are selected from the group consisting of SEQ ID NOS: 8, 15, 2, 3, 4, 5, and 6.

18. The method of claim 1, wherein the one or more biomarkers comprise at least nine of the biomarker peptides.

19. The method of claim 18, wherein the at least nine biomarker peptides are selected from the group consisting of SEQ ID NOS: 9, 8, 12, 10, 11, 15, 22, 13, and 20.

20. The method of claim 1, further comprising detecting one or both of the presence and amount of CA125 in the biological sample.

21. The method of claim 1, further comprising creating a record indicating one or both of the presence and amount of the one or more biomarkers in the biological sample.

22. The method of claim 1, further comprising creating a record indicating that the subject should undergo one or more additional diagnostic tests to detect an ovarian cancer if the subject is classified as likely to have an ovarian cancer.

23. The method of claim 22, wherein the one or more additional tests comprise a biopsy.

24. The method of claim 1, further comprising creating a record indicating that the subject is likely to have ovarian cancer if the subject is classified as likely to have an ovarian cancer.

25. The method of claim 21, wherein the record is on a computer readable medium.

26. The method of claim 1, further comprising prescribing for the subject a therapy comprising an anti-cancer agent if the amount of the biomarker peptide is different than the non-ovarian cancer reference amount of the biomarker peptide.

27. A method for detecting a likelihood of ovarian cancer in a female subject, the method comprising:
   measuring the amount of at least four biomarkers in a biological sample from the subject using mass spectrometry,
   wherein the biomarkers are peptides selected from the group consisting of peptides having a mass-to-charge ratio (m/z) signal at m/z 1739.93, 2582.35, 2659.27, and 2989.49, and wherein one or both of a decrease in the amount of the signal at m/z 1739.93 and an increase in the amount of signal at m/z 2582.35, 2659.27, and 2989.49 in the biological sample as compared to a non-ovarian cancer reference amount of the signals indicates that the subject is likely to have ovarian cancer.

28. A method for detecting a likelihood of ovarian cancer in a female subject, the method comprising:
   measuring the amount of at least five biomarkers in a biological sample from the subject,
   wherein the biomarkers comprise SEQ ID NOS: 2, 3, 4, 5, and 6, and wherein one or both of a decrease in the amount of SEQ ID NO: 2 and 4, and an increase in the amount of SEQ ID NOS: 3, 5, and 6, in the biological sample as compared to a non-ovarian cancer reference amount of the biomarkers indicates that the subject is likely to have ovarian cancer.

29. A method for detecting a likelihood of ovarian cancer in a female subject, the method comprising:
   measuring the amount of at least seven biomarkers in a biological sample from the subject,
   wherein the biomarkers comprise an amino acid sequence comprising SEQ ID NOS: 8, 15, 2, 3, 4, 5, and 6, and wherein one or both of a decrease in the amount of SEQ ID NOS: 8, 2, and 4, and an increase in the amount of SEQ ID NOS: 15, 3, 5, and 6, in the biological sample as compared to a non-ovarian cancer reference amount of the biomarkers indicates that the subject is likely to have ovarian cancer.

30. A method for detecting a likelihood of ovarian cancer in a female subject, the method comprising:

measuring the amount of at least nine biomarkers in a biological sample from the subject, wherein the biomarkers comprise SEQ ID NOS: 9, 8, 12, 10, 11, 15, 22, 13, and 20, and wherein one or both of a decrease in the amount of SEQ ID NOS: 9, 8, 12, 10, and 11, and an increase in the amount of SEQ ID NOS: 15, 22, 13, and 20, in the biological sample as compared to a non-ovarian cancer reference amount of the biomarkers indicates that the subject is likely to have ovarian cancer.

31. A method for treating an ovarian cancer in a female subject, the method comprising:

determining the amount of a peptide selected from SEQ ID NOs: 1-6, 8-13, 15, 20, and 22 in a biological sample from the subject; and administering to the subject a therapy comprising an effective amount of an anti-cancer agent if in the biological sample it has been determined that:

(a) the amount of a peptide selected from SEQ ID NOs: 1, 2, 4, and 8-12 is decreased in the biological sample as compared to a non-ovarian cancer reference amount of the biomarker; or (b) the amount of a peptide selected from SEQ ID NOs: 3, 5, 6, 13, 15, 20, and 22 is increased in biological sample as compared to a non-ovarian cancer reference amount of the biomarker.

32. A method for selecting a therapy for a female subject, the method comprising:

determining the amount of a biomarker peptide in a biological sample from the subject, wherein the biomarker peptide is selected from SEQ ID NOs: 1-6, 8-13, 15, 20, and 22; and selecting for the subject a therapy comprising an anti-cancer agent if in the biological sample from the subject (a) the amount of a peptide selected from SEQ ID NOs: 1, 2, 4, and 8-12 is decreased in the biological sample as compared to a non-ovarian cancer reference amount of the biomarker; or (b) the amount of a peptide selected from SEQ ID NOs: 3, 5, 6, 13, 15, 20, and 22 is increased in biological sample as compared to a non-ovarian cancer reference amount of the biomarker.

33. The method of claim 1, wherein at least one of the biomarkers is the peptide SEQ ID NO: 1.

34. The method of claim 31, wherein the biomarker peptide is SEQ ID NO:1.

35. The method of claim 32, wherein the biomarker peptide is SEQ ID NO:1.

36. The method of claim 31, wherein the biological sample comprises serum.

37. The method of claim 32, wherein the biological sample comprises serum.

38. The method of claim 1, wherein an increase in the amount of a biomarker peptide selected from SEQ ID NOs: 3, 5, 6, 15, 20, and 22 in the biological sample as compared to the non-ovarian cancer reference amount of the biomarker peptide indicates that the subject has an ovarian cancer.

39. The method of claim 38, wherein the amount of the biomarker peptide in the biological sample is at least two-fold higher than the non-ovarian cancer reference amount of the biomarker peptide.

40. The method of claim 1, wherein a decrease in the amount of a biomarker peptide selected from SEQ ID NOs: 1, 2, 4, 8, 9, 10, and 12 in the biological sample as compared to the non-ovarian cancer reference amount of the biomarker peptide indicates that the subject has an ovarian cancer.

41. The method of claim 40, wherein the amount of the biomarker peptide in the biological sample is at least two-fold lower than the non-ovarian cancer reference amount of the biomarker peptide.

42. The method of claim 1, wherein at least one of the biomarkers consists of a peptide selected from SEQ ID NOs: 1-6, 8-13, 15, 20, and 22.

43. The method of claim 32, wherein the biomarker peptide consists of a sequence selected from SEQ ID NOs: 1-6, 8-13, 15, 20, and 22.

44. The method of claim 12, wherein the biomarkers comprise peptides having a mass-to-charge ratio (m/z) signal at m/z 1865.02, 1966.91, 1041.68, 2115.05, 1224.68, 2345.19, 1739.93, 1690.94, 1865.01, 2021.11, 1777.97, 3027.57, 2582.35, 3239.55, and 2898.54, and wherein one or both of a decrease in the amount of the signal at m/z 1865.02, 1966.91, 2115.05, 1739.93, 1690.94, 1865.01, 2021.11, and 1777.97, and an increase in the amount of signal at m/z 1041.68, 1224.68, 2345.19, 3027.57, 2582.35, 3239.55, and 2898.54 in the biological sample as compared to a non-ovarian cancer reference amount of the signals indicates that the subject is likely to have ovarian cancer.

45. The method of claim 27, wherein the biological sample comprises serum.

46. The method of claim 27, further comprising detecting one or both of the presence and amount of CA125 in the biological sample.

47. The method of claim 28, wherein the measuring comprises mass spectrometry.

48. The method of claim 47, wherein the biomarkers comprise peptides having a mass-to-charge ratio (m/z) signal at m/z 1966.91, 1041.68, 2115.05, 1224.68, and 2345.19, and wherein one or both of a decrease in the amount of the signal at m/z 1966.91 and 2115.05 and an increase in the amount of signal at m/z 1041.68, 1224.68, and 2345.19 in the biological sample as compared to a non-ovarian cancer reference amount of the signals indicates that the subject is likely to have ovarian cancer.

49. The method of claim 29, wherein the measuring comprises mass spectrometry.

50. The method of claim 49, wherein the biomarkers comprise peptides having a mass-to-charge ratio (m/z) signal at m/z 1739.93, 2582.35, 1966.91, 1041.68, 2115.05, 1224.68, and 2345.19, and wherein one or both of a decrease in the amount of the signal at m/z 1739.93, 1966.91 and 2115.05 and an increase in the amount of signal at m/z 2582.35, 1041.68, 1224.68, and 2345.19 in the biological sample as compared to a non-ovarian cancer reference amount of the signals indicates that the subject is likely to have ovarian cancer.

51. The method of claim 30, wherein the measuring comprises mass spectrometry.

52. The method of claim 51, wherein the biomarkers comprise peptides having a mass-to-charge ratio (m/z) signal at m/z 1690.94, 1739.93, 1777.97, 1865.01, 2021.11, 2582.35, 2898.54, 3027.57, and 3239.55, and wherein one or both of a decrease in the amount of the signal at m/z 1690.94, 1739.93, 1777.97, 1865.01, and 2021.11, and an increase in the amount of signal at m/z 2582.35, 2898.54, 3027.57, and 3239.55 in the biological sample as compared to a non-ovarian cancer reference amount of the signals indicates that the subject is likely to have ovarian cancer.

53. The method of claim 31, wherein the determining comprises mass spectrometry.

54. The method of claim 53, wherein the biomarkers comprise peptides having a mass-to-charge ratio (m/z) signal at m/z 1865.02, 1966.91, 1041.68, 2115.05, 1224.68, 2345.19, 1739.93, 1690.94, 1865.01, 2021.11, 1777.97, 3027.57, 2582.35, 3239.55, and 2898.54, and administering to the subject a therapy comprising an effective amount of an anti-cancer agent if the amount of the signal at m/z 1865.02, 1966.91, 2115.05, 1739.93, 1690.94, 1865.01, 2021.11, and 1777.97 is decreased or the amount of signal at m/z 1041.68, 1224.68, 2345.19, 3027.57, 2582.35, 3239.55, and 2898.54 is increased in the biological sample as compared to a non-ovarian cancer reference amount of the signals.

55. The method of claim 32, wherein the determining comprises mass spectrometry.

56. The method of claim 55, wherein the biomarkers comprise peptides having a mass-to-charge ratio (m/z) signal at m/z 1865.02, 1966.91, 1041.68, 2115.05, 1224.68, 2345.19, 1739.93, 1690.94, 1865.01, 2021.11, 1777.97, 3027.57, 2582.35, 3239.55, and 2898.54, and selecting for the subject a therapy comprising an anti-cancer agent if the amount of the signal at m/z 1865.02, 1966.91, 2115.05, 1739.93, 1690.94, 1865.01, 2021.11, and 1777.97 is decreased or the amount of signal at m/z 1041.68, 1224.68, 2345.19, 3027.57, 2582.35, 3239.55, and 2898.54 is increased in the biological sample as compared to a non-ovarian cancer reference amount of the signals.

* * * * *

UNITED STATES PATENT AND TRADEMARK OFFICE
CERTIFICATE OF CORRECTION

PATENT NO. : 8,288,110 B2
APPLICATION NO. : 11/950416
DATED : October 16, 2012
INVENTOR(S) : Mary F. Lopez and Scott Kuzdzal It is certified that error appears in the above-identified patent and that said Letters Patent is hereby corrected as shown below:

Claim 6, column 73, line 39:
delete "endometroid" and replace with -- endometrioid --.

Claim 28, column 74, line 51:
delete "NO" and replace with -- NOS --.

Signed and Sealed this
Fifteenth Day of January, 2013

David J. Kappos
*Director of the United States Patent and Trademark Office*

SEQUENCE LISTING

```
<160> NUMBER OF SEQ ID NOS: 45

<210> SEQ ID NO 1
<211> LENGTH: 17
<212> TYPE: PRT
<213> ORGANISM: Homo sapiens

<400> SEQUENCE: 1

Ser Ser Lys Ile Thr His Arg Ile His Trp Glu Ser Ala Ser Leu Leu
1               5                   10                  15

Arg

<210> SEQ ID NO 2
<211> LENGTH: 17
<212> TYPE: PRT
<213> ORGANISM: Homo sapiens

<400> SEQUENCE: 2

Thr Asp Val Asn Thr His Arg Pro Arg Glu Tyr Trp Asp Tyr Glu Ser
1               5                   10                  15

His

<210> SEQ ID NO 3
<211> LENGTH: 11
<212> TYPE: PRT
<213> ORGANISM: Homo sapiens

<400> SEQUENCE: 3

Leu Asn Val Lys Val Asp Pro Glu Ile Gln Asn
1               5                   10

<210> SEQ ID NO 4
<211> LENGTH: 22
<212> TYPE: PRT
<213> ORGANISM: Homo sapiens

<400> SEQUENCE: 4

Ala Arg Glu Gly Ala Asp Val Ile Val Asn Cys Thr Gly Val Trp Ala
1               5                   10                  15

Gly Ala Leu Gln Arg Asp
            20

<210> SEQ ID NO 5
<211> LENGTH: 12
<212> TYPE: PRT
```

<213> ORGANISM: Homo sapiens

<400> SEQUENCE: 5

Leu Lys Pro Arg Val Ser Trp Ile Pro Asn Lys His
1               5                   10

<210> SEQ ID NO 6
<211> LENGTH: 23
<212> TYPE: PRT
<213> ORGANISM: Homo sapiens
<220> FEATURE:
<221> NAME/KEY: VARIANT
<222> LOCATION: 2, 13, 18
<223> OTHER INFORMATION: oxidized methionine

<400> SEQUENCE: 6

Gln Met Gly Thr Asn Arg Gly Ala Ser Gln Ala Gly Met Thr Gly Tyr
1               5                   10                  15

Gly Met Pro Arg Gln Ile Leu
            20

<210> SEQ ID NO 7
<211> LENGTH: 16
<212> TYPE: PRT
<213> ORGANISM: Homo sapiens

<400> SEQUENCE: 7

Arg Asn Gly Phe Lys Ser His Ala Leu Gln Leu Asn Asn Arg Gln Ile
1               5                   10                  15

<210> SEQ ID NO 8
<211> LENGTH: 17
<212> TYPE: PRT
<213> ORGANISM: Homo sapiens

<400> SEQUENCE: 8

Arg Asn Gly Phe Lys Ser His Ala Leu Gln Leu Asn Asn Arg Gln Ile
1               5                   10                  15

Arg

<210> SEQ ID NO 9
<211> LENGTH: 16
<212> TYPE: PRT
<213> ORGANISM: Homo sapiens

<400> SEQUENCE: 9

Ser Lys Ile Thr His Arg Ile His Trp Glu Ser Ala Ser Leu Leu Arg
1               5                   10                  15

<210> SEQ ID NO 10
<211> LENGTH: 18
<212> TYPE: PRT
<213> ORGANISM: Homo sapiens

<400> SEQUENCE: 10

Arg Ser Ser Lys Ile Thr His Arg Ile His Trp Glu Ser Ala Ser Leu
1               5                   10                  15

Leu Arg

<210> SEQ ID NO 11
<211> LENGTH: 19
<212> TYPE: PRT
<213> ORGANISM: Homo sapiens

<400> SEQUENCE: 11

Arg Ser Ser Lys Ile Thr His Arg Ile His Trp Glu Ser Ala Ser Leu
1               5                   10                  15

Leu Arg Ser

<210> SEQ ID NO 12
<211> LENGTH: 17
<212> TYPE: PRT
<213> ORGANISM: Homo sapiens

<400> SEQUENCE: 12

Ser Ser Lys Ile Thr His Arg Ile His Trp Glu Ser Ala Ser Leu Leu
1               5                   10                  15

Arg

<210> SEQ ID NO 13
<211> LENGTH: 30
<212> TYPE: PRT
<213> ORGANISM: Homo sapiens

<400> SEQUENCE: 13

Asn Phe Arg Pro Gly Val Leu Ser Arg Gln Leu Gly Leu Pro Gly
1               5                   10                  15

Pro Pro Asp Val Pro Asp His Ala Ala Tyr His Pro Phe Arg
            20                  25                  30

<210> SEQ ID NO 14
<211> LENGTH: 13
<212> TYPE: PRT
<213> ORGANISM: Homo sapiens

<400> SEQUENCE: 14

Pro Pro Asp Val Pro Asp His Ala Ala Tyr His Pro Phe
1               5                   10

<210> SEQ ID NO 15
<211> LENGTH: 25
<212> TYPE: PRT
<213> ORGANISM: Homo sapiens

<400> SEQUENCE: 15

Arg Asn Val His Ser Gly Ser Thr Phe Phe Lys Tyr Tyr Leu Gln Gly
1               5                   10                  15

Ala Lys Ile Pro Lys Pro Glu Ala Ser
            20                  25

<210> SEQ ID NO 16
<211> LENGTH: 32
<212> TYPE: PRT
<213> ORGANISM: Homo sapiens

<400> SEQUENCE: 16

Arg Met Asn Phe Arg Pro Gly Val Leu Ser Arg Gln Leu Gly Leu
1               5                   10                  15

Pro Gly Pro Pro Asp Val Pro Asp His Ala Ala Tyr His Pro Phe Arg
            20                  25                  30

<210> SEQ ID NO 17
<211> LENGTH: 26
<212> TYPE: PRT
<213> ORGANISM: Homo sapiens

<400> SEQUENCE: 17

```
Arg Asn Val His Ser Gly Ser Thr Phe Phe Lys Tyr Tyr Leu Gln Gly
1               5                   10                  15

Ala Lys Ile Pro Lys Pro Glu Ala Ser Phe
            20                  25
```

<210> SEQ ID NO 18
<211> LENGTH: 29
<212> TYPE: PRT
<213> ORGANISM: Homo sapiens

<400> SEQUENCE: 18

```
Arg Gly His Arg Pro Leu Asp Lys Lys Arg Glu Glu Ala Pro Ser Leu
1               5                   10                  15

Arg Pro Ala Pro Pro Ile Ser Gly Gly Gly Tyr Arg
            20                  25
```

<210> SEQ ID NO 19
<211> LENGTH: 30
<212> TYPE: PRT
<213> ORGANISM: Homo sapiens

<400> SEQUENCE: 19

```
Arg Gly Lys Ser Ser Ser Tyr Ser Lys Gln Phe Thr Ser Ser Thr Ser
1               5                   10                  15

Tyr Asn Arg Gly Asp Ser Thr Phe Glu Ser Lys Ser Tyr Lys
            20                  25                  30
```

<210> SEQ ID NO 20
<211> LENGTH: 32
<212> TYPE: PRT
<213> ORGANISM: Homo sapiens

<400> SEQUENCE: 20

```
Lys Ser Tyr Lys Met Ala Asp Glu Ala Gly Ser Glu Ala Asp His Glu
1               5                   10                  15

Gly Thr His Ser Thr Lys Arg Gly His Ala Lys Ser Arg Pro Val Arg
            20                  25                  30
```

<210> SEQ ID NO 21
<211> LENGTH: 18
<212> TYPE: PRT
<213> ORGANISM: Homo sapiens

<400> SEQUENCE: 21

```
Lys Ser Ser Ser Tyr Ser Lys Gln Phe Thr Ser Ser Thr Ser Tyr Asn
1               5                   10                  15

Arg Gly
```

<210> SEQ ID NO 22
<211> LENGTH: 27
<212> TYPE: PRT
<213> ORGANISM: Homo sapiens

<400> SEQUENCE: 22

```
Gly Pro Arg Arg Tyr Thr Ile Ala Ala Leu Leu Ser Pro Tyr Ser Tyr
1               5                   10                  15

Ser Thr Thr Ala Val Val Thr Asn Pro Lys Glu
            20                  25
```

<210> SEQ ID NO 23
<211> LENGTH: 10
<212> TYPE: PRT
<213> ORGANISM: Homo sapiens

```
<400> SEQUENCE: 23

Lys Pro Glu Ala Ser Phe Ser Pro Arg Arg
1               5                   10

<210> SEQ ID NO 24
<211> LENGTH: 12
<212> TYPE: PRT
<213> ORGANISM: Homo sapiens

<400> SEQUENCE: 24

Ile Pro Lys Pro Glu Ala Ser Phe Ser Pro Arg Arg
1               5                   10

<210> SEQ ID NO 25
<211> LENGTH: 14
<212> TYPE: PRT
<213> ORGANISM: Homo sapiens

<400> SEQUENCE: 25

Pro Pro Asp Val Pro Asp His Ala Ala Tyr His Pro Phe Arg
1               5                   10

<210> SEQ ID NO 26
<211> LENGTH: 15
<212> TYPE: PRT
<213> ORGANISM: Homo sapiens

<400> SEQUENCE: 26

Gly Pro Pro Asp Val Pro Asp His Ala Ala Tyr His Pro Phe Arg
1               5                   10                  15

<210> SEQ ID NO 27
<211> LENGTH: 16
<212> TYPE: PRT
<213> ORGANISM: Homo sapiens

<400> SEQUENCE: 27

Pro Gly Pro Pro Asp Val Pro Asp His Ala Ala Tyr His Pro Phe Arg
1               5                   10                  15

<210> SEQ ID NO 28
<211> LENGTH: 17
<212> TYPE: PRT
<213> ORGANISM: Homo sapiens

<400> SEQUENCE: 28

Leu Pro Gly Pro Pro Asp Val Pro Asp His Ala Ala Tyr His Pro Phe
1               5                   10                  15

Arg

<210> SEQ ID NO 29
<211> LENGTH: 17
<212> TYPE: PRT
<213> ORGANISM: Homo sapiens

<400> SEQUENCE: 29

Phe Phe Lys Tyr Tyr Leu Gln Gly Ala Lys Ile Pro Lys Pro Glu Ala
1               5                   10                  15

Ser

<210> SEQ ID NO 30
<211> LENGTH: 19
<212> TYPE: PRT
```

-continued

<213> ORGANISM: Homo sapiens

<400> SEQUENCE: 30

Tyr Tyr Leu Gln Gly Ala Lys Ile Pro Lys Pro Glu Ala Ser Phe Ser
1               5                   10                  15

Pro Arg Arg

<210> SEQ ID NO 31
<211> LENGTH: 18
<212> TYPE: PRT
<213> ORGANISM: Homo sapiens

<400> SEQUENCE: 31

Thr Phe Phe Lys Tyr Tyr Leu Gln Gly Ala Lys Ile Pro Lys Pro Glu
1               5                   10                  15

Ala Ser

<210> SEQ ID NO 32
<211> LENGTH: 19
<212> TYPE: PRT
<213> ORGANISM: Homo sapiens

<400> SEQUENCE: 32

Thr Phe Phe Lys Tyr Tyr Leu Gln Gly Ala Lys Ile Pro Lys Pro Glu
1               5                   10                  15

Ala Ser Phe

<210> SEQ ID NO 33
<211> LENGTH: 20
<212> TYPE: PRT
<213> ORGANISM: Homo sapiens

<400> SEQUENCE: 33

Lys Tyr Tyr Leu Gln Gly Ala Lys Ile Pro Lys Pro Glu Ala Ser Phe
1               5                   10                  15

Ser Pro Arg Arg
            20

<210> SEQ ID NO 34
<211> LENGTH: 23
<212> TYPE: PRT
<213> ORGANISM: Homo sapiens

<400> SEQUENCE: 34

His Ser Gly Ser Thr Phe Phe Lys Tyr Tyr Leu Gln Gly Ala Lys Ile
1               5                   10                  15

Pro Lys Pro Glu Ala Ser Phe
            20

<210> SEQ ID NO 35
<211> LENGTH: 23
<212> TYPE: PRT
<213> ORGANISM: Homo sapiens

<400> SEQUENCE: 35

Val His Ser Gly Ser Thr Phe Phe Lys Tyr Tyr Leu Gln Gly Ala Lys
1               5                   10                  15

Ile Pro Lys Pro Glu Ala Ser
            20

<210> SEQ ID NO 36
<211> LENGTH: 27

```
<212> TYPE: PRT
<213> ORGANISM: Homo sapiens

<400> SEQUENCE: 36

Pro Gly Val Leu Ser Ser Arg Gln Leu Gly Leu Pro Gly Pro Pro Asp
 1               5                  10                  15

Val Pro Asp His Ala Ala Tyr His Pro Phe Arg
             20                  25

<210> SEQ ID NO 37
<211> LENGTH: 28
<212> TYPE: PRT
<213> ORGANISM: Homo sapiens

<400> SEQUENCE: 37

Arg Pro Gly Val Leu Ser Ser Arg Gln Leu Gly Leu Pro Gly Pro Pro
 1               5                  10                  15

Asp Val Pro Asp His Ala Ala Tyr His Pro Phe Arg
             20                  25

<210> SEQ ID NO 38
<211> LENGTH: 27
<212> TYPE: PRT
<213> ORGANISM: Homo sapiens

<400> SEQUENCE: 38

His Ser Gly Ser Thr Phe Phe Lys Tyr Tyr Leu Gln Gly Ala Lys Ile
 1               5                  10                  15

Pro Lys Pro Glu Ala Ser Phe Ser Pro Arg Arg
             20                  25

<210> SEQ ID NO 39
<211> LENGTH: 29
<212> TYPE: PRT
<213> ORGANISM: Homo sapiens

<400> SEQUENCE: 39

Asn Phe Arg Pro Gly Val Leu Ser Ser Arg Gln Leu Gly Leu Pro Gly
 1               5                  10                  15

Pro Pro Asp Val Pro Asp His Ala Ala Tyr His Pro Phe
             20                  25

<210> SEQ ID NO 40
<211> LENGTH: 30
<212> TYPE: PRT
<213> ORGANISM: Homo sapiens

<400> SEQUENCE: 40

Arg Asn Val His Ser Gly Ser Thr Phe Phe Lys Tyr Tyr Leu Gln Gly
 1               5                  10                  15

Ala Lys Ile Pro Lys Pro Glu Ala Ser Phe Ser Pro Arg Arg
             20                  25                  30

<210> SEQ ID NO 41
<211> LENGTH: 32
<212> TYPE: PRT
<213> ORGANISM: Homo sapiens
<220> FEATURE:
<221> NAME/KEY: VARIANT
<222> LOCATION: 2
<223> OTHER INFORMATION: oxidized methionine

<400> SEQUENCE: 41

Arg Met Asn Phe Arg Pro Gly Val Leu Ser Ser Arg Gln Leu Gly Leu
```

```
                1               5                  10                 15
Pro Gly Pro Pro Asp Val Pro Asp His Ala Ala Tyr His Pro Phe Arg
        20                  25                 30

<210> SEQ ID NO 42
<211> LENGTH: 40
<212> TYPE: PRT
<213> ORGANISM: Homo sapiens

<400> SEQUENCE: 42

Arg Gln Ala Gly Ala Ala Gly Ser Arg Met Asn Phe Arg Pro Gly Val
1               5                  10                 15

Leu Ser Ser Arg Gln Leu Gly Leu Pro Gly Pro Pro Asp Val Pro Asp
            20                  25                 30

His Ala Ala Tyr His Pro Phe Arg
        35                  40

<210> SEQ ID NO 43
<211> LENGTH: 40
<212> TYPE: PRT
<213> ORGANISM: Homo sapiens
<220> FEATURE:
<221> NAME/KEY: VARIANT
<222> LOCATION: 10
<223> OTHER INFORMATION: oxidized methionine

<400> SEQUENCE: 43

Arg Gln Ala Gly Ala Ala Gly Ser Arg Met Asn Phe Arg Pro Gly Val
1               5                  10                 15

Leu Ser Ser Arg Gln Leu Gly Leu Pro Gly Pro Pro Asp Val Pro Asp
            20                  25                 30

His Ala Ala Tyr His Pro Phe Arg
        35                  40

<210> SEQ ID NO 44
<211> LENGTH: 42
<212> TYPE: PRT
<213> ORGANISM: Homo sapiens
<220> FEATURE:
<221> NAME/KEY: VARIANT
<222> LOCATION: 12
<223> OTHER INFORMATION: oxidized methionine

<400> SEQUENCE: 44

Trp Asn Arg Gln Ala Gly Ala Ala Gly Ser Arg Met Asn Phe Arg Pro
1               5                  10                 15

Gly Val Leu Ser Ser Arg Gln Leu Gly Leu Pro Gly Pro Pro Asp Val
            20                  25                 30

Pro Asp His Ala Ala Tyr His Pro Phe Arg
        35                  40

<210> SEQ ID NO 45
<211> LENGTH: 4
<212> TYPE: PRT
<213> ORGANISM: Homo sapiens

<400> SEQUENCE: 45

Lys Asp Glu Leu
1
```